United States Patent
Van Vlijmen et al.

(10) Patent No.: US 8,961,976 B2
(45) Date of Patent: *Feb. 24, 2015

(54) ANTI-CD154 ANTIBODIES

(71) Applicant: Biogen Idec Ma Inc., Cambridge, MA (US)

(72) Inventors: Herman Van Vlijmen, Somerville, MA (US); Alexey Lugovskoy, Woburn, MA (US); Karl Hanf, Billerica, MA (US)

(73) Assignee: Biogen Idec Ma Inc., Cambridge, MA (US)

(\*) Notice: Subject to any disclaimer, the term of this patent is extended or adjusted under 35 U.S.C. 154(b) by 0 days.

This patent is subject to a terminal disclaimer.

(21) Appl. No.: 14/134,753

(22) Filed: Dec. 19, 2013

(65) Prior Publication Data

US 2014/0220031 A1 Aug. 7, 2014

Related U.S. Application Data

(63) Continuation of application No. 11/572,647, filed as application No. PCT/US2005/026320 on Jul. 26, 2005, now Pat. No. 8,647,625.

(60) Provisional application No. 60/591,337, filed on Jul. 26, 2004.

(51) Int. Cl.
*A61K 39/395* (2006.01)
*C07K 16/28* (2006.01)
*A61K 39/00* (2006.01)

(52) U.S. Cl.
CPC ....... *C07K 16/2875* (2013.01); *A61K 2039/505* (2013.01); *C07K 2299/00* (2013.01); *C07K 2317/24* (2013.01); *C07K 2317/55* (2013.01); *C07K 2317/76* (2013.01); *C07K 2317/92* (2013.01); *Y10S 435/81* (2013.01)
USPC .................. 424/154.1; 424/130.1; 424/133.1; 424/134.1; 424/141.1; 424/142.1; 424/143.1; 424/144.1; 424/152.1; 424/153.1; 424/173.1; 530/387.1; 530/387.3; 530/388.1; 530/388.15; 530/388.2; 530/388.22; 530/388.7; 530/388.73; 530/388.75; 435/810

(58) Field of Classification Search
None
See application file for complete search history.

(56) References Cited

U.S. PATENT DOCUMENTS

| | | | |
|---|---|---|---|
| 5,474,771 A | 12/1995 | Lederman et al. | |
| 5,585,097 A | 12/1996 | Bolt et al. | |
| 5,624,821 A | 4/1997 | Winter et al. | |
| 5,648,260 A | 7/1997 | Winter et al. | |
| 5,714,350 A | 2/1998 | Co et al. | |
| 5,747,037 A | 5/1998 | Noelle et al. | |
| 5,876,718 A | 3/1999 | Noelle et al. | |
| 6,165,745 A | 12/2000 | Ward et al. | |
| 6,194,551 B1 | 2/2001 | Idusogie et al. | |
| 6,218,149 B1 | 4/2001 | Morrison et al. | |
| 6,230,102 B1 | 5/2001 | Tidor et al. | |
| 6,242,195 B1 | 6/2001 | Idusogie et al. | |
| 6,277,375 B1 | 8/2001 | Ward | |
| 6,284,536 B1 | 9/2001 | Morrison et al. | |
| 6,312,692 B1 | 11/2001 | Noelle et al. | |
| 6,340,459 B1 | 1/2002 | Yellin et al. | |
| 6,350,861 B1 | 2/2002 | Co et al. | |
| 6,528,624 B1 | 3/2003 | Idusogie et al. | |
| 6,538,124 B1 | 3/2003 | Idusogie et al. | |
| 6,720,165 B2 | 4/2004 | Nock et al. | |
| 6,737,056 B1 | 5/2004 | Presta | |
| 6,821,505 B2 | 11/2004 | Ward | |
| 6,933,368 B2 | 8/2005 | Co et al. | |
| 6,979,553 B2 | 12/2005 | Farinas et al. | |
| 7,083,784 B2 | 8/2006 | Dall'Acqua et al. | |
| 7,117,096 B2 | 10/2006 | Luo et al. | |
| 7,183,387 B1 | 2/2007 | Presta | |
| 7,217,797 B2 | 5/2007 | Hinton et al. | |
| 7,217,798 B2 | 5/2007 | Hinton et al. | |
| 7,247,302 B1 | 7/2007 | Rosok et al. | |
| 7,297,775 B2 | 11/2007 | Idusogie et al. | |
| 7,317,091 B2 | 1/2008 | Lazar et al. | |
| 7,332,581 B2 | 2/2008 | Presta | |
| 7,335,742 B2 | 2/2008 | Presta | |
| 7,351,803 B2 | 4/2008 | Johnson et al. | |
| 7,355,008 B2 | 4/2008 | Stavenhagen et al. | |
| 8,293,237 B2 | 10/2012 | Burkly et al. | |
| 8,647,625 B2 | 2/2014 | Van Vlijmen et al. | |
| 8,784,823 B2 | 7/2014 | Burkly et al. | |

(Continued)

FOREIGN PATENT DOCUMENTS

CN 1844147 A 10/2006
EA 007905 2/2007

(Continued)

OTHER PUBLICATIONS

Boumpas, D.T., et al., "A Short Course of BG9588 (Anti-CD40 Ligand Antibody) Improves Serologic Activity and Decreases Hematuria in Patients with Proliferative Lupus Glomerulonephritis" Arthritis & Rheumatism, Mar. 2003, vol. 48, No. 3, pp. 719-727.
Cammack, R. et al., p. 567 of Oxford Dictionary of Biochemistry and Molecular Biology, 2nd Edition, Oxford University Press, 2006.
Carter et al., "Humanization of an anti-p185 HER2 antibody for human cancer therapy", May 1992, Proc. Natl. Acad Sci USA vol. 89, pp. 4285-4289, Immunology.
Durie, F.H. et al., "Prevention of Collagen-Induced Arthritis with an Antibody to gp39, the Ligand for CD40", Science, Sep. 3, 1993, vol. 261, pp. 1328-1330.
Kuwana M. et al., "Effect of a Single Injection of Humanized Anti-CD154 monoclonal Antibody on the Platelet-specific Autoimmune Response in Patients with Immune Thrombocytopenic Purpura", Blood, Feb. 15, 2004, vol. 103, No. 4, pp. 1229-1236.

(Continued)

Primary Examiner — Phillip Gambel
(74) Attorney, Agent, or Firm — Lando & Anastasi LLP

(57) ABSTRACT

The present invention provides peptides, and fragments thereof, and antibodies, or fragments thereof comprising the same, wherein the peptide comprises at least one amino acid substitution compared to wild type 5c8 antibody. The present invention also provides compositions and methods of treating CD154-related diseases or disorders in a subject.

35 Claims, No Drawings

(56) References Cited

U.S. PATENT DOCUMENTS

| | | |
|---|---|---|
| 2002/0119150 A1 | 8/2002 | Kirk et al. |
| 2002/0131968 A1 | 9/2002 | Waldmann et al. |
| 2002/0147312 A1 | 10/2002 | O'Keefe et al. |
| 2002/0193573 A1 | 12/2002 | Nock et al. |
| 2003/0026692 A1 | 2/2003 | Lutz |
| 2003/0054407 A1 | 3/2003 | Luo |
| 2003/0072754 A1 | 4/2003 | Kenyon et al. |
| 2003/0073164 A1 | 4/2003 | Simmons et al. |
| 2003/0120044 A1 | 6/2003 | Huse et al. |
| 2003/0158389 A1 | 8/2003 | Idusogie et al. |
| 2003/0224397 A1 | 12/2003 | Lowman et al. |
| 2003/0235861 A1 | 12/2003 | Zheng et al. |
| 2004/0006208 A1 | 1/2004 | Karpusas et al. |
| 2004/0006216 A1 | 1/2004 | Waldmann et al. |
| 2004/0010124 A1 | 1/2004 | Johnson et al. |
| 2004/0010376 A1 | 1/2004 | Luo et al. |
| 2004/0091957 A1 | 5/2004 | Nock et al. |
| 2004/0110226 A1 | 6/2004 | Lazar et al. |
| 2004/0132101 A1 | 7/2004 | Lazar et al. |
| 2004/0191244 A1 | 9/2004 | Presta |
| 2004/0228856 A1 | 11/2004 | Presta |
| 2005/0054832 A1 | 3/2005 | Lazar et al. |
| 2005/0064514 A1 | 3/2005 | Stavenhagen et al. |
| 2005/0118174 A1 | 6/2005 | Presta |
| 2005/0170464 A1 | 8/2005 | Simmons et al. |
| 2005/0215768 A1 | 9/2005 | Armour et al. |
| 2005/0233382 A1 | 10/2005 | Presta |
| 2005/0244403 A1 | 11/2005 | Lazar et al. |
| 2006/0024298 A1 | 2/2006 | Lazar et al. |
| 2006/0160996 A9 | 7/2006 | Lazar et al. |
| 2006/0193856 A1 | 8/2006 | Taylor et al. |
| 2006/0275283 A1 | 12/2006 | van Vlijmen et al. |
| 2007/0048300 A1 | 3/2007 | Taylor et al. |
| 2007/0092516 A1 | 4/2007 | Waldmann et al. |
| 2007/0135998 A1 | 6/2007 | Van Vlijmen et al. |
| 2007/0202098 A1 | 8/2007 | Lazar et al. |
| 2007/0219133 A1 | 9/2007 | Lazar et al. |
| 2007/0224189 A1 | 9/2007 | Lazar et al. |
| 2007/0224192 A1 | 9/2007 | Lazar et al. |
| 2007/0237767 A1 | 10/2007 | Lazar et al. |
| 2007/0238665 A1 | 10/2007 | Lazar et al. |
| 2007/0243188 A1 | 10/2007 | Lazar et al. |
| 2007/0244303 A1 | 10/2007 | Johnson et al. |
| 2007/0248602 A1 | 10/2007 | Lazar et al. |
| 2007/0248603 A1 | 10/2007 | Lazar et al. |
| 2008/0050371 A1 | 2/2008 | Johnson et al. |
| 2008/0051563 A1 | 2/2008 | Lazar et al. |
| 2008/0206867 A1 | 8/2008 | Desjarlais et al. |
| 2008/0305116 A1 | 12/2008 | Van Vlijmen et al. |
| 2009/0010920 A1 | 1/2009 | Lazar et al. |
| 2009/0068175 A1 | 3/2009 | Lazar et al. |
| 2010/0104573 A1 | 4/2010 | Burkly et al. |

FOREIGN PATENT DOCUMENTS

| | | |
|---|---|---|
| EP | 255694 A1 | 2/1988 |
| EP | 0 555 880 A2 | 8/1993 |
| EP | 0 585 943 A2 | 3/1994 |
| JP | H06-179814 A | 6/1994 |
| WO | 88/07089 A1 | 9/1988 |
| WO | 89/07142 A1 | 8/1989 |
| WO | 93/08207 A1 | 4/1993 |
| WO | 93/09812 A1 | 5/1993 |
| WO | 93/19196 A1 | 9/1993 |
| WO | 93/22332 A2 | 11/1993 |
| WO | 94/04570 A1 | 3/1994 |
| WO | 94/28027 A1 | 12/1994 |
| WO | 94/29351 A2 | 12/1994 |
| WO | 9506481 A1 | 3/1995 |
| WO | 9506666 A1 | 3/1995 |
| WO | 9720063 A1 | 6/1997 |
| WO | 97/34631 A1 | 9/1997 |
| WO | 98/05787 A1 | 2/1998 |
| WO | 98/23289 A1 | 6/1998 |
| WO | 98/47531 A2 | 10/1998 |
| WO | 98/58672 A1 | 12/1998 |
| WO | 9922764 A1 | 5/1999 |
| WO | 99/51642 A1 | 10/1999 |
| WO | 9954484 A1 | 10/1999 |
| WO | 99/58572 A1 | 11/1999 |
| WO | 00/05268 A1 | 2/2000 |
| WO | 00/42072 A2 | 7/2000 |
| WO | 0168860 A1 | 9/2001 |
| WO | 01/79555 A2 | 10/2001 |
| WO | 01/93908 A1 | 12/2001 |
| WO | 02/18446 A2 | 3/2002 |
| WO | 0218445 A2 | 3/2002 |
| WO | 02/060919 A2 | 8/2002 |
| WO | 02/062850 A2 | 8/2002 |
| WO | 02066514 A2 | 8/2002 |
| WO | 02079232 A2 | 10/2002 |
| WO | 03/001870 A2 | 1/2003 |
| WO | 03/026692 A2 | 4/2003 |
| WO | 03031475 A2 | 4/2003 |
| WO | 03/035835 A2 | 5/2003 |
| WO | 03048306 A2 | 6/2003 |
| WO | 03059282 A2 | 7/2003 |
| WO | 03074679 A2 | 9/2003 |
| WO | 03/101485 A1 | 12/2003 |
| WO | 03099999 A2 | 12/2003 |
| WO | 2004/003019 A2 | 1/2004 |
| WO | 2004/029207 A2 | 4/2004 |
| WO | 2004/035752 A2 | 4/2004 |
| WO | 2004051268 A1 | 6/2004 |
| WO | 2004063351 A2 | 7/2004 |
| WO | 2004063963 A2 | 7/2004 |
| WO | 2004072116 A2 | 8/2004 |
| WO | 2004/074455 A2 | 9/2004 |
| WO | 2004/074499 A2 | 9/2004 |
| WO | 2004/099249 A2 | 11/2004 |
| WO | 2005/003175 A2 | 1/2005 |
| WO | 2005011376 A2 | 2/2005 |
| WO | 2005/018572 A2 | 3/2005 |
| WO | 2005035572 A2 | 4/2005 |
| WO | 2005/040217 A2 | 5/2005 |
| WO | 2005056606 A2 | 6/2005 |
| WO | 2005056759 A2 | 6/2005 |
| WO | 2005/070963 A1 | 8/2005 |
| WO | 2005/077981 A2 | 8/2005 |
| WO | 2005077415 A1 | 8/2005 |
| WO | 2005/115452 A2 | 12/2005 |
| WO | 2006/019447 A1 | 2/2006 |
| WO | 2006/020114 A2 | 2/2006 |
| WO | 2006/031370 A2 | 3/2006 |
| WO | 2006/033702 A2 | 3/2006 |
| WO | 2006030220 A1 | 3/2006 |
| WO | 2007019621 A1 | 2/2007 |
| WO | 2007/059332 A2 | 5/2007 |
| WO | 2007100289 A2 | 9/2007 |
| WO | 2008118356 A2 | 10/2008 |

OTHER PUBLICATIONS

Lunt, et al., "Large-scale production, properties, and commercial application of polyactic acid polymers," Polymer Degradation and Stability, 59, 145-152, 1998.
Peters, et al., "CD40 and Autoimmunity:The Dark Side of Great Activator", Semin Immunol., vol. 21, No. 5, pp. 293-300, (2009).
Sato et al., "Humanization of a Mouse Anti-Human Interleukin-6 Receptor Antibody Comparing Two Methods for Selecting Human Framework Regions", Molecular Immunology, (1994) vol. 31, No. 5, pp. 371-381.
Translation of JPH06-179814 (original Japanese document published Jun. 28, 1994).
Weir et al., "A new generation of high-affinity humanized PEGylated Fab fragment anti-tumor necrosis factor alpha monoclonal antibodies", Therapy (2006) (4) 535-545.
Pound, J.D., et al., "Aglycosylated Chimaeric Human IgG3 Can Trigger the Human Phagocyte Respiratory Burst," Molecular Immunology, 30(3):233-241 (1993).
Press Release from Biogen website (www.prnewswire.com), "Biogen Says it Has Haulted Several Trials of Anti-CD40 Ligand Monoclonal Antibody" (Oct. 21, 1999).

(56) References Cited

OTHER PUBLICATIONS

Press Release from Biogen website (www.prnewswire.com), "Biogen Says it Has Stopped Ongoing Trials of Anti-CD40 Ligand Monoclonal Antibody" (Nov. 2, 1999).
Press Release from IDEC Pharmaceuticals, Inc., IDEC-131 (Apr. 20, 2000).
Quezada et al, "Distinct mechanisms of action of anti-CD154 in early versus late treatment of murine lupus nephritis", Arthritis Rheumatism 48(9):2541-2554 (2003).
Radaev et al, "The structure of a human type III Fcγ receptor complex with Fe", J. Biol. Chem. 276:16469-16477 (2001).
Raju et al., "Species-specific variation in glycosylation of IgG: evidence for the species-specific sialylation and branch-specific galactosylation and importance for engineering recombinant I glycoprotein therapeutics," Glycobiology, 10 (5):477-486 (2000).
Raju, "Glycosylation Variations with Expression Systems and Their Impact on Biological Activity of Therapeutic Immunoglobulins," BioProcess International, pp. 44-53 (2003).
Ranheim, et al., "Activated T cells induce expression of B7/BB1 on normal or leukemic B cells through a CD40-dependent signal", Journal of Experimental Medicine, vol. 177, pp. 925-935, (1993).
Ravetch et al., "Fe Receptors," Annu. Rev. Immunol., 9:457-492 (1991).
Rocchia et al., "Extending the applicability of the nonlinear Poisson-Boltzmann Equation: Multiple Dielectric Constants and Multivalent Ions," Journal of Physical Chemistry, 105:6507-6514 (2001 ).
Rudikoff et al, "Single amino acid substitution altering antigen-binding specificity", Proc. Natl. Acad. Sci. USA vol. 79 p. 1979-1983 (1982).
Samoilova, E.B., et al., "CD40L Blockade Prevents Autoimmune Encephalomyelitis and Hampers TH1 But Not TH2 Pathway of T Cell Differentiation," Journal of Molecular Medicine, 75:603-608 (1997).
Sanchez-Fueyo et al., "The Complement Dependent Cytotoxicity (CDC) Immune Effector Mechanism Contributes to Anti-CD154 Induced Immunosuppression," Transplantation, 74(6):898-900 (2002).
Sarmay et al., "Ligand Inhibition Studies on the Role of Fc Receptors in Antibody-Dependent Cell-Mediated Cytotoxicity," Molecular Immunolor:w, 21(1 ):43-51 (1984).
Schönbeck, et al, "The CD40/CD154 receptor/ligand dyad.", Cell Mol Life Sci. vol. 58(1), pp. 4-43 (2001).
Seung, et al. "Allogeneic hematopoietic chimerism in mice treated with sublethal myeloablation and anti-CD154 antibody: absence of graft-versus-host disease, induction of skin allograft tolerance, and prevention of recurrent autoimmunity in islet-allografted NOD/Lt mice", Blood, vol. 95, No. 6, p. 2175-2182 Mar. 15, 2000.
Sharabi, et al., "Mixed chimerism and permanent specific transplantation tolerance induced by a nonlethal preparative regimen", Journal of Experimental Medicine, vol. 169, pp. 493-502, (1989).
Shields et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry, 276 (9):6591-6604 (2001 ).
Shields et al., "Lack of Fucose on Human IgG1 N-Linked Oligosaccharide Improves Binding to Human FcγRIII and Antibody-dependent Cellular Toxicity," The Journal of Biological Chemistry, 277(30):26733-236740(2002).
Shinkawa et al., "The Absence of Fucose but Not the Presence of Galactose or Bisecting NAcetylglucosamine of Human IgG1 Complex-type Oligosaccharides Shows the Critical Role of Enhancing Antibody-dependent Cellular Cytotoxicity," The Journal of Biological Chemistry, 278(5):3466-3473 (2003).
Shitara et al., "A new vector for the high level expression of chimeric antibodies in myeloma cells," Journal of Immunological Methods, vol. 167:271-278 (1994).
Shopes, "A Genetically Engineered Human IgG Mutant with Enhanced Cytolytic Activity," The Journal of Immunology, 148(9):2918-2922 (1992).

Simmons et al., "Expression of full-length immunoglobulins in *Escherichia coli*: rapid and efficient production of aglycosylated antibodies", 263 J. Immunological Methods: 133-147, (2002).
Sinha et al., "Electrostatics in protein binding and function," Current Protein and Peptide Science 3:601-614 (2002).
Skolnick et al., "From genes to protein structure and function: novel applications of computational approaches in the genomic era," Trends in Biotechnology, 18(1):34-39 (2000).
Smith-Gill et al. "Contributions of immunoglobulin heavy and light chains to antibody specificity for lysozyme and two haptens." J. Immunol. 139:4135-4144 (1987).
Sondermann et al., "Mediation and Modulation of Antibody Function," Biochemical Society Transactions, 30:481-486 (2002).
Sondermann et al., "The 3.2-Å crystal structure of the human IgG1 Fc fragment-FcγRIII complex," Nature, 406:267-273 (2000).
Song et al. "Light chain of natural antibody plays a dominant role in protein antigen binding." Biochem Biophys Res Comm 268:390-394 (2000).
Spriggs, et al., "Recombinant Human CD404 ligand stimulates B cell proliferation and Immunoglobulin E secretion", Journal of Experimental Medicine, vol. 176, pp. 1543-1550 (1992).
Stamenkovic, et al., "A B-lymphocyte activation molecule related to the nerve growth factor receptor and induced by cytokines in carcinomas", The EMBO Journal, vol. 8, No. 5, pp. 1403-1410, (1989).
Stuber et al., "Blocking the CD-40L-CD40 interaction in vivo specifically prevents the priming of T helper 1 cells through the inhibition of interleukin 12 secretion", 183 J. Exp. Med.: 693-698 (1995).
Supplementary European Search Report, Application No. 04872045.1, (WO2005018572) May 7, 2009.
Supplementary Partial European Search Report for Application No. 04779301.3 (Apr. 26, 2007).
Tamm et al., "IgG Binding Sites on Human Fcγ Receptors," Intern. Rev. Immunol., vol. 16:57-85 (1997).
Tao et al., "Structural Features of Human Immunoglobulin G that Determine Isotype-specific Differences in Complement Activation," J. Exp. Med., 178:661-667 (1993).
Tao, Mi-Hua, et al., "Studies of Aglycosylated Chimeric Mouse-Human IgG Role of Carbohydrate in the Structure and Effector Functions Mediated by the Human IgG Constant Region," Journal of Immunology, 143(8):2595-2601 (1989).
Thomas et al., "Structure of an anti-blood group A Fv and improvement of its binding affinity without losss of specificity," The Journal of Biological Chemistry 277(3):2059-2064 (2002).
Toubi et al. "The role of CD4O-CD154 interactions in autoimmunity and the benefit of disrupting this pathway." Immunity. 37(6-7):457-64; Sep.-Nov. 2004. Abstract.
Trebak et al., "Efficient laboratory-scale production of monoclonal antibodies using membrane-based high-density cell culture technology," Journal of Immunological Methods, 230:59-70 (1999).
Turka, et al., "T-cell activation by the CD28 ligand B7 is required for cardiac allograft rejection in vivo" Proceedings of the National Academy of Sciences, vol. 89, pp. 11102-11105, (1992).
Umana et al., "Engineered glycoforms of an antineuroblastoma IgG1 with optimized antibodydependent cellular cytotoxic activity," Nature Biotechnology, 17:176-180 (1999).
Vajdos et al. "Comprehensive Functional Maps of the Antigen-binding Site of an Anti-ErbB2 Antibody Obtained with Shotgun Scanning Mutagenesis" J. Mol. Biol. 320, 415-428, (2002).
Valerius et al. "FcaRI (CD89) as a Novel Trigger Molecule for Bispecific Antibody Therapy." Blood, vol. 90 (11 ):4485-4492 (1997).
Vallette et al., "Construction of mutant and chimeric genes using the polymerase chain reaction," Nucleic Acids. Res., 17:723-733 (1989).
Vitetta et al., "Considering Therapeutic Antibodies," Science, vol. 313:308-309 (2006).
W.H.O., "Review of the notation for the allotypic and related markers of human immunoglobulins," Eur. J. Immunol. vol. 6:599-601 (1976).
Waldmann "Manipulation of T cell responses with monoclonal antibodies", Annu. Rev. Immunol., vol. 7, pp. 407-444, (1989).

(56) References Cited

OTHER PUBLICATIONS

Waldmann "Immune Receptors: Targets for Therapy of Leukemia/Lymphoma, Autoimmune Diseases and for the Prevention of Allograft Rejection", Annu. Rev. Immunol., vol. 10, pp. 675-704 (1992).

Dorai, H., et al., "Aglycosylated Chimeric Mouse/Human IgG1 Antibody Retains Some Effector Function," Hybridoma, 10(2):211-217 (1991).

Duncan et al., "Localization of the binding site for the human high-affinity Fe receptors on IgG," Nature, 332:563-564 (1988).

Duncan et al., "The binding site for C1q on IgG," Nature, 332:738-740 (1988).

Elster et al., "Treatment with the humanized CD154-specific monoclonal antibody, hu5C8, prevents acute rejection of primary skin allografts in nonhuman primates", Transplantation 72: 1473-1478 (2001).

EP Search Report for EP 10 15 5543 mailed May 27, 2010.

European Office Action for Application No. 04782045, dated Dec. 30, 2009.

Extended EP Search Report for European Application No. 11182599.8, dated Jan. 20, 2012.

Extended European Search Report, EP Application No. 05817412.9, dated Jun. 5, 2009.

Eynon and Parker, "Small B Cells as Antigen-presenting Cells in the Induction of Tolerance to Soluble Protein Antigen", Journal Experimental Medicine, vol. 175, pp. 131-138 (1992).

Fanslow, et al., "Soluble forms of CD40 inhibit biologic responses of human B cells", Journal of Immunology, vol. 149, No. 2, pp. 655-660 (1992).

Ferrant et al., "The contribution of Fe effector mechanisms in the efficacy of anti-CD154 immunotherapy depends on the nature of the immune challenge," International Immunology, 16(11):1583-1594 (2004).

Fiumara et al., "CD40 ligand (CD154) and tumour necrosis factor-related apoptosis inducing ligand (Apo.2L) in haematological malignancies," Br. J. Haematol, 113:265-274 (2001).

Foy, T.M. et al. "In Vivo CD40-gp39 Interactions are essential for Thymus-dependent Hummoral Immunity. II. Prolonged suppression of theHumoral Immune Response by an antibody to the ligand for CD40, gp39" J. Exp. Med. 178:1567-1575 (1993).

Fridman et al., "Analysis of IgGFcyR Interactions in Solution: Mapping of the FcyR Binding Site and Evidence for a Conformational Change Occuring in the Fe Region," Immunology Letters, vol. 73(2-3) No. 409 (2000).

Friend, P.J., et al., "Phase 1 Study of an Engineered Aglycosylated Humanized CD3 Antibody in Renal Transplant Rejection," Transplantation, 68(11):1632-1637 (1999).

Gazzano-Santoro et al., "A non-radioactive complement-dependent cytotoxicity assay for anti-CD20 monoclonal antibody," Journal ofImmunological Methods, 202:163-171 (1997).

Gergely et al., "Fe receptors on lymphocytes and K cells," Biochemical Society Transactions, 12(5):739-743 (1984).

Gillies et al., "Improving the Efficacy of Antibody-Interleukin 2 Fusion Proteins by Reducing Their Interaction with Fe Receptors," Cancer Research, 59:2159-2166 (1999).

Graca, et al, "Cutting Edge: Anti-CD154 Therapeutic Antibodies Induce Infectious Transplantation Tolerance", The Journal of Immunology, vol. 165 No. 9, p. 4783-4786, Nov. 1, 2000.

Graddis et al., "Designing Proteins That Work Using Recombinant Technologies," Current Pharmaceutical Biotechnology, 3:285-297 (2002).

Gray et al., Memory B cell development but not germinal center formation is impaired by in vitro blockade of CD40-CD40 ligand interaction, J. Exp. Med. 180: 141-155 (1994).

Hand, P.H., et al., "Comparative Biological Properties of a Recombinant Chimeric Anti-Carcinoma mAB and a Recombinant Aglycosylated Variant," Cancer Immunology Immunotherapy, 35:165-174 (1992).

Harris "Therapeutic antibodies—the coming of age", TIBTECH, vol. 11, pp. 42-44 (1993).

Hayes et al., "Combining computational and experimental screening for rapid optimization of protein properties," PNAS, vol. 99(25):15926-15931 (2002).

Hezareh et al., "Effector Function Activities of a Panel of Mutants of a Broadly Neutralizing Antibody against Human Immunodeficiency Virus Type 1 ,"Journal of Virology, 75(24):12161-12168 (2001).

Hobbs, S.M., et al., "Interaction of Aglycosyl Immunoglobulins with the IgG Fe Transport Receptor from Neonatal Rat Gut: Comparison ot: Deglycosylation by Tunicamycin Treatment and Genetic Engineering," Molecular Immunology, 29 (7/8):949-956 (1992).

Hodgkin, et al., "Separation of events mediating B cell proliferation and Ig production by using T cell membranes and lymphokines", Journal of Immunology, vol. 145, No. 7, pp. 2025-2034, (1990).

Hollenbaugh, et al., "The human T cell antigen gp39, a member of the TNF gene family, is a ligand for the CD40 receptor: expression of a soluble form of gp39 with B cell co-stimulatory activity", The EMBO Journal, vol. 11, No. 12, pp. 4313-4321 (1992).

Holm et al "Functional mapping and single chain construction of the anti-cytokeratin 8 monoclonal antibody TS1" Mol. Immunol. 44: 1075-1084, (2007).

Hsu et al., "Differential N-Giycan Patterns of Secreted and Intracellular IgG Produced in Trichoplusia ni Cells," The Journal of Biological Chemistry, 272(14):9062-9070 (1997).

Hsu et al., "Heteromultimeric complexes of CD40 ligand are present on the cell surface of human T lymphocytes," Journal of Biological Chemistry, 272(2):911-915 (1997).

Idusogie et al., "Mapping of the C1q Binding Site on Rituxan, a Chimeric Antibody with a Human IgG1 Fe," The Journal of Immunoloav, 164:4178-4184 (2000).

International Preliminary Report on Patentability & Written Opinion for Application No. PCT/US2004/024200 (WO2005/011376) (Feb. 12, 2006).

International Preliminary Report on Patentability & Written Opinion for PCT/US2004/018708 dated Dec. 13, 2005.

International Preliminary Report on Patentability for PCT/US2008/03735 dated Sep. 22, 2009.

International Report on Patentability for PCT/US2005/026320 dated Jan. 30, 2007.

International Search Report for Application No. PCT/US2004/024200 (WO2005/011376) (Mar. 31, 2006).

International Search Report for PCT/US2005/026320 dated Jan. 4, 2007.

International Search Report, International Application No. PCT/US2004/018708, dated Dec. 27, 2004.

International Search Report, International Application No. PCT/US2008/03735, dated Sep. 25, 2008.

Isaacs, et al., "Therapy with monoclonal antibodies. An in vivo model for the assessment of therapeutic potential", Journal of Immunology, vol. 148, No. 10, pp. 3062-3071 (1992).

Israel et al., "Increased clearance of IgG in mice that lack B2-microglobulin: possible protective role of FeRn," Immunology, 89:573-578 (1996).

Iwakoshi, et al. "Treatment of Allograft Recipients with Donor-Specific Transfusion and Anti-CD154 Antibody Leads to Deletion of Alloreactive CD8+ T Cells and Prolonged Graft Survival in a CTLA4-Dependent Manner" The Journal of Immunology, vol. 164 No. 1 512-521, Jan. 1, 2000.

Jang et al., "The structural basis for DNA binding by an anti-DNA autoantibody", Molecular Immunology 35:1207-1217 (1998).

Jefferis et al., "Giycosylation of Antibody Molecules: Structural and Functional Signficance," ChemicalImmunoloav, 65:111-128 (1997).

Kalled et al, "Apoptosis and altered dendritic cell homeostasis in lupus nephritis are limited by anti-CD154 treatment", Journal of Immunology 167:1740-1747 (2001).

Karpusas et al., "A crystal structure of an extracellular fragment of human CD40 ligand," Structure, 3(12):1426 (1995).

Karpusas et al., "Structure of CD40 ligand in complex with the Fab fragment of a neutralizing humanized antibody," Structure, 9(4):321-329 (2001).

Kawai, T., "Thromboembolic complications after treatment with monoclonal antibody against CD40 ligand", Nature Medicine, vol. 6, No. 2, 114, Feb. 2000.

(56) References Cited

OTHER PUBLICATIONS

Kenyon, N.S., "Long-Term Survival and Function of Intrahepatic Islet Allografts in Baboons Treated with Humanized Anti-CD154", Diabetes, vol. 48, Jul. 1-9, 1999.
Kenyon, N.S., et al., "Long-Term Survival and Function of Intrahepatic Islet Allografts in Rhesus Monkeys treated with Humanized Anti-CD154," Proceedings of the National Academy of Sciences of the USA, 96:8132-8137 (1999).
Kirk et al., "The role of CD154 in organ transplant rejection and acceptance," Philos. Trans. R. Soc.Lond. B. Sci., 356:691-702 (2001).
Kirk, A.d., et al., "Treatment with Humanized Monoclonal Antibody Against CD154 Prevents Acute Renal Allograft Rejection in Nonhuman Primates," Nature Medicine, 5(6):686-693 (1999).
Klein et al., "Expression of biological effector functions by immunoglobulin G molecules lacking the hinge region," Proc. Nat/. Acad. Sci. USA, 78(1):524-528 (1981).
Kobayashi et al., "Tryptophan H33 plays an important role in pyridmidine (6-4) pyrimidone photoproduct binding by a high affinity antibody", Protein Engineering 12:879-844 (1999).
Korthauer, et al., "Defective expression of T cell CD40 ligand causes X-linked immunodeficiency with hyper-IgM", Nature, vol. 361, pp. 539-541 (1993).
Koyama, I., "Thrombophilia Associated with Anti-CD154 Monoclonal Antibody Treatment and its Prophylaxis in Nonhuman Primates", Transplantation, vol. 77, No. 3, 460, (2004).
Kumar et al., "Molecular cloning and expression of the fabs of human autoantibodies in *Escherichia coli*: determination of the heavy or light chain contribution to the anti-DNA/-cardiolipin activity of the fab", J. Biol. Chem. 275:35129-35136 (2000).
Kunkel, "Rapid and efficient site-specific mutagenesis without phenotypic selection," Proc. Nat/.Acad. Sci. USA, 82:488-492 (1985).
Lane, et al., "Activated human T cells express a ligand for the human B cell-associated CD40 which participates in T-cell-dependent activation of B lymphocytes", European Journal of Immunology, vol. 22, pp. 2573-2578 (1992).
Larsen et al., "CD40-gp39 Interactions Play a Critical Role During Allograft Rejection: Suppression of Allograft Rejection by Blockade of the CD40-gp39 Pathway1" Transplantation 61: 4-9 (1996).
Lazar et al., "Engineered antibody Fe variants with enhanced effector function," PNAS, vol. 1 03(11 ):4005-4010 (2006).
Leader, K.A., et al., "Functional Interactions of Aglycosylated Monoclonal Anti-D with FcyRI+ and FcyRIII+ Cells," Immunology, 72:481-485 (1991 ).
Leatherbarrow et al., "The effect of aglycosylation on the binding of mouse IgG to staphylococcal protein A," FEBS Lett, 164(2):227-230 (1983).
Leatherbarrow, R.J., et al., "Effector Functions of a Monoclonal Aglycosylated Mouse IgG2a: Binding and Activation of Complement Component C1 and Interaction with Human Monocyte Fe Receptor," Molecular Immunology, 22(4): 407-415 (1985).
Lederman et al., "Identification of a novel surface protein on activated CD4+ T cells that induces contact-dependent 8 cell differentiation (help)," J. Exp. Med., 175(4):1 091-1101 (1992).
Lederman, S. et al. "Molecular Interactions Mediating T-B Lymphocyte Collaboration in Human Lymphoid Follicles" J. Immunology 149(12):3817-3826, (1992).
Lee et al., "Optimization of electrostatic binding free energy," Journal of Chemical Physics, 106(21 ):8681-8690 (1997).
Lenschow, et al., "Long-term Survival of Xenogeneic Pancreatic Islet Grafts Induced by CTLA4Ig", Science, vol. 257, pp. 789-790, (1992).
Lin, et al., "Long-Term Acceptance of Major Histocompatibility Complex Mismatched Cardiac Allografts Induced by CTLA4Ig Plus Donor-specific Transfusion", Journal of Experimental Medicine, vol. 178, pp. 1801-1806 (1993).
Linsley, et al., "Immunosuppression in Vivo by a Soluble Form of the CTLA-4 T Cell Activation Molecule", Science, vol. 257, pp. 792-795 (1992).

Liu et al., "Production of a Mouse-human Chimeric Monoclonal Antibody to CD20 with Potent Fc-Dependent Biologic Activity," The Journal of Immunology, vol. 139(10):3521-3526 (1987).
Lund et al., "Human FcyRI and FcyRIIInteract with Distinct but Overlapping Sites on Human IgG," The Journal of Immunology, 147(8):2657-2662 (1991).
Lund, J., et al., "A Protein Structural Change in Aglycosylated IgG3 Correlates with Loss of huFcyR1 and huFcyR111 Binding and/or Activation," Molecular Immunology, 27(11 ):1145-1153 (1990).
MacCallum et al. "Antibody-antigen Interactions: Contact Analysis and Binding Site Topography", J. Mol. Biol. 262:732-745, (1996).
Malmborg, et al, "Affinity and epitope profiling of mouse anti-CD40 monclonal antibodies", Scandinavian journal of immunology, Blackwell Science Publ., Oxford, GB, vol. 57, No. 6, 1, pp. 517-524 (Jun. 1, 2003).
Markees, et al., "Long-term survival of skin allografts induced by donor splenocytes and anti-CD154 antibody in thymectomized mice requires CD4(+) T cells, interferon-gamma, and CTLA4". J Clin Invest. 101(11): 24462455, Jun. 1, 1998.
Marshall, L.S. et al. "The Molecular Basis for T Cell Help in Humoral Immunity: CD 40 and Its Ligand gp39" J. Clin. Immunol. 13(3):165-174, (1993).
Marvin et al., "Redesigning an antibody fragment for faster association with its antigen," Biochemistry 42 (23):7077-7083 (2003).
Marzocchi•Machado et al., "The Influence of Antibody Functional Affinity on the Effector Functions involved in the Clearance of Circulating Immune Complexes Anti-BSA IgG/BSA," Immunological Investigations, 28(2&3):89-1 01 (1999).
Mian et al., "Structure, function and properties of antibody binding sites," Journal of Molecular Biology 217:133-151 (1991).
Miller, "To Build a Better Mousetrap, use human parts," JNCI Journal of the National Cancer Institute, 90(1 ): 14-16 (1998).
Monach et al.,"CD4+ and B Lymphocytes in Transplantation Immunity", Transplantation, vol. 55, 1356-1361, No. 6, Jun. 1993.
Monaco, "Methods of Inducing Immunological Tolerance to Tissue Allografts and Xenografts" Immunomethods 2:159-170 (1993).
Monk et al., "Fc-dependent depletion of activated T cells occurs through CD40L-specific antibody rather than costimulation blockade," Nature Medicine, 9(10):1275-1280 (2003).
Morrison et al.. "Variable Region Domain Exchange Influences the Functional Properties of IgG," The Journal of Immunology, vol. 160:2802-2808 (1998).
Mueller et al., "Humanized Porcine VCAM-specific Monoclonal Antibodies with Chimeric IgG2/G4 Constant Regions Block Human Leukocyte Binding to Porcine Endothelial Cells," Molecular Immunology, 34(6):441-452 (1997).
Nagelkerken et al., "FeR Interactions Do Not Play a Major Role in Inhibition of Experimental Autoimmune Encephalomyelitis by Anti-CD154 Monoclonal Antibodies," The Journal of Immunology, 173:993-999 (2004 ).
Natsume et al., "Engineered Antibodies of IgG1/IgG3 Mixed Isotype with Enhanced Cytotoxic Activities," Cancer Research, vol. 68(10):3863-3872 (2008).
Newkirk et al., "Differential clearance of glycoforms of IgG in normal and autoimmune-prone mice," Clin. Exp. Immunol., 106:259-264 (1996).
Noelle and Snow, "T helper cells", Current Opinion in Immunology, vol. 4, pp. 333-337, (1992).
Noelle et al., "CD40 and its ligand, an essential ligand-receptor pair for thymus-dependent B-cell activation", Immunology Today, vol. 13, pp. 431-433, (1992).
Noelle, R.J. et al. "A 39-kDa protein on activated helper T cells binds CD40 and transduces the signal for cognate activation of B cells" Proc. Natl. Acad. Sci. USA 89:6550-6554, (1992).
Nose M and Hans Wiczell: "Biological significance of carbohydrate chains on monoclonal antobodies" Proc Natl Acad Sci U S A., vol. 80, pp. 6632-6636, Jan. 1, 1983.
Novotny et al., "On the attribution of binding energy in antigen-antibody complexes McPC 603, D1.3, and HyHEL-5," Biochemistry 28(11 ):4735-4749 (1989).
Padlan, "A possible procedure for reducing the immunogenicity of antibody variable domains while preserving their ligand-binding properties," Molecular Immunology 28(4-5):489-498 (1991 ).

(56) References Cited

OTHER PUBLICATIONS

Patel et al., "Different culture methods lead to differences in glycosylation of a murine IgG monoclonal antibody," Biochem. J., 285:839-845 (1992).
Paul (Ed), Fundamental Immunology Review Press p. 242, 1993.
Paulie, et al., "The human B Lymphocyte and Carcinoma Antigen, CDw40, is a Phosphoprotein involved in growth signal transduction", Journal of Immunology, vol. 142, pp. 590-595, (1989).
Pendley et al., "Immunogenicity of therapeutic monoclonal antibodies," Current Opinion in Molecular Therapeutics, vol. 5(2):172-179 (2003).
Waldmann et al., "Monoclonal antibodies in diagnosis and therapy", Science, vol. 52, pp. 1657-1662, (1991).
Waldmann, "The new immunosuppression: just kill the T Cell," Nature Medicine, 9(10):1259-1260 (2003).
Walker, "Aglycosylation of human IgG1 and IgG3 monoclonal antibodies can eliminate recognition by human cells expressing FcvRI and/or FcvRII receptors," Biochem. J., 259:347-353 (1989).
Ward et al., "The effector functions of immunoglobulins: implications for therapy," Therapeutic Immunology, 2:77-94 (1995).
Ward et al., "Binding activities of a repertoire of single immunoglobin variable domains secreted from *Escherichia coli*", Nature 341:544-546 (1989).
Wee et al., "Anti-CD4 mAb therapy significantly delays the alloantibody response in a cynomolgus renal transplant model" Transplantation 58: 261-264 (1994).
Wells et al., "Cassette mutagenesis: an efficient method for generation of multiple mutations at defined sites," Gene, 34:315-323 (1985).
Williams, et al., "Studies of biologic and serologic activities of rabbit-IgG antibody depleted of carbohydrate residues" J Immunol., vol. 111, No. 6, pp. 1690-1698, 1973.
Winkelhake, et al., "Aglycosylantibody. Effects of exoglycosidase treatments on autochthonous antibody survival time in the circulation." J Biol Chem., vol. 251, No. 4, pp. 1074-1080, 1976.
Woof et al., "Localisation of the Monocyte-Binding Region on Human Immunoglobulin G," Molecular Immunology, 23 (3):319-330 (1986).
Wright et al., "Effect of Altered CH2-associated Carbohydrate Structure on the Functional Properties and In Vivo Fate of Chimeric Mouse-Human Immunoglobulin G1 ," J. Exp. Med., 180:1087-1096 (1994).
Wright, et al., "Effect of glycosylation on antibody function: implications for genetic engineering", Tibtech, Vo. 15, pp. 26-32, 1997.
Written Opinion for PCT/US2008/03735 dated Sep. 22, 2009.
Wu et al., "Humanization of a murine monoclonal antibody by simultaneous optimization of framework and CDR residues," Journal of Molecular Biology, 294:151-162 (1999).
Xu et al., "In Vitro Characterization of Five Humanized OKT3 Effector Function Variant Antibodies," Cellular Immunoloav, 200:16-26 (2000).
Xu, et al., "Humanized Anti-CD154 Antibody Therapry for the treatment of Allograft Rejection in Nonhuman Primates.", Transplantation, vol. 74, No. 4, pp. 940-943 (Oct. 15, 2002).
Yamada et al., "The CD154-CD40 costimulatory pathway in transplantation," Transplantation, 73, S36-9 (2002).
Yamane-Ohnuki et al., "Establishment of FUT8 Knockout Chinese Hamster Ovary Cells: An Ideal Host Cell Line for producing completely defucosylated antibodies with enhanced antibody-dependent cellular cytotoxicity." Biotechnol Bioeng. 87(5):614-22, Sep. 5, 2004.
Yamane-Ohnuki, et al., "Producing Completely Defucosylated Antibodies With Enhanced Antibody-Dependent Cellular Cytotoxicity," Biotechnology and Bioengineering, vol. 87(5):614-622 (2004).
Yellin, et al., "A human CD4-T cell Leukemia subclone with contact-dependent helper function", Journal of Immunology, vol. 147, pp. 3389-3395 (1991).
Alexander et al., "Analysis of effector mechanisms in murine cardiac allograft rejection" Transplant Immunology 4: 46-48 (1996).
Allen, et al., "CD40 ligand gene defects responsible for X-Linked Hyper-IgM Syndrome" Science, vol. 259, pp. 990-993 (1993).

Armitage, et al., "Molecular and biological characterization of a murine ligand for CD40", Nature, vol. 357, pp. 80-82, (1992).
Armour et al., "Differential binding to human FcyRIIa and FcyRIIB receptors by human IgG wildtype and mutant antibodies," Molecular Immunology, 40:585-593 (2003).
Armour et al., "Recombinant human IgG molecules lacking Fcy receptor I binding and monocyte triggering activities," Eur. J. Immunology, 29:2613-2624 (1999).
Aruffo, et al., "CD44 Is the Principal Cell Surface Receptor for Hyaluronate", Cell, vol. 61, pp. 1303-1313 (1990).
Aruffo, et al., "The CD40 ligand, gp39, is defective in activated T cells from patients with X-Linked Hyper-IgM Syndrome", Cell, vol. 72, pp. 291-300, (1993).
Attwood, "Genomics. The Babel of bioinformatics," Science, 290(5491):471-473 (2000).
Balint, "Antibody engineering by parsimonious mutagenesis," Gene, 137(1 ):109-118 (1993).
Barr, et al.,"Functional activity of CD40 antibodies correlates to the position of binding relative to CD154", Immunology, vol. 102, No. 1, pp. 39-43, Jan. 2001.
Barret al., "Functional activity of CD40 antibodies correlates to the position of binding relative to CD154," Immunology 102:39-43 (2001).
Bartlett, et al., "Cognate interactions between helper T cells and B cells", Journal of Immunology, vol. 145, No. 12, pp. 3956-3962 (1990).
Bastida-Corcuera et al., "Differential complement activation by bovine IgG2 allotypes," Veterinary Immunology and Immunopathology, vol. 71:115-123 (1999).
Biancone et al., "CD40-CD154 interaction in experimental and human disease (review)," Int. J. Mol. Med., 3:343-353 (1999).
Blair et al., "CD40 Ligand (CD154) Triggers a Short-Term CD4+ T Cell Activation Response That Results in Secretion of Immunomodulatory Cytokines and Apoptosis," The Journal of Experimental Medicine, 191(4):651-660 (2000).
Boyd, P.N., et al., "The Effect of the Removal of Sialic Acid, Galactose and Total Carbohydrate on the Functional Activity of Campath-1 H," Molecular Immunology, 32:1311-1318 (1995).
Brams et al., "A humanized anti-human CD154 monoclonal antibody blocks CD154-CD40 mediated human B cell activation," International Immunopharmacology 1:277-294 (2001).
Brekke et al., "Human IgG isotype-specific amino acid residues affecting complement-mediated cell lysis and phagocytosis," Eur. J. Immunology, 24:2542-2547 (1994).
Brorson et al.,"Mutational analysis of avidity and fine specificity of anti-levan antibodies," Journal of Immunolgy. 163:6694-6701 (1999).
Brummell et al., Probing the combining site of an anti-carbohydrate antibody by saturation-mutagenesis: role of the heavy-chain CDR3 residues, Biochemistry 32:1180-1187 (1993).
Buhlmann et al., "Therapeutic potential for blockade of the CD40 ligand, gp39," Journal of Clinical Immunology, 16 (2):83-89 (1996).
Bulmann et al., "In the absence of a CD40 signal, B cells are tolerogenic." Immunity 2: 645-653 (1995).
Burkly, "CD40 pathway blockade as an approach to immunotherapy", Advances in Experimental Medicine and Biology, 2001, vol. 489, pp. 135-152, 2001.
Burks et al., In vitro scanning saturation mutagenesis of an antibody binding pocket, PNAS 94:412-417 (1997).
Burton et al., "Immunoglobulin G: Functional Sites," Molecular Immunology, vol. 22(3):161-206 (1985).
Burton et al., "The C1q receptor site on immunoblobulin G." Nature, 288:338-344 (1980).
Canfield et al., "The Binding Affinity of Human IgG for its High Affinity Fc Receptor Is Determined by Multiple Amino Acids in the CH2 Domain and Is Modulated by the Hinge Region," J. Exp. Med., 173:1483-1491 (1991).
Carbone et al., "A new mechanism of NK cell cylotoxicity activation: The CD40-CD40 ligand interaction," Journal of Experimental Medicine, 185(12):2053-2060 (1997).
Caron et al., "Engineered Humanized Dimeric Forms of IgG Are More Effective Antibodies," J. of Exp. Med., 176:1191-1195 (1992).

(56) References Cited

OTHER PUBLICATIONS

Carter et al., "Humanization of an anti-p185"'"K' antibody for human cancer therapy," Proc. Nat/. Acad. Sci. USA, 89:4285-4289 (1992).

Carter et al., "Improved oligonucleotide site-directed rautagenesis using M13 vectors," Nucleic Acids Res., 13:4431-4443 (1985).

Caspit et al., "Improving the binding affinity of an antibody using molecular modeling and site-directed mutagenesis," Protein Science 7:1671-1680 (1998).

Casset et al. "A peptide mimetic of an anti-CD4 monoclonal antibody by rational design." BBRC 307, 198-2005, (2003).

Chan et al., "Variable region domain exchange in human IgGs promotes antibody complex formation with accompanying structural changes and altered effector functions," Molecular Immunology, vol. 41:527-538 (2004).

Chappel et al., "Identification of the Fey receptor class I binding site in human IgG through the use of recombinant IgG1/IgG2 hybrid and point-mutated antibodies," Proc. Natl. Acad. Sci. USA, vol. 88:9036-9040 (1991).

Chen et al. "Selection and analysis of an optimized anti-VEGF antibody: crystal structure of an affinity-matured Fab in complex with antigen" J. Mol. Bio. 293, 865-881 (1999).

Chirino et al., "Minimizing the immunogenicity of protein therapeutics," Drug Discovery Today, vol. 9(2):82-90 (2004).

Clark and Ledbetter, "How B and T cells talk to each other", Nature, vol. 367, pp. 425-428 (1994).

Cobbold, et al., "Monoclonal antibodies to promote marrow engraftment and tissue graft tolerance", Nature, vol. 323, pp. 164-166 (1986).

Cole et al., "HuM291, A Humanized Anti-CD3 Antibody, is Immunosuppressive to T Cells While Exhibiting Reduced Mitogenicity in Vitro," Transplantation, vol. 68(4):563-571 (1999).

Cole et al., "Human IgG2 Variants of Chimeric Anti-CD3 are Nonmitogenic to T Cells," The Journal of Immunology, 159:3613-3621 (1997).

Coleman, "Effects of amino acid sequence changes on antibody-antigen interactions", Research in Immunology 145:33-36 (1994).

Cordeiro et al. "Novel therapies in lupus—focus on nephritis" Acta Reumatol Port. 33(2):157-69, Apr.-Jun. 2008.

Daeron, "Fe Receptor Biology," Annu. Rev. Immunology, 15:203-234 (1997).

Dahiyat et al., "Protein design automation," Protein Science, vol. 5:895-903 (1996).

Daii-Acqua et al., "Modulation of the Effector Functions of a Human IgG1 through Engineering of Its Hinge Region," The Journal of Immunology, vol. 177:1129-1138 (2006).

Daley et al., "Fc-disabled anti-mouse CD40L antibodies retain efficacy in promoting transplantation tolerance," American Journal of Transplantation, 8(11):2265-2271 (2008).

De Pascalis et al., "Grafting of 'abbreviated' complementarity-determining regions containing specificity-determining residues essential for ligand contact to engineer a less immunogenic humanized monoclonal antibody",The Journal of Immunology 169, 3076-3084 (2002).

Dillman, "Monoclonal antibodies for treating Cancer", Annals of Internal Medicine, vol. 111, No. 7, pp. 592-603 (1989).

DiSanto, et al., "CD40 ligand mutations in X-linked immunodeficiency with hyper-IgM", Nature, vol. 361, pp. 541-543 (1993).

SEQUENCE LISTING

```
<160> NUMBER OF SEQ ID NOS: 59

<210> SEQ ID NO 1
<211> LENGTH: 111
<212> TYPE: PRT
<213> ORGANISM: Artificial Sequence
<220> FEATURE:
<223> OTHER INFORMATION: Description of Artificial Sequence: Synthetic
      wt 5c8 light chain variable region polypeptide

<400> SEQUENCE: 1

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
                20                  25                  30

Thr Tyr Ser Tyr Met His Trp Tyr Gln Gln Lys Pro Gly Gln Pro Pro
            35                  40                  45

Lys Leu Leu Ile Lys Tyr Ala Ser Asn Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
                100                 105                 110

<210> SEQ ID NO 2
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide mutant 5c8 light chain variable
      region
<220> FEATURE:
<221> NAME/KEY: CDS
<222> LOCATION: (1)..(333)
<220> FEATURE:
<221> NAME/KEY: modified_base
<222> LOCATION: (70)..(72)
<223> OTHER INFORMATION: a, c, t, g, unknown or other
<220> FEATURE:
<221> NAME/KEY: modified_base
<222> LOCATION: (76)..(84)
<223> OTHER INFORMATION: a, c, t, g, unknown or other
<220> FEATURE:
<221> NAME/KEY: modified_base
<222> LOCATION: (88)..(108)
<223> OTHER INFORMATION: a, c, t, g, unknown or other
<220> FEATURE:
<221> NAME/KEY: modified_base
```

```
<222> LOCATION: (112)..(114)
<223> OTHER INFORMATION: a, c, t, g, unknown or other
<220> FEATURE:
<221> NAME/KEY: modified_base
<222> LOCATION: (160)..(162)
<223> OTHER INFORMATION: a, c, t, g, unknown or other
<220> FEATURE:
<221> NAME/KEY: modified_base
<222> LOCATION: (169)..(180)
<223> OTHER INFORMATION: a, c, t, g, unknown or other
<220> FEATURE:
<221> NAME/KEY: modified_base
<222> LOCATION: (277)..(279)
<223> OTHER INFORMATION: a, c, t, g, unknown or other
<220> FEATURE:
<221> NAME/KEY: modified_base
<222> LOCATION: (283)..(294)
<223> OTHER INFORMATION: a, c, t, g, unknown or other
<220> FEATURE:
<221> NAME/KEY: modified_base
<222> LOCATION: (298)..(303)
<223> OTHER INFORMATION: a, c, t, g, unknown or other

<400> SEQUENCE: 2 gac atc gtt ctc aca cag tct cct gct acc tta tct gta tct ccg gga      48
Asp Ile Val Leu Thr Gln Ser Pro Ala Thr Leu Ser Val Ser Pro Gly
1               5                   10                  15 gag agg gcc acc atc tca tgc nnn gcc nnn nnn nnn gtc nnn nnn nnn      96
Glu Arg Ala Thr Ile Ser Cys Xaa Ala Xaa Xaa Xaa Val Xaa Xaa Xaa
            20                  25                  30 nnn nnn nnn nnn atg nnn tgg tac caa cag aaa cca gga cag cca ccc     144
Xaa Xaa Xaa Xaa Met Xaa Trp Tyr Gln Gln Lys Pro Gly Gln Pro Pro
                35                  40                  45 aaa ctc ctc atc aag nnn gca tcc nnn nnn nnn nnn ggg gtc cct gcc     192
Lys Leu Leu Ile Lys Xaa Ala Ser Xaa Xaa Xaa Xaa Gly Val Pro Ala
 50                  55                  60 agg ttc agt ggc agt ggg tct ggg act gac ttc acc ctc acc atc tct     240
Arg Phe Ser Gly Ser Gly Ser Gly Thr Asp Phe Thr Leu Thr Ile Ser
65                  70                  75                  80 tct gtg gag ccg gag gat ttt gca aca tat tac tgt nnn cac nnn nnn     288
Ser Val Glu Pro Glu Asp Phe Ala Thr Tyr Tyr Cys Xaa His Xaa Xaa
                85                  90                  95 nnn nnn cct nnn nnn ttc ggt cga ggg acc aag ctc gag att aag         333
Xaa Xaa Pro Xaa Xaa Phe Gly Arg Gly Thr Lys Leu Glu Ile Lys
            100                 105                 110

<210> SEQ ID NO 3
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide mutant 5c8 light chain variable
      region
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (26)..(28)
<223> OTHER INFORMATION: Any amino acid
<220> FEATURE:
<221> NAME/KEY: MOD_RES
<222> LOCATION: (30)..(36)
<223> OTHER INFORMATION: Any amino acid
<220> FEATURE:
<221> NAME/KEY: MOD_RES
<222> LOCATION: (38)..(38)
<223> OTHER INFORMATION: Any amino acid
<220> FEATURE:
```

```
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (57)..(60)
<223> OTHER INFORMATION: Any amino acid
<220> FEATURE:
<221> NAME/KEY: MOD_RES
<222> LOCATION: (93)..(93)
<223> OTHER INFORMATION: Any amino acid
<220> FEATURE:
<221> NAME/KEY: MOD_RES
<222> LOCATION: (95)..(98)
<223> OTHER INFORMATION: Any amino acid
<220> FEATURE:
<221> NAME/KEY: MOD_RES
<222> LOCATION: (100)..(101)
<223> OTHER INFORMATION: Any amino acid

<400> SEQUENCE: 3

Asp Ile Val Leu Thr Gln Ser Pro Ala Thr Leu Ser Val Ser Pro Gly
1               5                   10                  15

Glu Arg Ala Thr Ile Ser Cys Xaa Ala Xaa Xaa Xaa Val Xaa Xaa Xaa
            20                  25                  30

Xaa Xaa Xaa Xaa Met Xaa Trp Tyr Gln Gln Lys Pro Gly Gln Pro Pro
        35                  40                  45

Lys Leu Leu Ile Lys Xaa Ala Ser Xaa Xaa Xaa Gly Val Pro Ala
 50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Xaa His Xaa Xaa
                85                  90                  95

Xaa Xaa Pro Xaa Xaa Phe Gly Gly Gly Thr Lys Leu Glu Ile Lys
            100                 105                 110

<210> SEQ ID NO 4
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide wt 5c8 heavy chain variable region

<400> SEQUENCE: 4

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
 50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
        115
```

<210> SEQ ID NO 5
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide mutant 5c8 heavy chain variable region
<220> FEATURE:
<221> NAME/KEY: CDS
<222> LOCATION: (1)..(354)
<220> FEATURE:
<221> NAME/KEY: modified_base
<222> LOCATION: (82)..(84)
<223> OTHER INFORMATION: a, c, t, g, unknown or other
<220> FEATURE:
<221> NAME/KEY: modified_base
<222> LOCATION: (88)..(99)
<223> OTHER INFORMATION: a, c, t, g, unknown or other
<220> FEATURE:
<221> NAME/KEY: modified_base
<222> LOCATION: (103)..(105)
<223> OTHER INFORMATION: a, c, t, g, unknown or other
<220> FEATURE:
<221> NAME/KEY: modified_base
<222> LOCATION: (148)..(150)
<223> OTHER INFORMATION: a, c, t, g, unknown or other
<220> FEATURE:
<221> NAME/KEY: modified_base
<222> LOCATION: (154)..(165)
<223> OTHER INFORMATION: a, c, t, g, unknown or other
<220> FEATURE:
<221> NAME/KEY: modified_base
<222> LOCATION: (169)..(198)
<223> OTHER INFORMATION: a, c, t, g, unknown or other
<220> FEATURE:
<221> NAME/KEY: modified_base
<222> LOCATION: (295)..(321)
<223> OTHER INFORMATION: a, c, t, g, unknown or other

<400> SEQUENCE: 5

```
cag gtt cag ctg gtg cag tca ggg gct gaa gtg gtg aag cct ggg gct      48
Gln Val Gln Leu Val Gln Ser Gly Ala Glu Val Val Lys Pro Gly Ala
1               5                   10                  15 tca gtg aag ttg tcc tgc aag gct tct ggc tac nnn ttc nnn nnn nnn      96
Ser Val Lys Leu Ser Cys Lys Ala Ser Gly Tyr Xaa Phe Xaa Xaa Xaa
            20                  25                  30 nnn atg nnn tgg gtg aag cag gcg ccc gga caa ggc ctt gag tgg att     144
Xaa Met Xaa Trp Val Lys Gln Ala Pro Gly Gln Gly Leu Glu Trp Ile
        35                  40                  45 gga nnn att nnn nnn nnn nnn ggt nnn nnn nnn nnn nnn nnn nnn nnn     192
Gly Xaa Ile Xaa Xaa Xaa Xaa Gly Xaa Xaa Xaa Xaa Xaa Xaa Xaa Xaa
50                  55                  60 nnn nnn aag gcc aca ctg act gta gac aaa tcc gcc agc aca gca tac     240
Xaa Xaa Lys Ala Thr Leu Thr Val Asp Lys Ser Ala Ser Thr Ala Tyr
65                  70                  75                  80 atg gag ctc agc agc ctg acg tct gag gac act gcg gtc tat tac tgt     288
Met Glu Leu Ser Ser Leu Thr Ser Glu Asp Thr Ala Val Tyr Tyr Cys
                85                  90                  95 aca aga nnn nnn nnn nnn nnn nnn nnn nnn tgg ggc caa ggg acc         336
Thr Arg Xaa Xaa Xaa Xaa Xaa Xaa Xaa Xaa Trp Gly Gln Gly Thr
            100                 105                 110 ctg gtc acc gtc tcc tca                                             354
Leu Val Thr Val Ser Ser
        115
```

<210> SEQ ID NO 6
<211> LENGTH: 118
<212> TYPE: PRT
<213> ORGANISM: Artificial Sequence

```
<220> FEATURE:
<223> OTHER INFORMATION: Description of Artificial Sequence: Synthetic
      polypeptide mutant 5c8 heavy chain variable
      region
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (30)..(33)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (50)..(50)
<223> OTHER INFORMATION: Any amino acid
<220> FEATURE:
<221> NAME/KEY: MOD_RES
<222> LOCATION: (52)..(55)
<223> OTHER INFORMATION: Any amino acid
<220> FEATURE:
<221> NAME/KEY: MOD_RES
<222> LOCATION: (57)..(66)
<223> OTHER INFORMATION: Any amino acid
<220> FEATURE:
<221> NAME/KEY: MOD_RES
<222> LOCATION: (99)..(107)
<223> OTHER INFORMATION: Any amino acid

<400> SEQUENCE: 6

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Xaa Phe Xaa Xaa Xaa
            20                  25                  30

Xaa Met Xaa Trp Val Lys Gln Ala Pro Gly Gln Gly Leu Glu Trp Ile
        35                  40                  45

Gly Xaa Ile Xaa Xaa Xaa Xaa Gly Xaa Xaa Xaa Xaa Xaa Xaa Xaa Xaa
    50                  55                  60

Xaa Xaa Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Xaa Xaa Xaa Xaa Xaa Xaa Xaa Xaa Trp Gly Gln Gly Thr
            100                 105                 110

Leu Val Thr Val Ser Ser
        115

<210> SEQ ID NO 7
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Arg, Asn, Cys, Gln, Gly, His, Met, Phe, Ser,
      Thr, Trp, Tyr, Ala, Ile, Leu, Pro, Val, Asp, Glu or Lys
<220> FEATURE:
<221> NAME/KEY: MOD_RES
<222> LOCATION: (26)..(26)
<223> OTHER INFORMATION: Ser, Asn, Cys, Gln, Gly, His, Met, Phe, Thr,
      Trp, Tyr, Ala, Ile, Leu, Pro, Val, Asp or Glu
<220> FEATURE:
<221> NAME/KEY: MOD_RES
```

```
<222> LOCATION: (27)..(27)
<223> OTHER INFORMATION: Gln, Asn, Cys, Gly, His, Met, Phe, Ser, Thr,
      Trp, Tyr, Asp, Glu, Arg or Lys
<220> FEATURE:
<221> NAME/KEY: MOD_RES
<222> LOCATION: (28)..(28)
<223> OTHER INFORMATION: Arg, Asn, Cys, Gln, Gly, His, Met, Phe, Ser,
      Thr, Trp, Tyr, Asp, Glu, Ala, Ile, Leu, Pro or Val
<220> FEATURE:
<221> NAME/KEY: MOD_RES
<222> LOCATION: (30)..(30)
<223> OTHER INFORMATION: Ser, Asn, Cys, Gln, Gly, His, Met, Phe, Thr,
      Trp, Tyr, Asp, Glu, Arg or Lys
<220> FEATURE:
<221> NAME/KEY: MOD_RES
<222> LOCATION: (31)..(31)
<223> OTHER INFORMATION: Ser, Asn, Cys, Gln, Gly, His, Met, Phe, Thr,
      Trp, Tyr, Ala, Ile, Leu, Pro, Val, Arg or Lys
<220> FEATURE:
<221> NAME/KEY: MOD_RES
<222> LOCATION: (32)..(32)
<223> OTHER INFORMATION: Ser, Asn, Cys, Gln, Gly, His, Met, Phe, Thr,
      Trp, Tyr, Arg, Ala, Ile, Leu or Lys
<220> FEATURE:
<221> NAME/KEY: MOD_RES
<222> LOCATION: (33)..(33)
<223> OTHER INFORMATION: Thr, Asn, Cys, Gln, Gly, His, Met, Phe, Ser,
      Trp, Tyr, Asp, Glu, Arg, Ala, Val or Lys
<220> FEATURE:
<221> NAME/KEY: MOD_RES
<222> LOCATION: (34)..(34)
<223> OTHER INFORMATION: Tyr, Asn, Cys, Gln, Gly, His, Met, Phe, Ser,
      Thr, Trp, Ala, Ile, Leu, Pro, Val, Asp, Glu, Arg or Lys
<220> FEATURE:
<221> NAME/KEY: MOD_RES
<222> LOCATION: (35)..(35)
<223> OTHER INFORMATION: Ser, Asn, Cys, Gln, Gly, His, Met, Phe, Thr,
      Trp or Tyr
<220> FEATURE:
<221> NAME/KEY: MOD_RES
<222> LOCATION: (36)..(36)
<223> OTHER INFORMATION: Tyr, Asn, Cys, Gln, Gly, His, Met, Phe, Ser,
      Thr, Trp, Asp, Ala, Leu or Glu
<220> FEATURE:
<221> NAME/KEY: MOD_RES
<222> LOCATION: (38)..(38)
<223> OTHER INFORMATION: His, Asn, Cys, Gln, Gly, Met, Phe, Ser, Thr,
      Trp, Tyr, Ala, Ile, Leu, Pro, Val, Asp, Glu, Arg or Lys
<220> FEATURE:
<221> NAME/KEY: MOD_RES
<222> LOCATION: (54)..(54)
<223> OTHER INFORMATION: Tyr, Asn, Cys, Gln, Gly, His, Met, Phe, Ser,
      Thr, Trp, Ala, Ile, Leu, Pro, Val, Asp or Glu
<220> FEATURE:
<221> NAME/KEY: MOD_RES
<222> LOCATION: (57)..(57)
<223> OTHER INFORMATION: Asn, Cys, Gln, Gly, His, Met, Phe, Ser, Thr,
      Trp, Tyr, Asp or Glu
<220> FEATURE:
<221> NAME/KEY: MOD_RES
<222> LOCATION: (58)..(58)
<223> OTHER INFORMATION: Leu, Asn, Cys, Gln, Gly, His, Met, Phe, Ser,
      Thr, Trp, Asp or Glu
<220> FEATURE:
<221> NAME/KEY: MOD_RES
<222> LOCATION: (59)..(59)
<223> OTHER INFORMATION: Glu, Asn, Cys, Gln, Gly, His, Met, Phe, Ser,
      Thr, Trp, Tyr or Asp
<220> FEATURE:
<221> NAME/KEY: MOD_RES
<222> LOCATION: (60)..(60)
<223> OTHER INFORMATION: Ser, Asp or Glu
<220> FEATURE:
<221> NAME/KEY: MOD_RES
<222> LOCATION: (93)..(93)
<223> OTHER INFORMATION: Gln, Asn, Cys, Gly, His, Met, Phe, Ser, Thr,
      Trp, Tyr, Ala, Ile, Leu, Pro, Val, Asp, Glu, Arg or Lys
<220> FEATURE:
<221> NAME/KEY: MOD_RES
```

```
<222> LOCATION: (95)..(95)
<223> OTHER INFORMATION: Ser, Asn, Cys, Gln, Gly, His, Met, Phe, Thr,
      Trp, Tyr, Asp or Glu
<220> FEATURE:
<221> NAME/KEY: MOD_RES
<222> LOCATION: (96)..(96)
<223> OTHER INFORMATION: Trp, Asn, Cys, Gln, Gly, His, Met, Phe, Ser,
      Thr, Tyr, Asp, Glu, Arg or Lys
<220> FEATURE:
<221> NAME/KEY: MOD_RES
<222> LOCATION: (97)..(97)
<223> OTHER INFORMATION: Glu or Asp
<220> FEATURE:
<221> NAME/KEY: MOD_RES
<222> LOCATION: (98)..(98)
<223> OTHER INFORMATION: Ile, Asn, Cys, Gln, Gly, His, Met, Phe, Ser,
      Thr, Trp, Tyr, Asp, Ala, Leu, Pro, Val or Glu
<220> FEATURE:
<221> NAME/KEY: MOD_RES
<222> LOCATION: (100)..(100)
<223> OTHER INFORMATION: Pro, Asn, Cys, Gln, Gly, His, Met, Phe, Ser,
      Thr, Trp, Tyr, Asp or Glu
<220> FEATURE:
<221> NAME/KEY: MOD_RES
<222> LOCATION: (101)..(101)
<223> OTHER INFORMATION: Thr, Asn, Cys, Gln, Gly, His, Met, Phe, Ser,
      Trp, Tyr, Ala, Ile, Leu, Pro, Val, Asp or Glu

<400> SEQUENCE: 7

Asp Ile Val Leu Thr Gln Ser Pro Ala Thr Leu Ser Val Ser Pro Gly
1               5                   10                  15

Glu Arg Ala Thr Ile Ser Cys Xaa Ala Xaa Xaa Xaa Val Xaa Xaa Xaa
            20                  25                  30

Xaa Xaa Xaa Xaa Met Xaa Trp Tyr Gln Gln Lys Pro Gly Gln Pro Pro
        35                  40                  45

Lys Leu Leu Ile Lys Xaa Ala Ser Xaa Xaa Xaa Gly Val Pro Ala
50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Xaa His Xaa Xaa
                85                  90                  95

Xaa Xaa Pro Xaa Xaa Phe Gly Gly Gly Thr Lys Leu Glu Ile Lys
            100                 105                 110

<210> SEQ ID NO 8
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (26)..(26)
<223> OTHER INFORMATION: Ser or Asp
<220> FEATURE:
<221> NAME/KEY: MOD_RES
<222> LOCATION: (27)..(27)
<223> OTHER INFORMATION: Gln or Glu
<220> FEATURE:
<221> NAME/KEY: MOD_RES
<222> LOCATION: (28)..(28)
<223> OTHER INFORMATION: Arg or Glu
<220> FEATURE:
<221> NAME/KEY: MOD_RES
<222> LOCATION: (30)..(30)
<223> OTHER INFORMATION: Any amino acid
```

```
<220> FEATURE:
<221> NAME/KEY: MOD_RES
<222> LOCATION: (31)..(31)
<223> OTHER INFORMATION: Ser, Ala, His, Asn, Thr, Val or Trp
<220> FEATURE:
<221> NAME/KEY: MOD_RES
<222> LOCATION: (32)..(32)
<223> OTHER INFORMATION: Ser, Ala, Phe, Ile, Leu, Met or Trp
<220> FEATURE:
<221> NAME/KEY: MOD_RES
<222> LOCATION: (33)..(33)
<223> OTHER INFORMATION: Thr, Ala, Phe, Met, Val, Trp, Asp, Arg, Tyr or
      Gln
<220> FEATURE:
<221> NAME/KEY: MOD_RES
<222> LOCATION: (34)..(34)
<223> OTHER INFORMATION: Tyr, Ala, Asp, Glu, Phe, Ile, Lys, Leu, Met,
      Arg, Val or Trp
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (36)..(36)
<223> OTHER INFORMATION: Tyr, Ala, Phe, Leu or Trp
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (54)..(54)
<223> OTHER INFORMATION: Tyr or Glu
<220> FEATURE:
<221> NAME/KEY: MOD_RES
<222> LOCATION: (57)..(60)
<223> OTHER INFORMATION: Any amino acid
<220> FEATURE:
<221> NAME/KEY: MOD_RES
<222> LOCATION: (93)..(93)
<223> OTHER INFORMATION: Any amino acid
<220> FEATURE:
<221> NAME/KEY: MOD_RES
<222> LOCATION: (95)..(95)
<223> OTHER INFORMATION: Any amino acid
<220> FEATURE:
<221> NAME/KEY: MOD_RES
<222> LOCATION: (96)..(96)
<223> OTHER INFORMATION: Trp, Asp, Glu, His, Arg, Ser or Thr
<220> FEATURE:
<221> NAME/KEY: MOD_RES
<222> LOCATION: (97)..(97)
<223> OTHER INFORMATION: Any amino acid
<220> FEATURE:
<221> NAME/KEY: MOD_RES
<222> LOCATION: (98)..(98)
<223> OTHER INFORMATION: Ile, Ala, Phe, His, Leu, Met, Asn, Pro, Gln,
      Ser, Thr, Val, Trp or Tyr
<220> FEATURE:
<221> NAME/KEY: MOD_RES
<222> LOCATION: (100)..(101)
<223> OTHER INFORMATION: Any amino acid

<400> SEQUENCE: 8

Asp Ile Val Leu Thr Gln Ser Pro Ala Thr Leu Ser Val Ser Pro Gly
1               5                   10                  15

Glu Arg Ala Thr Ile Ser Cys Xaa Ala Xaa Xaa Xaa Val Xaa Xaa Xaa
            20                  25                  30

Xaa Xaa Xaa Xaa Met Xaa Trp Tyr Gln Gln Lys Pro Gly Gln Pro Pro
        35                  40                  45

Lys Leu Leu Ile Lys Xaa Ala Ser Xaa Xaa Xaa Gly Val Pro Ala
50                  55                  60

Arg Phe Ser Gly Ser Gly Ser Gly Thr Asp Phe Thr Leu Thr Ile Ser
```

```
                        65                  70                  75                  80
Ser Val Glu Pro Glu Asp Phe Ala Thr Tyr Tyr Cys Xaa His Xaa Xaa
                    85                  90                  95

Xaa Xaa Pro Xaa Xaa Phe Gly Gly Gly Thr Lys Leu Glu Ile Lys
                100                 105                 110

<210> SEQ ID NO 9
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Ser, Asp or Glu
<220> FEATURE:
<221> NAME/KEY: MOD_RES
<222> LOCATION: (27)..(27)
<223> OTHER INFORMATION: Gln, Asp or Glu
<220> FEATURE:
<221> NAME/KEY: MOD_RES
<222> LOCATION: (31)..(31)
<223> OTHER INFORMATION: Ser, Asn, Cys, Gln, Gly, Thr or Tyr
<220> FEATURE:
<221> NAME/KEY: MOD_RES
<222> LOCATION: (32)..(32)
<223> OTHER INFORMATION: Ser, Ala, Ile, Leu, Met, Phe, Pro, Val or Trp
<220> FEATURE:
<221> NAME/KEY: MOD_RES
<222> LOCATION: (33)..(33)
<223> OTHER INFORMATION: Thr, Asn, Cys, Gln, Gly, Ser or Tyr
<220> FEATURE:
<221> NAME/KEY: MOD_RES
<222> LOCATION: (98)..(98)
<223> OTHER INFORMATION: Ile, Asn, Cys, Gln, Gly, Ser, Thr or Tyr

<400> SEQUENCE: 9

Asp Ile Val Leu Thr Gln Ser Pro Ala Thr Leu Ser Val Ser Pro Gly
1               5                   10                  15

Glu Arg Ala Thr Ile Ser Cys Arg Ala Xaa Xaa Arg Val Ser Xaa Xaa
                20                  25                  30

Xaa Tyr Ser Tyr Met His Trp Tyr Gln Gln Lys Pro Gly Gln Pro Pro
            35                  40                  45

Lys Leu Leu Ile Lys Tyr Ala Ser Asn Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Xaa Pro Pro Thr Phe Gly Gly Gly Thr Lys Leu Glu Ile Lys
                100                 105                 110

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (30)..(30)
```

-continued

```
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (33)..(33)
<223> OTHER INFORMATION: Asp or Arg
<220> FEATURE:
<221> NAME/KEY: MOD_RES
<222> LOCATION: (34)..(36)
<223> OTHER INFORMATION: Any amino acid
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (57)..(60)
<223> OTHER INFORMATION: Any amino acid
<220> FEATURE:
<221> NAME/KEY: MOD_RES
<222> LOCATION: (93)..(93)
<223> OTHER INFORMATION: Any amino acid
<220> FEATURE:
<221> NAME/KEY: MOD_RES
<222> LOCATION: (95)..(98)
<223> OTHER INFORMATION: Any amino acid
<220> FEATURE:
<221> NAME/KEY: MOD_RES
<222> LOCATION: (100)..(101)
<223> OTHER INFORMATION: Any amino acid

<400> SEQUENCE: 10

Asp Ile Val Leu Thr Gln Ser Pro Ala Thr Leu Ser Val Ser Pro Gly
1               5                   10                  15

Glu Arg Ala Thr Ile Ser Cys Xaa Ala Asp Glu Glu Val Xaa Val Xaa
            20                  25                  30

Xaa Xaa Xaa Xaa Met Xaa Trp Tyr Gln Gln Lys Pro Gly Gln Pro Pro
        35                  40                  45

Lys Leu Leu Ile Lys Glu Ala Ser Xaa Xaa Xaa Xaa Gly Val Pro Ala
50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Xaa His Xaa Xaa
                85                  90                  95

Xaa Xaa Pro Xaa Xaa Phe Gly Gly Gly Thr Lys Leu Glu Ile Lys
            100                 105                 110

<210> SEQ ID NO 11
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (26)..(28)
<223> OTHER INFORMATION: Any amino acid
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
```

```
<222> LOCATION: (31)..(31)
<223> OTHER INFORMATION: His or Asn
<220> FEATURE:
<221> NAME/KEY: MOD_RES
<222> LOCATION: (32)..(32)
<223> OTHER INFORMATION: Trp or Phe
<220> FEATURE:
<221> NAME/KEY: MOD_RES
<222> LOCATION: (33)..(33)
<223> OTHER INFORMATION: Trp, Tyr or Gln
<220> FEATURE:
<221> NAME/KEY: MOD_RES
<222> LOCATION: (34)..(35)
<223> OTHER INFORMATION: Any amino acid
<220> FEATURE:
<221> NAME/KEY: MOD_RES
<222> LOCATION: (36)..(36)
<223> OTHER INFORMATION: Leu or Trp
<220> FEATURE:
<221> NAME/KEY: MOD_RES
<222> LOCATION: (38)..(38)
<223> OTHER INFORMATION: Any amino acid
<220> FEATURE:
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (57)..(60)
<223> OTHER INFORMATION: Any amino acid
<220> FEATURE:
<221> NAME/KEY: MOD_RES
<222> LOCATION: (93)..(93)
<223> OTHER INFORMATION: Any amino acid
<220> FEATURE:
<221> NAME/KEY: MOD_RES
<222> LOCATION: (95)..(95)
<223> OTHER INFORMATION: Any amino acid
<220> FEATURE:
<221> NAME/KEY: MOD_RES
<222> LOCATION: (97)..(97)
<223> OTHER INFORMATION: Any amino acid
<220> FEATURE:
<221> NAME/KEY: MOD_RES
<222> LOCATION: (98)..(98)
<223> OTHER INFORMATION: Phe or Gln
<220> FEATURE:
<221> NAME/KEY: MOD_RES
<222> LOCATION: (100)..(101)
<223> OTHER INFORMATION: Any amino acid

<400> SEQUENCE: 11

Asp Ile Val Leu Thr Gln Ser Pro Ala Thr Leu Ser Val Ser Pro Gly
1               5                   10                  15

Glu Arg Ala Thr Ile Ser Cys Xaa Ala Xaa Xaa Xaa Val Xaa Xaa Xaa
            20                  25                  30

Xaa Xaa Xaa Xaa Met Xaa Trp Tyr Gln Gln Lys Pro Gly Gln Pro Pro
        35                  40                  45

Lys Leu Leu Ile Lys Xaa Ala Ser Xaa Xaa Xaa Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Xaa His Xaa His
                85                  90                  95

Xaa Xaa Pro Xaa Xaa Phe Gly Gly Gly Thr Lys Leu Glu Ile Lys
            100                 105                 110

<210> SEQ ID NO 12
<211> LENGTH: 111
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Ser or Asp
<220> FEATURE:
<221> NAME/KEY: MOD_RES
<222> LOCATION: (27)..(27)
<223> OTHER INFORMATION: Gln or Glu
<220> FEATURE:
<221> NAME/KEY: MOD_RES
<222> LOCATION: (31)..(31)
<223> OTHER INFORMATION: Ser or Asn
<220> FEATURE:
<221> NAME/KEY: MOD_RES
<222> LOCATION: (32)..(32)
<223> OTHER INFORMATION: Ser or Phe
<220> FEATURE:
<221> NAME/KEY: MOD_RES
<222> LOCATION: (33)..(33)
<223> OTHER INFORMATION: Thr, Gln or Tyr
<220> FEATURE:
<221> NAME/KEY: MOD_RES
<222> LOCATION: (98)..(98)
<223> OTHER INFORMATION: Ile or Gln

<400> SEQUENCE: 12

Asp Ile Val Leu Thr Gln Ser Pro Ala Thr Leu Ser Val Ser Pro Gly
1               5                   10                  15

Glu Arg Ala Thr Ile Ser Cys Arg Ala Xaa Xaa Arg Val Ser Xaa Xaa
            20                  25                  30

Xaa Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Xaa Pro Pro Thr Phe Gly Gly Gly Thr Lys Leu Glu Ile Lys
            100                 105                 110

<210> SEQ ID NO 13
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Val Leu Thr Gln Ser Pro Ala Thr Leu Ser Val Ser Pro Gly
1               5                   10                  15

Glu Arg Ala Thr Ile Ser Cys Arg Ala Asp Gln Arg Val Ser Ser Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95
```

```
Glu Ile Pro Pro Thr Phe Gly Gly Gly Thr Lys Leu Glu Ile Lys
            100                 105                 110
```

<210> SEQ ID NO 14
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Asp Ile Val Leu Thr Gln Ser Pro Ala Thr Leu Ser Val Ser Pro Gly
1               5                   10                  15

Glu Arg Ala Thr Ile Ser Cys Arg Ala Ser Glu Arg Val Ser Ser Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110
```

<210> SEQ ID NO 15
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Asn Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110
```

<210> SEQ ID NO 16
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Phe
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110
```

<210> SEQ ID NO 17
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
            20                  25                  30

Gln Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110
```

<210> SEQ ID NO 18
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
            20                  25                  30

Tyr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80
```

```
Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110
```

<210> SEQ ID NO 19
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
                20                  25                  30

Thr Tyr Ser Tyr Met His Trp Tyr Gln Gln Lys Pro Gly Gln Pro Pro
            35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Gln Pro Pro Thr Phe Gly Gly Gly Thr Lys Leu Glu Ile Lys
            100                 105                 110
```

<210> SEQ ID NO 20
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Asp Ile Val Leu Thr Gln Ser Pro Ala Thr Leu Ser Val Ser Pro Gly
1               5                   10                  15

Glu Arg Ala Thr Ile Ser Cys Arg Ala Asp Glu Arg Val Ser Ser Ser
                20                  25                  30

Thr Tyr Ser Tyr Met His Trp Tyr Gln Gln Lys Pro Gly Gln Pro Pro
            35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110
```

<210> SEQ ID NO 21
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 21

Asp Ile Val Leu Thr Gln Ser Pro Ala Thr Leu Ser Val Ser Pro Gly
1               5                   10                  15

Glu Arg Ala Thr Ile Ser Cys Arg Ala Asp Glu Arg Val Ser Asn Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110

<210> SEQ ID NO 22
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Val Leu Thr Gln Ser Pro Ala Thr Leu Ser Val Ser Pro Gly
1               5                   10                  15

Glu Arg Ala Thr Ile Ser Cys Arg Ala Asp Glu Arg Val Ser Ser Phe
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110

<210> SEQ ID NO 23
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Val Leu Thr Gln Ser Pro Ala Thr Leu Ser Val Ser Pro Gly
1               5                   10                  15

Glu Arg Ala Thr Ile Ser Cys Arg Ala Asp Glu Arg Val Ser Ser Ser
            20                  25                  30

Gln Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
```

```
            65                  70                  75                  80
Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110

<210> SEQ ID NO 24
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Val Leu Thr Gln Ser Pro Ala Thr Leu Ser Val Ser Pro Gly
1               5                   10                  15

Glu Arg Ala Thr Ile Ser Cys Arg Ala Asp Glu Arg Val Ser Ser Ser
            20                  25                  30

Tyr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110

<210> SEQ ID NO 25
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Val Leu Thr Gln Ser Pro Ala Thr Leu Ser Val Ser Pro Gly
1               5                   10                  15

Glu Arg Ala Thr Ile Ser Cys Arg Ala Asp Glu Arg Val Ser Ser Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Gln Pro Pro Thr Phe Gly Gly Gly Thr Lys Leu Glu Ile Lys
            100                 105                 110

<210> SEQ ID NO 26
<211> LENGTH: 111
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 26

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
            20                  25                  30

Thr Tyr Ser Trp Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110

<210> SEQ ID NO 27
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
            20                  25                  30

Trp Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110

<210> SEQ ID NO 28
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Val Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

```
Arg Phe Ser Gly Ser Gly Ser Gly Thr Asp Phe Thr Leu Thr Ile Ser
 65                  70                  75                  80

Ser Val Glu Pro Glu Asp Phe Ala Thr Tyr Tyr Cys Gln His Ser Trp
                 85                  90                  95

Glu Ile Pro Pro Thr Phe Gly Gly Gly Thr Lys Leu Glu Ile Lys
            100                 105                 110

<210> SEQ ID NO 29
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Val Leu Thr Gln Ser Pro Ala Thr Leu Ser Val Ser Pro Gly
  1               5                  10                  15

Glu Arg Ala Thr Ile Ser Cys Arg Ala Ser Gln Arg Val Ser Ser Ser
                 20                  25                  30

Asp Tyr Ser Tyr Met His Trp Tyr Gln Gln Lys Pro Gly Gln Pro Pro
             35                  40                  45

Lys Leu Leu Ile Lys Tyr Ala Ser Asn Leu Glu Ser Gly Val Pro Ala
         50                  55                  60

Arg Phe Ser Gly Ser Gly Ser Gly Thr Asp Phe Thr Leu Thr Ile Ser
 65                  70                  75                  80

Ser Val Glu Pro Glu Asp Phe Ala Thr Tyr Tyr Cys Gln His Ser Trp
                 85                  90                  95

Glu Ile Pro Pro Thr Phe Gly Gly Gly Thr Lys Leu Glu Ile Lys
            100                 105                 110

<210> SEQ ID NO 30
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Val Leu Thr Gln Ser Pro Ala Thr Leu Ser Val Ser Pro Gly
  1               5                  10                  15

Glu Arg Ala Thr Ile Ser Cys Arg Ala Ser Gln Arg Val Ser Ser Ser
                 20                  25                  30

Thr Tyr Ser Tyr Met His Trp Tyr Gln Gln Lys Pro Gly Gln Pro Pro
             35                  40                  45

Lys Leu Leu Ile Lys Glu Ala Ser Asn Leu Glu Ser Gly Val Pro Ala
         50                  55                  60

Arg Phe Ser Gly Ser Gly Ser Gly Thr Asp Phe Thr Leu Thr Ile Ser
 65                  70                  75                  80

Ser Val Glu Pro Glu Asp Phe Ala Thr Tyr Tyr Cys Gln His Ser Trp
                 85                  90                  95

Glu Ile Pro Pro Thr Phe Gly Gly Gly Thr Lys Leu Glu Ile Lys
            100                 105                 110

<210> SEQ ID NO 31
<211> LENGTH: 111
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 31

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110

<210> SEQ ID NO 32
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Val Leu Thr Gln Ser Pro Ala Thr Leu Ser Val Ser Pro Gly
1               5                   10                  15

Glu Arg Ala Thr Ile Ser Cys Arg Ala Asp Gln Arg Val Ser Ser Ser
            20                  25                  30

Trp Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys
            100                 105                 110

<210> SEQ ID NO 33
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Ile, Asp, Glu, Arg, Lys, Asn, Cys, Gln, Gly,
      His, Met, Phe, Ser, Thr or Trp
<220> FEATURE:
<221> NAME/KEY: MOD_RES
<222> LOCATION: (30)..(30)
<223> OTHER INFORMATION: Thr, Asp, Glu, Arg, Lys, Asn, Cys, Gln, Gly,
      His, Met, Phe, Trp, Tyr, Ala, Ile, Leu, Pro or Val
<220> FEATURE:
<221> NAME/KEY: MOD_RES

```
<222> LOCATION: (31)..(31)
<223> OTHER INFORMATION: Ser, Arg, His, Lys, Gln or Trp
<220> FEATURE:
<221> NAME/KEY: MOD_RES
<222> LOCATION: (32)..(32)
<223> OTHER INFORMATION: Tyr, Asp, Glu, Arg, Lys, Asn, Cys, Gln, Gly,
      His, Met, Phe, Ser, Trp, Ala, Ile, Leu, Pro or Val
<220> FEATURE:
<221> NAME/KEY: MOD_RES
<222> LOCATION: (33)..(33)
<223> OTHER INFORMATION: Tyr, Asp, Glu, Asn, Cys, Gln, Gly, His, Met,
      Phe, Ser, Thr, Trp Ala, Ile, Leu, Pro or Val
<220> FEATURE:
<221> NAME/KEY: MOD_RES
<222> LOCATION: (35)..(35)
<223> OTHER INFORMATION: Tyr, Asn, Cys, Gln, Gly, His, Met, Phe, Ser,
      Thr, Trp, Asp or Glu
<220> FEATURE:
<221> NAME/KEY: MOD_RES
<222> LOCATION: (50)..(50)
<223> OTHER INFORMATION: Glu or Asp
<220> FEATURE:
<221> NAME/KEY: MOD_RES
<222> LOCATION: (52)..(52)
<223> OTHER INFORMATION: Asn, Cys, Gln, Gly, His, Met, Phe, Ser, Thr,
      Trp, Tyr, Arg, Ala, Leu, Val or Lys
<220> FEATURE:
<221> NAME/KEY: MOD_RES
<222> LOCATION: (53)..(53)
<223> OTHER INFORMATION: Pro, Asn, Cys, Gln, Gly, His, Met, Phe, Ser,
      Thr, Trp, Tyr, Asp or Glu
<220> FEATURE:
<221> NAME/KEY: MOD_RES
<222> LOCATION: (54)..(54)
<223> OTHER INFORMATION: Ser, Asn, Cys, Gln, Gly, His, Met, Phe, Thr,
      Trp, Tyr, Arg, Lys or Glu
<220> FEATURE:
<221> NAME/KEY: MOD_RES
<222> LOCATION: (55)..(55)
<223> OTHER INFORMATION: Asn, Glu, Lys, Gln, Ser, Thr, Met or Val
<220> FEATURE:
<221> NAME/KEY: MOD_RES
<222> LOCATION: (57)..(57)
<223> OTHER INFORMATION: Asp, Glu, Phe or Leu
<220> FEATURE:
<221> NAME/KEY: MOD_RES
<222> LOCATION: (58)..(58)
<223> OTHER INFORMATION: Thr, Asn, Cys, Gln, Gly, His, Met, Phe, Ser,
      Trp, Tyr, Ala, Ile, Leu, Pro or Val
<220> FEATURE:
<221> NAME/KEY: MOD_RES
<222> LOCATION: (59)..(59)
<223> OTHER INFORMATION: Asn, Cys, Gln, Gly, His, Met, Phe, Ser, Thr,
      Trp, Tyr, Ala, Ile, Leu, Pro, Val, Asp or Glu
<220> FEATURE:
<221> NAME/KEY: MOD_RES
<222> LOCATION: (60)..(60)
<223> OTHER INFORMATION: Phe, Asp, Asn, Cys, Gln, Gly, His, Met, Ser,
      Thr, Trp, Tyr, Glu, Arg, Lys, Ala, Ile, Leu, Pro or Val
<220> FEATURE:
<221> NAME/KEY: MOD_RES
<222> LOCATION: (61)..(61)
<223> OTHER INFORMATION: Asn, Asp or Glu
<220> FEATURE:
<221> NAME/KEY: MOD_RES
<222> LOCATION: (62)..(62)
<223> OTHER INFORMATION: Glu or Asp
<220> FEATURE:
<221> NAME/KEY: MOD_RES
<222> LOCATION: (63)..(63)
<223> OTHER INFORMATION: Lys, Asn, Cys, Gln, Gly, His, Met, Phe, Ser,
      Thr, Trp, Tyr, Arg, Glu, Asp, Ala, Ile, Leu, Pro or Val
<220> FEATURE:
<221> NAME/KEY: MOD_RES
<222> LOCATION: (64)..(64)
<223> OTHER INFORMATION: Phe, Asn, Cys, Gln, Gly, His, Met, Ser, Thr,
      Trp, Tyr, Asp, Glu, Ala, Ile, Leu, Pro or Val
<220> FEATURE:
<221> NAME/KEY: MOD_RES
```

```
<222> LOCATION: (65)..(65)
<223> OTHER INFORMATION: Lys, Asn, Cys, Gln, Gly, His, Met, Phe, Ser,
      Thr, Trp, Tyr, Arg, Asp, Glu, Ala, Ile, Leu, Pro or Val
<220> FEATURE:
<221> NAME/KEY: MOD_RES
<222> LOCATION: (66)..(66)
<223> OTHER INFORMATION: Ser, Asp or Glu
<220> FEATURE:
<221> NAME/KEY: MOD_RES
<222> LOCATION: (99)..(99)
<223> OTHER INFORMATION: Ser, Asp, Glu or Ala
<220> FEATURE:
<221> NAME/KEY: MOD_RES
<222> LOCATION: (100)..(100)
<223> OTHER INFORMATION: Asp or Glu
<220> FEATURE:
<221> NAME/KEY: MOD_RES
<222> LOCATION: (101)..(101)
<223> OTHER INFORMATION: Gly, Phe or Leu
<220> FEATURE:
<221> NAME/KEY: MOD_RES
<222> LOCATION: (102)..(102)
<223> OTHER INFORMATION: Arg, Asn, Cys, Gln, Gly, His, Met, Phe, Ser,
      Thr, Trp, Tyr or Lys
<220> FEATURE:
<221> NAME/KEY: MOD_RES
<222> LOCATION: (103)..(103)
<223> OTHER INFORMATION: Asn, Cys, Gln, Gly, His, Met, Phe, Ser, Thr,
      Trp, Tyr, Asp, Glu, Ala, Ile, Lys, Arg or Val
<220> FEATURE:
<221> NAME/KEY: MOD_RES
<222> LOCATION: (104)..(104)
<223> OTHER INFORMATION: Asp or Glu
<220> FEATURE:
<221> NAME/KEY: MOD_RES
<222> LOCATION: (105)..(105)
<223> OTHER INFORMATION: Met, Asp, Glu, Arg, His, Lys, Asn, Cys, Gln,
      Gly, Phe, Ser, Thr, Trp or Tyr
<220> FEATURE:
<221> NAME/KEY: MOD_RES
<222> LOCATION: (106)..(106)
<223> OTHER INFORMATION: Asp or Glu
<220> FEATURE:
<221> NAME/KEY: MOD_RES
<222> LOCATION: (107)..(107)
<223> OTHER INFORMATION: Ser, Asn, Cys, Gln, Gly, His, Met, Phe, Thr,
      Trp, Tyr, Asp, Glu, Ala, Ile, Leu, Pro or Val

<400> SEQUENCE: 33

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Xaa Phe Xaa Xaa Xaa
            20                  25                  30

Xaa Met Xaa Trp Val Lys Gln Ala Pro Gly Gln Gly Leu Glu Trp Ile
        35                  40                  45

Gly Xaa Ile Xaa Xaa Xaa Xaa Gly Xaa Xaa Xaa Xaa Xaa Xaa Xaa Xaa
    50                  55                  60

Xaa Xaa Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Xaa Xaa Xaa Xaa Xaa Xaa Xaa Xaa Trp Gly Gln Gly Thr
            100                 105                 110

Leu Val Thr Val Ser Ser
        115

<210> SEQ ID NO 34
<211> LENGTH: 118
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Ile, His, Asn, Gln, Ser, Thr or Glu
<220> FEATURE:
<221> NAME/KEY: MOD_RES
<222> LOCATION: (30)..(30)
<223> OTHER INFORMATION: Thr, His, Asn, Gln, Ser, Tyr or Arg
<220> FEATURE:
<221> NAME/KEY: MOD_RES
<222> LOCATION: (31)..(31)
<223> OTHER INFORMATION: Ser, Gln or Trp
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (33)..(33)
<223> OTHER INFORMATION: Tyr, Ala, Pro, Ser, Thr, Val or Trp
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (50)..(50)
<223> OTHER INFORMATION: Any amino acid
<220> FEATURE:
<221> NAME/KEY: MOD_RES
<222> LOCATION: (52)..(52)
<223> OTHER INFORMATION: Asn, Ala, Phe, His, Leu, Met, Ser, Thr, Val or
      Trp
<220> FEATURE:
<221> NAME/KEY: MOD_RES
<222> LOCATION: (53)..(53)
<223> OTHER INFORMATION: Any amino acid
<220> FEATURE:
<221> NAME/KEY: MOD_RES
<222> LOCATION: (54)..(54)
<223> OTHER INFORMATION: Ser, Glu, His, Lys, Asn, Gln, Arg, Thr, Trp,
      Tyr or Phe
<220> FEATURE:
<221> NAME/KEY: MOD_RES
<222> LOCATION: (55)..(55)
<223> OTHER INFORMATION: Asn, Glu, Lys, Gln, Ser, Thr, Met or Val
<220> FEATURE:
<221> NAME/KEY: MOD_RES
<222> LOCATION: (57)..(57)
<223> OTHER INFORMATION: Asp, Phe or Leu
<220> FEATURE:
<221> NAME/KEY: MOD_RES
<222> LOCATION: (58)..(58)
<223> OTHER INFORMATION: Any amino acid
<220> FEATURE:
<221> NAME/KEY: MOD_RES
<222> LOCATION: (59)..(59)
<223> OTHER INFORMATION: Asn, Ala, Phe, Leu, Met, Pro, Val, Trp, Asp or
      Tyr
<220> FEATURE:
<221> NAME/KEY: MOD_RES
<222> LOCATION: (60)..(66)
<223> OTHER INFORMATION: Any amino acid
<220> FEATURE:
<221> NAME/KEY: MOD_RES
<222> LOCATION: (99)..(99)
<223> OTHER INFORMATION: Ser or Ala
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (101)..(101)
<223> OTHER INFORMATION: Gly, Phe or Leu
<220> FEATURE:
```

```
<221> NAME/KEY: MOD_RES
<222> LOCATION: (102)..(102)
<223> OTHER INFORMATION: Any amino acid
<220> FEATURE:
<221> NAME/KEY: MOD_RES
<222> LOCATION: (103)..(103)
<223> OTHER INFORMATION: Asn, Ala, Asp, Glu, Phe, His, Ile, Lys, Met,
      Arg, Ser, Thr, Val or Tyr
<220> FEATURE:
<221> NAME/KEY: MOD_RES
<222> LOCATION: (104)..(107)
<223> OTHER INFORMATION: Any amino acid

<400> SEQUENCE: 34

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Xaa Phe Xaa Xaa Xaa
            20                  25                  30

Xaa Met Xaa Trp Val Lys Gln Ala Pro Gly Gln Gly Leu Glu Trp Ile
        35                  40                  45

Gly Xaa Ile Xaa Xaa Xaa Xaa Gly Xaa Xaa Xaa Xaa Xaa Xaa Xaa Xaa
    50                  55                  60

Xaa Xaa Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Xaa Xaa Xaa Xaa Xaa Xaa Xaa Xaa Trp Gly Gln Gly Thr
            100                 105                 110

Leu Val Thr Val Ser Ser
        115

<210> SEQ ID NO 35
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Ser, Ala, Ile, Leu, Met, Phe, Pro, Val, Trp,
      Asn, Cys, Gln, Gly, Ser, Thr or Tyr
<220> FEATURE:
<221> NAME/KEY: MOD_RES
<222> LOCATION: (54)..(54)
<223> OTHER INFORMATION: Ser, Ala, Ile, Leu, Met, Phe, Pro, Val, Trp,
      Asn, Cys, Gln, Gly, Ser, Thr or Tyr
<220> FEATURE:
<221> NAME/KEY: MOD_RES
<222> LOCATION: (57)..(57)
<223> OTHER INFORMATION: Asp, Ala, Ile, Leu, Met, Phe, Pro, Val or Trp
<220> FEATURE:
<221> NAME/KEY: MOD_RES
<222> LOCATION: (101)..(101)
<223> OTHER INFORMATION: Gly, Ala, Ile, Leu, Met, Phe, Pro, Val or Trp
<220> FEATURE:
<221> NAME/KEY: MOD_RES
<222> LOCATION: (103)..(103)
<223> OTHER INFORMATION: Asn, Cys, Gln, Gly, Ser, Thr or Tyr

<400> SEQUENCE: 35

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Xaa Tyr
            20                  25                  30

Tyr Met Tyr Trp Val Lys Gln Ala Pro Gly Gln Gly Leu Glu Trp Ile
```

```
                35                  40                  45
Gly Glu Ile Asn Pro Xaa Asn Gly Xaa Thr Asn Phe Asn Glu Lys Phe
            50                  55                  60

Lys Ser Lys Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Thr Arg Ser Asp Xaa Arg Xaa Asp Met Asp Ser Trp Gly Gln Gly Thr
            100                 105                 110

Leu Val Thr Val Ser Ser
        115

<210> SEQ ID NO 36
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Ser, Trp or Gln
<220> FEATURE:
<221> NAME/KEY: MOD_RES
<222> LOCATION: (54)..(54)
<223> OTHER INFORMATION: Ser, Phe or Gln
<220> FEATURE:
<221> NAME/KEY: MOD_RES
<222> LOCATION: (57)..(57)
<223> OTHER INFORMATION: Asp, Leu or Phe
<220> FEATURE:
<221> NAME/KEY: MOD_RES
<222> LOCATION: (101)..(101)
<223> OTHER INFORMATION: Gly, Leu or Phe
<220> FEATURE:
<221> NAME/KEY: MOD_RES
<222> LOCATION: (103)..(103)
<223> OTHER INFORMATION: Asn or Tyr

<400> SEQUENCE: 36

Gln Val Gln Leu Val Gln Ser Gly Ala Glu Val Val Lys Pro Gly Ala
 1               5                  10                  15

Ser Val Lys Leu Ser Cys Lys Ala Ser Gly Tyr Ile Phe Thr Xaa Tyr
            20                  25                  30

Tyr Met Tyr Trp Val Lys Gln Ala Pro Gly Gln Gly Leu Glu Trp Ile
        35                  40                  45

Gly Glu Ile Asn Pro Xaa Asn Gly Xaa Thr Asn Phe Asn Glu Lys Phe
            50                  55                  60

Lys Ser Lys Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Thr Arg Ser Asp Xaa Arg Xaa Asp Met Asp Ser Trp Gly Gln Gly Thr
            100                 105                 110

Leu Val Thr Val Ser Ser
        115

<210> SEQ ID NO 37
<211> LENGTH: 118
<212> TYPE: PRT
<213> ORGANISM: Artificial Sequence
<220> FEATURE:
<223> OTHER INFORMATION: Description of Artificial Sequence: Synthetic
```

-continued

```
              polypeptide
<220> FEATURE:
<221> NAME/KEY: MOD_RES
<222> LOCATION: (30)..(32)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (50)..(50)
<223> OTHER INFORMATION: Any amino acid
<220> FEATURE:
<221> NAME/KEY: MOD_RES
<222> LOCATION: (52)..(53)
<223> OTHER INFORMATION: Any amino acid
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (57)..(58)
<223> OTHER INFORMATION: Any amino acid
<220> FEATURE:
<221> NAME/KEY: MOD_RES
<222> LOCATION: (59)..(59)
<223> OTHER INFORMATION: Asp or Leu
<220> FEATURE:
<221> NAME/KEY: MOD_RES
<222> LOCATION: (60)..(66)
<223> OTHER INFORMATION: Any amino acid
<220> FEATURE:
<221> NAME/KEY: MOD_RES
<222> LOCATION: (99)..(107)
<223> OTHER INFORMATION: Any amino acid

<400> SEQUENCE: 37

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Glu Phe Xaa Xaa Xaa
                20                  25                  30

Phe Met Xaa Trp Val Lys Gln Ala Pro Gly Gln Gly Leu Glu Trp Ile
            35                  40                  45

Gly Xaa Ile Xaa Xaa Thr Xaa Gly Xaa Xaa Xaa Xaa Xaa Xaa Xaa Xaa
    50                  55                  60

Xaa Xaa Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Xaa Xaa Xaa Xaa Xaa Xaa Xaa Xaa Trp Gly Gln Gly Thr
            100                 105                 110

Leu Val Thr Val Ser Ser
        115

<210> SEQ ID NO 38
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (30)..(30)
```

```
<223> OTHER INFORMATION: His or Arg
<220> FEATURE:
<221> NAME/KEY: MOD_RES
<222> LOCATION: (31)..(31)
<223> OTHER INFORMATION: Gln or Trp
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (33)..(33)
<223> OTHER INFORMATION: Trp, Val or Pro
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (50)..(50)
<223> OTHER INFORMATION: Any amino acid
<220> FEATURE:
<221> NAME/KEY: MOD_RES
<222> LOCATION: (52)..(52)
<223> OTHER INFORMATION: Met or Trp
<220> FEATURE:
<221> NAME/KEY: MOD_RES
<222> LOCATION: (53)..(53)
<223> OTHER INFORMATION: Any amino acid
<220> FEATURE:
<221> NAME/KEY: MOD_RES
<222> LOCATION: (54)..(54)
<223> OTHER INFORMATION: Asn, Phe or Gln
<220> FEATURE:
<221> NAME/KEY: MOD_RES
<222> LOCATION: (55)..(55)
<223> OTHER INFORMATION: Met, Lys or Val
<220> FEATURE:
<221> NAME/KEY: MOD_RES
<222> LOCATION: (57)..(57)
<223> OTHER INFORMATION: Phe or Leu
<220> FEATURE:
<221> NAME/KEY: MOD_RES
<222> LOCATION: (58)..(58)
<223> OTHER INFORMATION: Any amino acid
<220> FEATURE:
<221> NAME/KEY: MOD_RES
<222> LOCATION: (59)..(59)
<223> OTHER INFORMATION: Phe or Tyr
<220> FEATURE:
<221> NAME/KEY: MOD_RES
<222> LOCATION: (60)..(66)
<223> OTHER INFORMATION: Any amino acid
<220> FEATURE:
<221> NAME/KEY: MOD_RES
<222> LOCATION: (99)..(100)
<223> OTHER INFORMATION: Any amino acid
<220> FEATURE:
<221> NAME/KEY: MOD_RES
<222> LOCATION: (101)..(101)
<223> OTHER INFORMATION: Phe or Leu
<220> FEATURE:
<221> NAME/KEY: MOD_RES
<222> LOCATION: (102)..(102)
<223> OTHER INFORMATION: Any amino acid
<220> FEATURE:
<221> NAME/KEY: MOD_RES
<222> LOCATION: (103)..(103)
<223> OTHER INFORMATION: His or Tyr
<220> FEATURE:
<221> NAME/KEY: MOD_RES
<222> LOCATION: (104)..(107)
<223> OTHER INFORMATION: Any amino acid

<400> SEQUENCE: 38

Gln Val Gln Leu Val Gln Ser Gly Ala Glu Val Val Lys Pro Gly Ala
1               5                   10                  15
```

Ser Val Lys Leu Ser Cys Lys Ala Ser Gly Tyr Xaa Phe Xaa Xaa Xaa
            20                  25                  30

Xaa Met Xaa Trp Val Lys Gln Ala Pro Gly Gln Gly Leu Glu Trp Ile
        35                  40                  45

Gly Xaa Ile Xaa Xaa Xaa Xaa Gly Xaa Xaa Xaa Xaa Xaa Xaa Xaa Xaa
    50                  55                  60

Xaa Xaa Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Xaa Xaa Xaa Xaa Xaa Xaa Xaa Xaa Trp Gly Gln Gly Thr
            100                 105                 110

Leu Val Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Trp Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Gln Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

```
Lys Ser Lys Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 41
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Gln Ser Gly Ala Glu Val Val Lys Pro Gly Ala
 1               5                  10                  15

Ser Val Lys Leu Ser Cys Lys Ala Ser Gly Tyr Ile Phe Thr Ser Tyr
             20                  25                  30

Tyr Met Tyr Trp Val Lys Gln Ala Pro Gly Gln Gly Leu Glu Trp Ile
         35                  40                  45

Gly Glu Ile Asn Pro Phe Asn Gly Asp Thr Asn Phe Asn Glu Lys Phe
 50                  55                  60

Lys Ser Lys Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 42
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Val Gln Ser Gly Ala Glu Val Val Lys Pro Gly Ala
 1               5                  10                  15

Ser Val Lys Leu Ser Cys Lys Ala Ser Gly Tyr Ile Phe Thr Ser Tyr
             20                  25                  30

Tyr Met Tyr Trp Val Lys Gln Ala Pro Gly Gln Gly Leu Glu Trp Ile
         35                  40                  45

Gly Glu Ile Asn Pro Gln Asn Gly Asp Thr Asn Phe Asn Glu Lys Phe
 50                  55                  60

Lys Ser Lys Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Ser Asp Gly Arg Asn Asp Met Asp Ser Trp Gly Gln Gly Thr
            100                 105                 110
```

Leu Val Thr Val Ser Ser
        115

<210> SEQ ID NO 43
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Phe Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 44
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Leu Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 45
<211> LENGTH: 118
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 45

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Phe Arg Asn Asp Met Asp Ser Trp Gly Gln Gly Thr
            100                 105                 110

Leu Val Thr Val Ser Ser
        115

<210> SEQ ID NO 46
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Leu Arg Asn Asp Met Asp Ser Trp Gly Gln Gly Thr
            100                 105                 110

Leu Val Thr Val Ser Ser
        115

<210> SEQ ID NO 47
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr

-continued

```
                20                  25                  30

Tyr Met Tyr Trp Val Lys Gln Ala Pro Gly Gln Gly Leu Glu Trp Ile
            35                  40                  45

Gly Glu Ile Asn Pro Ser Asn Gly Asp Thr Asn Phe Asn Glu Lys Phe
        50                  55                  60

Lys Ser Lys Ala Thr Leu Thr Val Asp Lys Ser Ala Ser Thr Ala Tyr
 65                 70                  75                  80

Met Glu Leu Ser Ser Leu Arg Ser Glu Asp Thr Ala Val Tyr Tyr Cys
                85                  90                  95

Thr Arg Ser Asp Gly Arg Tyr Asp Met Asp Ser Trp Gly Gln Gly Thr
            100                 105                 110

Leu Val Thr Val Ser Ser
        115

<210> SEQ ID NO 48
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Gln Leu Val Gln Ser Gly Ala Glu Val Val Lys Pro Gly Ala
 1               5                  10                  15

Ser Val Lys Leu Ser Cys Lys Ala Ser Gly Tyr Ile Phe His Ser Tyr
            20                  25                  30

Tyr Met Tyr Trp Val Lys Gln Ala Pro Gly Gln Gly Leu Glu Trp Ile
            35                  40                  45

Gly Glu Ile Asn Pro Ser Asn Gly Asp Thr Asn Phe Asn Glu Lys Phe
        50                  55                  60

Lys Ser Lys Ala Thr Leu Thr Val Asp Lys Ser Ala Ser Thr Ala Tyr
 65                 70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 49
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Gln Ser Gly Ala Glu Val Val Lys Pro Gly Ala
 1               5                  10                  15

Ser Val Lys Leu Ser Cys Lys Ala Ser Gly Tyr Ile Phe Thr Ser Tyr
            20                  25                  30

Trp Met Tyr Trp Val Lys Gln Ala Pro Gly Gln Gly Leu Glu Trp Ile
            35                  40                  45

Gly Glu Ile Asn Pro Ser Asn Gly Asp Thr Asn Phe Asn Glu Lys Phe
        50                  55                  60

Lys Ser Lys Ala Thr Leu Thr Val Asp Lys Ser Ala Ser Thr Ala Tyr
```

```
              65                  70                  75                  80
Met Glu Leu Ser Ser Leu Arg Ser Glu Asp Thr Ala Val Tyr Tyr Cys
                 85                  90                  95

Thr Arg Ser Asp Gly Arg Asn Asp Met Asp Ser Trp Gly Gln Gly Thr
                100                 105                 110

Leu Val Thr Val Ser Ser
        115

<210> SEQ ID NO 50
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
                20                  25                  30

Tyr Met Tyr Trp Val Lys Gln Ala Pro Gly Gln Gly Leu Glu Trp Ile
            35                  40                  45

Gly Glu Ile Asn Pro Asn Asn Gly Asp Thr Asn Phe Asn Glu Lys Phe
        50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                 85                  90                  95

Thr Arg Ser Asp Gly Arg Asn Asp Met Asp Ser Trp Gly Gln Gly Thr
                100                 105                 110

Leu Val Thr Val Ser Ser
        115

<210> SEQ ID NO 51
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
                20                  25                  30

Phe Met Tyr Trp Val Lys Gln Ala Pro Gly Gln Gly Leu Glu Trp Ile
            35                  40                  45

Gly Glu Ile Asn Pro Ser Asn Gly Asp Thr Asn Phe Asn Glu Lys Phe
        50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                 85                  90                  95

Thr Arg Ser Asp Gly Arg Asn Asp Met Asp Ser Trp Gly Gln Gly Thr
                100                 105                 110

Leu Val Thr Val Ser Ser
```

115

<210> SEQ ID NO 52
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asp Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 53
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Leu Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 54
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe His Ser Tyr
            20                  25                  30

Trp Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe His Ser Tyr
            20                  25                  30

Trp Met Tyr Trp Val Lys Gln Ala Pro Gly Gln Gly Leu Glu Trp Ile
        35                  40                  45

Gly Glu Ile Asn Pro Asn Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 56
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe His Ser Tyr
            20                  25                  30

```
Tyr Met Tyr Trp Val Lys Gln Ala Pro Gly Gln Gly Leu Glu Trp Ile
            35                  40                  45

Gly Glu Ile Asn Pro Asn Asn Gly Asp Thr Asn Phe Asn Glu Lys Phe
        50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
            115

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Trp Met Tyr Trp Val Lys Gln Ala Pro Gly Gln Gly Leu Glu Trp Ile
            35                  40                  45

Gly Glu Ile Asn Pro Asn Asn Gly Asp Thr Asn Phe Asn Glu Lys Phe
        50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
            115

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Gly Gly Ser Gly Gly Gly Gly Ser Gly Gly Gly Gly Ser Gly
1               5                   10                  15

Gly Gly Gly Ser
            20

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 59

His His His His His His
1               5
```

ANTI-CD154 ANTIBODIES

CROSS-REFERENCE TO RELATED APPLICATIONS

This application is a continuation application of U.S. application Ser. No. 11/572,647, issued as U.S. Pat. No. 8,647,625, which is a U.S. national phase application under 35 U.S.C. §371 of International Application Serial No. PCT/US2005/026320 filed Jul. 26, 2005, which claims priority to U.S. provisional application Ser. No. 60/591,337 filed Jul. 26, 2004, each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Sep. 10, 2013, is named B2047-7072US_S-L.txt and is 84,467 bytes in size.

FIELD OF THE INVENTION

The present invention is directed, in part, to anti-CD154 antibodies and fragments thereof that comprise at least one substituted amino acid in the variable region of either or both the light and heavy chain, and to compositions comprising such antibodies or fragments thereof, and to methods of using the antibodies or fragments thereof.

BACKGROUND OF THE INVENTION

The generation of humoral and cell-mediated immunity is orchestrated by the interaction of activated helper T cells with antigen-presenting cells ("APCs") and effector T cells. Activation of the helper T cells is not only dependent on the interaction of the antigen-specific T-cell receptor ("TCR") with its cognate peptide-MHC ligand, but also requires the coordinate binding and activation by a number of cell adhesion and costimulatory molecules (Salazar-Fontana et al., Curr. Opin. Hemat., 2001, 8, 5).

A critical costimulatory molecule is CD154 (also known as CD40 ligand, CD40L, gp39, T-BAM, T-Cell Activating Molecule, TRAP), a Type II transmembrane protein that is expressed in an activation-dependent, temporally-restricted, manner on the surface of CD4+ T cells. CD154 is also expressed, following activation, on a subset of CD8+ T cells, basophils, mast cells, eosinophils, natural killer cells, B cells, macrophages, dendritic cells and platelets. The CD154 counter-receptor, CD40, is a Type I membrane protein that is constitutively and widely expressed on the surface of many cell types, including APCs (Foy et al., Ann Rev. Immunol., 1996, 14, 591).

Signaling through CD40 by CD154 initiates a cascade of events that result in the activation of the CD40 receptor-bearing cells and optimal CD4+ T cell priming. More specifically, the cognate interaction between CD154 and CD40 promotes the differentiation of B cells into antibody secreting cells and memory B cells (Burkly, In Adv. Exp. Med. Bio., Vol. 489., D. M. Monroe, U. Hedner, M. R. Hoffman, C. Negrier, G. F. Savidge, and G. C. I. White, eds. Kluwer Academic/Plenum Publishers, 2001, p. 135). Additionally, the CD154-CD40 interaction promotes cell-mediated immunity through the activation of macrophages and dendritic cells and the generation of natural killer cells and cytotoxic T lymphocytes (Burkly, supra).

The CD40-CD154 interaction has been shown to be important in several experimentally induced autoimmune diseases, such as collagen-induced arthritis, experimental allergic encephalomyelitis ("EAE"), oophoritis, colitis, drug-induced lupus nephritis. Specifically, it has been shown that disease induction in all of these models can be blocked with CD154 antagonists at the time of antigen administration (Burkly, supra).

The blockade of disease using anti-CD154 antagonists has also been seen in animal models of spontaneous autoimmune disease, including insulin-dependent diabetes and lupus nephritis, as well as in graft-vs-host disease, transplant, pulmonary fibrosis, and atherosclerosis disease models (Burkly, supra).

Although glycosylated anti-CD154 antibodies have proven useful for the prevention and treatment of several immune response-related diseases, in some subjects, therapies using them are sometimes complicated by thromboembolitic activity. Although the mechanism of this side effect is unknown, it could involve the colligation by the anti-CD154 antibody, or aggregates thereof, of FcgRIIa and CD154 on platelets, leading to inappropriate platelet activation. Binding to other Fcγ receptors and complement could also potentiate this effect. Thus, forms of anti-CD154 antibodies that do not bind to effector receptors may be safer and/or more effective for therapeutic use.

The mechanism by which anti-CD154 antibodies inhibit immune function may be more complex than simple binding to CD154 to block interactions with CD40 and, in fact, may include contributions by effector pathways. For example, antibody-antigen binding may induce deletion of activated T cells through Fc domain binding to Fcγ receptors or complement components. Alternatively, binding of the antibody to CD154 may be enhanced by the formation of a cell surface scaffold of the antibody on Fcγ receptor-bearing cells. In addition, access of the antibody to its site of action may be promoted by Fcγ receptor binding interactions.

The pivotal role of CD154 in regulating the function of both the humoral and cell-mediated immune response has provoked great interest in the use of inhibitors of this pathway for therapeutic immunomodulation (U.S. Pat. No. 5,474,771). As such, anti-CD154 antibodies have been shown to be beneficial in a wide variety of models of immune response to other therapeutic proteins or gene therapy, allergens, autoimmunity and transplantation (U.S. Pat. No. 5,474,771; Burkly, supra).

Accordingly, there remains a need for antibodies that do not provoke a strong immune response but yet bind strongly to their antigens and methods for identifying such antibodies, in particular, improved CD154 antibodies.

SUMMARY OF THE INVENTION

The present invention provides peptides comprising an amino acid sequence at least 80% identical to SEQ ID NO:3, or a fragment thereof, wherein the amino acid at each of positions 24, 26, 27, 28, 30, 31, 32, 33, 34, 35, 36, 38, 54, 57, 58, 59, 60, 93, 95, 96, 97, 98, 100, and 101, independently, is any naturally occurring amino acid or any non-naturally occurring amino acid, wherein the peptide does not consist of SEQ ID NO:1, and wherein the fragment comprises at least one of positions 24, 26, 27, 28, 30, 31, 32, 33, 34, 35, 36, 38, 54, 57, 58, 59, 60, 93, 95, 96, 97, 98, 100, and 101, and when complexed with the wild type 5c8 heavy chain, the peptide or fragment thereof can bind to CD154.

In some embodiments, the amino acid at position 24 is selected from the group consisting of Arg, Asn, Cys, Gln, Gly, His, Met, Phe, Ser, Thr, Trp, Tyr, Ala, Ile, Leu, Pro, Val, Asp, Glu, and Lys; the amino acid at position 26 is selected from the group consisting of Ser, Asn, Cys, Gln, Gly, His, Met, Phe, Thr, Trp, Tyr, Ala, Ile, Leu, Pro, Val, Asp, and Glu; the amino acid at position 27 is selected from the group consisting of Gln, Asn, Cys, Gly, His, Met, Phe, Ser, Thr, Trp, Tyr, Asp, Glu, Arg, and Lys; the amino acid at position 28 is selected from the group consisting of Arg, Asn, Cys, Gln, Gly, His, Met, Phe, Ser, Thr, Trp, Tyr, Asp, Glu, Ala, Ile, Leu, Pro, and Val; the amino acid at position 30 is selected from the group consisting of Ser, Asn, Cys, Gln, Gly, His, Met, Phe, Thr, Trp, Tyr, Asp, Glu, Arg, and Lys; the amino acid at position 31 is selected from the group consisting of Ser, Asn, Cys, Gln, Gly, His, Met, Phe, Thr, Trp, Tyr, Ala, Ile, Leu, Pro, Val, Arg, and Lys; the amino acid at position 32 is selected from the group consisting of Ser, Asn, Cys, Gln, Gly, His, Met, Phe, Thr, Trp, Tyr, Arg, Ala, Ile, Leu, and Lys; the amino acid at position 33 is selected from the group consisting of Thr, Asn, Cys, Gln, Gly, His, Met, Phe, Ser, Trp, Tyr, Asp, Glu, Arg, Ala, Val, and Lys; the amino acid at position 34 is selected from the group consisting of Tyr, Asn, Cys, Gln, Gly, His, Met, Phe, Ser, Thr, Trp Ala, Ile, Leu, Pro, Val, Asp, Glu, Arg, and Lys; the amino acid at position 35 is selected from the group consisting of Ser, Asn, Cys, Gln, Gly, His, Met, Phe, Thr, Trp, and Tyr; the amino acid at position 36 is selected from the group consisting of Tyr, Asn, Cys, Gln, Gly, His, Met, Phe, Ser, Thr, Trp Asp, Ala, Leu, and Glu; the amino acid at position 38 is selected from the group consisting of His, Asn, Cys, Gln, Gly, Met, Phe, Ser, Thr, Trp, Tyr, Ala, Ile, Leu, Pro, Val, Asp, Glu, Arg, and Lys; the amino acid at position 54 is selected from the group consisting of Tyr, Asn, Cys, Gln, Gly, His, Met, Phe, Ser, Thr, Trp Ala, Ile, Leu, Pro, Val, Asp, and Glu; the amino acid at position 57 is selected from the group consisting of Asn, Cys, Gln, Gly, His, Met, Phe, Ser, Thr, Trp, Tyr, Asp, and Glu; the amino acid at position 58 is selected from the group consisting of Leu, Asn, Cys, Gln, Gly, His, Met, Phe, Ser, Thr, Trp Asp, and Glu; the amino acid at position 59 is selected from the group consisting of Glu, Asn, Cys, Gln, Gly, His, Met, Phe, Ser, Thr, Trp, Tyr, and Asp; the amino acid at position 60 is selected from the group consisting of Ser, Asp, and Glu; the amino acid at position 93 is selected from the group consisting of Gln, Asn, Cys, Gly, His, Met, Phe, Ser, Thr, Trp, Tyr, Ala, Ile, Leu, Pro, Val, Asp, Glu, Arg, and Lys; the amino acid at position 95 is selected from the group consisting of Ser, Asn, Cys, Gln, Gly, His, Met, Phe, Thr, Trp, Tyr, Asp, and Glu; the amino acid at position 96 is selected from the group consisting of Trp, Asn, Cys, Gln, Gly, His, Met, Phe, Ser, Thr, Tyr, Asp, Glu, Arg, and Lys; the amino acid at position 97 is selected from the group consisting of Glu and Asp; the amino acid at position 98 is selected from the group consisting of Ile, Asn, Cys, Gln, Gly, His, Met, Phe, Ser, Thr, Trp, Tyr, Asp, Ala, Leu, Pro, Val, and Glu; the amino acid at position 100 is selected from the group consisting of Pro, Asn, Cys, Gln, Gly, His, Met, Phe, Ser, Thr, Trp, Tyr, Asp, and Glu; and the amino acid at position 101 is selected from the group consisting of Thr, Asn, Cys, Gln, Gly, His, Met, Phe, Ser, Trp, Tyr, Ala, Ile, Leu, Pro, Val, Asp, and Glu.

In some embodiments, the amino acid at position 26 is selected from the group consisting of Ser and Asp; the amino acid at position 27 is selected from the group consisting of Gln and Glu; the amino acid at position 28 is selected from the group consisting of Arg and Glu; the amino acid at position 31 is selected from the group consisting of Ser, Ala, His, Asn, Thr, Val, and Trp; the amino acid at position 32 is selected from the group consisting of Ser, Ala, Phe, Ile, Leu, Met, and Trp; the amino acid at position 33 is selected from the group consisting of Thr, Ala, Phe, Met, Val, Trp, Asp, Arg, Tyr, and Gln; the amino acid at position 34 is selected from the group consisting of Tyr, Ala, Asp, Glu, Phe, Ile, Lys, Leu, Met, Arg, Val, and Trp; the amino acid at position 36 is selected from the group consisting of Tyr, Ala, Phe, Leu, and Trp; the amino acid at position 54 is selected from the group consisting of Tyr and Glu; the amino acid at position 96 is selected from the group consisting of Trp, Asp, Glu, His, Arg, Ser, and Thr; and the amino acid at position 98 is selected from the group consisting of Ile, Ala, Phe, His, Leu, Met, Asn, Pro, Gln, Ser, Thr, Val, Trp, and Tyr.

In some embodiments, the amino acid at position 26 is selected from the group consisting of Ser, Asp and Glu; the amino acid at position 27 is selected from the group consisting of Gln, Asp, and Glu; the amino acid at position 31 is selected from the group consisting of Ser, Asn, Cys, Gln, Gly, Thr, and Tyr; the amino acid at position 32 is selected from the group consisting of Ser, Ala, Ile, Leu, Met, Phe, Pro, Val, and Trp; the amino acid at position 33 is selected from the group consisting of Thr, Asn, Cys, Gln, Gly, Ser, and Tyr; the amino acid at position 98 is selected from the group consisting of Ile, Asn, Cys, Gln, Gly, Ser, Thr, and Tyr; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the amino acid at position is 26 Asp; the amino acid at position 27 is Glu; the amino acid at position 28 is Glu; the amino acid at position 31 is Val; the amino acid at position 33 is selected from the group consisting of Asp and Arg; and the amino acid at position 54 is Glu.

In some embodiments, the amino acid at position 31 is selected from the group consisting of His and Asn; the amino acid at position 32 is selected from the group consisting of Trp and Phe; the amino acid at position 33 is selected from the group consisting of Trp, Tyr, and Gln; the amino acid at position 36 is selected from the group consisting of Leu and Trp; the amino acid at position 96 is His; and the amino acid at position 98 is selected from the group consisting of Phe and Gln.

In some embodiments, the amino acid at position 26 is selected from the group consisting of Ser and Asp; the amino acid at position 27 is selected from the group consisting of Gln and Glu; the amino acid at position 31 is selected from the group consisting of Ser and Asn; the amino acid at position 32 is selected from the group consisting of Ser and Phe; the amino acid at position 33 is selected from the group consisting of Thr, Gln, and Tyr; the amino acid at position 98 is selected from the group consisting of Ile and Gln; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26 is Asp; the amino acid at position 27 is Gln; the amino acid at position 31 and position 32 is Ser; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26, position 31, and position 32 is Ser; the amino acid at position 27 is Glu; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26 and position 32 is Ser; the amino acid at position 27 is Gln; the amino acid at position 31 is Asn; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26 and position 31 is Ser; the amino acid at position 27 is Gln; the amino acid at position 32 is Phe; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26, position 31, and position 32 is Ser; the amino acid at position 27 and position 33 is Gln; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26, position 31, and position 32 is Ser; the amino acid at position 27 is Gln; the amino acid at position 33 is Tyr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26, position 31, and position 32 is Ser; the amino acid at position 27 and position 98 is Gln; the amino acid at position 33 is Thr; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26 is Asp; the amino acid at position 27 is Glu; the amino acid at position 31 and position 32 is Ser; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26 is Asp; the amino acid at position 27 is Glu; the amino acid at position 31 is Asn; the amino acid at position 32 is Ser; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26 is Asp; the amino acid at position 27 is Glu; the amino acid at position 31 is Ser; the amino acid at position 32 is Phe; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26 is Asp; the amino acid at position 27 is Glu; the amino acid at position 31 and position 32 is Ser; the amino acid at position 33 is Gln; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26 is Asp; the amino acid at position 27 is Glu; the amino acid at position 31 and position 32 is Ser; the amino acid at position 33 is Tyr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26 is Asp; the amino acid at position 27 is Glu; the amino acid at position 31 and position 32 is Ser; the amino acid at position 33 is Thr; the amino acid at position 98 is Gln; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 27 and position 93 is Gln; the amino acid at position 26, position 31, position 32, position 30, position 35, position 60, and position 95 is Ser; the amino acid at position 33 and position 101 is Thr; the amino acid at position 98 is Ile; the amino acid at position 24 and position 28 is Arg; the amino acid at position 34 and position 54 is Tyr; the amino acid at position 38 is His; the amino acid at position 57 is Asn; the amino acid at position 58 is Leu; the amino acid at position 59 and position 97 is Glu; the amino acid at position 96 and position 36 is Trp; and the amino acid at position 100 is Pro.

In some embodiments, the peptide comprises SEQ ID NO:3 wherein the amino acid at position 27 and position 93 is Gln; the amino acid at position 26, position 31, position 32, position 30, position 35, position 60, and position 95 is Ser; the amino acid at position 101 is Thr; the amino acid at position 98 is Ile; the amino acid at position 24 and position 28 is Arg; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 96 and position 33 is Trp; and the amino acid at position 100 is Pro.

In some embodiments, the peptide comprises SEQ ID NO:3 wherein the amino acid at position 27 and position 93 is Gln; the amino acid at position 26, position 32, position 30, position 35, position 60, and position 95 is Ser; the amino acid at position 33 and position 101 is Thr; the amino acid at position 98 is Ile; the amino acid at position 24 and position 28 is Arg; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 96 is Trp; the amino acid at position 31 is Val; and the amino acid at position 100 is Pro.

In some embodiments, the peptide comprises SEQ ID NO:3 wherein the amino acid at position 27 and position 93 is Gln; the amino acid at position 26, position 31, position 32, position 30, position 35, position 60, and position 95 is Ser; the amino acid at position 101 is Thr; the amino acid at position 98 is Ile; the amino acid at position 24 and position 28 is Arg; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 96 is Trp; the amino acid at position 33 is Asp; and the amino acid at position 100 is Pro.

In some embodiments, the peptide comprises SEQ ID NO:3 wherein the amino acid at position 27 and position 93 is Gln; the amino acid at position 26, position 31, position 32, position 30, position 35, position 60, and position 95 is Ser; the amino acid at position 33 and position 101 is Thr; the amino acid at position 98 is Ile; the amino acid at position 24 and position 28 is Arg; the amino acid at position 34 and position 36 is Tyr; the amino acid at position 38 is His; the amino acid at position 57 is Asn; the amino acid at position 58 is Leu; the amino acid at position 54, position 59 and position 97 is Glu; the amino acid at position 96 is Trp; and the amino acid at position 100 is Pro.

In some embodiments, the peptide comprises SEQ ID NO:3 wherein the amino acid at position 27 and position 93 is Gln; the amino acid at position 26, position 31, position 32, position 30, position 35, position 60, and position 95 is Ser; the amino acid at position 33 and position 101 is Thr; the amino acid at position 98 is Ile; the amino acid at position 24 and position 28 is Arg; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 96 is Trp; and the amino acid at position 100 is Pro.

In some embodiments, the peptide comprises SEQ ID NO:3 wherein the amino acid at position 26 is Asp; the amino acid at position 27 is Glu; the amino acid at position 31 and position 32 is Ser; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 33 and position 96 is Trp; the amino acid at position 100 is Pro; and the amino acid at position 101 is Thr.

The present invention also provides peptides that comprise an amino acid sequence at least 80% identical to SEQ ID NO:6, or a fragment thereof, wherein the amino acid at each of positions 28, 30, 31, 32, 33, 35, 50, 52, 53, 54, 55, 57, 58, 59, 60, 61, 62, 63, 64, 65, 66, 99, 100, 101, 102, 103, 104, 105, 106, and 107, independently, is any naturally occurring amino acid or any non-naturally occurring amino acid, wherein the peptide does not consist of SEQ ID NO:4, and wherein the fragment comprises at least one of positions 28, 30, 31, 32, 33, 35, 50, 52, 53, 54, 55, 57, 58, 59, 60, 61, 62, 63, 64, 65, 66, 99, 100, 101, 102, 103, 104, 105, 106, and 107, and when complexed with the wild type 5c8 light chain, the peptide or fragment thereof can bind to CD154.

In some embodiments, the amino acid at position 28 is selected from the group consisting of Ile, Asp, Glu, Arg, Lys, Asn, Cys, Gln, Gly, His, Met, Phe, Ser, Thr, Trp and Trp; the amino acid at position 30 is selected from the group consisting of Thr, Asp, Glu, Arg, Lys, Asn, Cys, Gln, Gly, His, Met, Phe, Ser, Trp, Tyr, Ala, Ile, Leu, Pro, and Val; the amino acid at position 31 is selected from the group consisting of Ser, Arg, His, Lys, Gln, and Trp; the amino acid at position 32 is selected from the group consisting of Tyr, Asp, Glu, Arg, Lys, Asn, Cys, Gln, Gly, His, Met, Phe, Ser, Trp, Ala, Ile, Leu, Pro, and Val; the amino acid at position 33 is selected from the group consisting of Tyr, Asp, Glu, Asn, Cys, Gln, Gly, His, Met, Phe, Ser, Thr, Trp Ala, Ile, Leu, Pro, and Val; the amino acid at position 35 is selected from the group consisting of Tyr, Asn, Cys, Gln, Gly, His, Met, Phe, Ser, Thr, Trp Asp, and Glu; the amino acid at position 50 is selected from the group consisting of Glu and Asp; the amino acid at position 52 is selected from the group consisting of Asn, Cys, Gln, Gly, His, Met, Phe, Ser, Thr, Trp, Tyr, Arg, Ala, Leu, Val, and Lys; the amino acid at position 53 is selected from the group consisting of Pro, Asn, Cys, Gln, Gly, His, Met, Phe, Ser, Thr, Trp, Tyr, Asp, and Glu; the amino acid at position 54 is selected from the group consisting of Ser, Asn, Cys, Gln, Gly, His, Met, Phe, Thr, Trp, Tyr, Arg, Lys, and Glu; the amino acid at position 55 is selected from the group consisting of Asn, Glu, Lys, Gln, Ser, Thr, Met, and Val; the amino acid at position 57 is selected from the group consisting of Asp, Glu, Phe, and Leu; the amino acid at position 58 is selected from the group consisting of Thr, Asn, Cys, Gln, Gly, His, Met, Phe, Ser, Trp, Tyr, Ala, Ile, Leu, Pro, and Val; the amino acid at position 59 is selected from the group consisting of Asn, Cys, Gln, Gly, His, Met, Phe, Ser, Thr, Trp, Tyr, Ala, Ile, Leu, Pro, Val, Asp, and Glu; the amino acid at position 60 is selected from the group consisting of Phe, Asp, Asn, Cys, Gln, Gly, His, Met, Ser, Thr, Trp, Tyr, Glu, Arg, Lys, Ala, Ile, Leu, Pro, and Val; the amino acid at position 61 is selected from the group consisting of Asn, Asp, and Glu; the amino acid at position 62 is selected from the group consisting of Glu and Asp; the amino acid at position 63 is selected from the group consisting of Lys, Asn, Cys, Gln, Gly, His, Met, Phe, Ser, Thr, Trp, Tyr, Arg, Glu, Asp, Ala, Ile, Leu, Pro, and Val; the amino acid at position 64 is selected from the group consisting of Phe, Asn, Cys, Gln, Gly, His, Met, Ser, Thr, Trp, Tyr, Asp, Glu, Ala, Ile, Leu, Pro, and Val; the amino acid at position 65 is selected from the group consisting of Lys, Asn, Cys, Gln, Gly, His, Met, Phe, Ser, Thr, Trp, Tyr, Arg, Asp, Glu, Ala, Ile, Leu, Pro, and Val; the amino acid at position 66 is selected from the group consisting of Ser, Asp, and Glu; the amino acid at position 99 is selected from the group consisting of Ser, Asp, Glu, and Ala; the amino acid at position 100 is selected from the group consisting of Asp and Glu; the amino acid at position 101 is selected from the group consisting of Gly, Phe, and Leu; the amino acid at position 102 is selected from the group consisting of Arg, Asn, Cys, Gln, Gly, His, Met, Phe, Ser, Thr, Trp, Tyr, and Lys; the amino acid at position 103 is selected from the group consisting of Asn, Cys, Gln, Gly, His, Met, Phe, Ser, Thr, Trp, Tyr, Asp, Glu, Ala, Ile, Lys, Arg, and Val; the amino acid at position 104 is selected from the group consisting of Asp and Glu; the amino acid at position 105 is selected from the group consisting of Met, Asp, Glu, Arg, His, Lys, Asn, Cys, Gln, Gly, Phe, Ser, Thr, Trp, and Tyr; the amino acid at position 106 is selected from the group consisting of Asp and Glu; and the amino acid at position 107 is selected from the group consisting of Ser, Asn, Cys, Gln, Gly, His, Met, Phe, Thr, Trp, Tyr, Asp, Glu, Ala, Ile, Leu, Pro, and Val.

In some embodiments, the amino acid at position 28 is selected from the group consisting of Ile, His, Asn, Gln, Ser, Thr, and Glu; the amino acid at position 30 is selected from the group consisting of Thr, His, Asn, Gln, Ser, Tyr, and Arg; the amino acid at position 31 is selected from the group consisting of Ser, Gln, and Trp; the amino acid at position 33 is selected from the group consisting of Tyr, Ala, Pro, Ser, Thr, Val, and Trp; the amino acid at position 52 is selected from the group consisting of Asn, Ala, Phe, His, Leu, Met, Ser, Thr, Val, and Trp; the amino acid at position 54 is selected from the group consisting of Ser, Glu, His, Lys, Asn, Gln, Arg, Thr, Trp, Tyr, and Phe; the amino acid at position 55 is selected from the group consisting of Asn, Glu, Lys, Gln, Ser, Thr, Met, and Val; the amino acid at position 57 is selected from the group consisting of Asp, Phe, and Leu; the amino acid at position 59 is selected from the group consisting of Asn, Ala, Phe, Leu, Met, Pro, Val, Trp, Asp, and Tyr; the amino acid at position 99 is selected from the group consisting of Ser and Ala; the amino acid at position 101 is selected from the group consisting of Gly, Phe, and Leu; and the amino acid at position 103 is selected from the group consisting of Asn, Ala, Asp, Glu, Phe, His, Ile, Lys, Met, Arg, Ser, Thr, Val, and Tyr.

In some embodiments, the amino acid at position 31 and position 54 is, independently, selected from the group consisting of Ser, Ala, Ile, Leu, Met, Phe, Pro, Val, Trp, Asn, Cys, Gln, Gly, Ser, Thr, and Tyr; the amino acid at position 57 is selected from the group consisting of Asp, Ala, Ile, Leu, Met, Phe, Pro, Val, and Trp; the amino acid at position 101 is selected from the group consisting of Gly, Ala, Ile, Leu, Met, Phe, Pro, Val, and Trp; the amino acid at position 103 is selected from the group consisting of Asn, Cys, Gln, Gly, Ser, Thr, and Tyr; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the amino acid at position 31 is selected from the group consisting of Ser, Trp, and Gln; the amino acid at position 54 is selected from the group consisting of Ser, Phe, and Gln; the amino acid at position 57 is selected from the group consisting of Asp, Leu, and Phe; the amino acid at position 101 is selected from the group consisting of Gly, Leu, and Phe; the amino acid at position 103 is selected from the group consisting of Asn and Tyr; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the amino acid at position 28 is Glu; the amino acid at position 33 is Phe; the amino acid at position 54 is Thr; and the amino acid at position 59 is selected from the group consisting of Asp and Leu.

In some embodiments, the amino acid at position 30 is selected from the group consisting of His and Arg; the amino acid at position 31 is selected from the group consisting of Gln and Trp; the amino acid at position 33 is selected from the group consisting of Trp, Val, and Pro; the amino acid at position 52 is selected from the group consisting of Met and Trp; the amino acid at position 54 is selected from the group consisting of Asn, Phe, and Gln; the amino acid at position 55 is selected from the group consisting of Met, Lys, and Val; the amino acid at position 57 is selected from the group consisting of Phe and Leu; the amino acid at position 59 is selected from the group consisting of Phe and Tyr; the amino acid at position 101 is selected from the group consisting of Phe and Leu; and the amino acid at position 103 is selected from the group consisting of His and Tyr.

In some embodiments, the peptide comprises SEQ ID NO:6 wherein the amino acid at position 31 is Trp; the amino acid at position 54 is Ser; the amino acid at position 57 is Asp; the amino acid at position 101 is Gly; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 is Gln; the amino acid at position 54 is Ser; the amino acid at position 57 is Asp; the amino acid at position 101 is Gly; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 is Ser; the amino acid at position 54 is Phe; the amino acid at position 57 is Asp; the amino acid at position 101 is Gly; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 is Ser; the amino acid at position 54 is Gln; the amino acid at position 57 is Asp; the amino acid at position 101 is Gly; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 and position 54 is Ser; the amino acid at position 57 is Phe; the amino acid at position 101 is Gly; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 and position 54 is Ser; the amino acid at position 57 is Leu; the amino acid at position 101 is Gly; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 and position 54 is Ser; the amino acid at position 57 is Asp; the amino acid at position 101 is Phe; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 and position 54 is Ser; the amino acid at position 57 is Asp; the amino acid at position 101 is Leu; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 and position 54 is Ser; the amino acid at position 57 is Asp; the amino acid at position 101 is Gly; the amino acid at position 103 is Tyr; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31, position 54, position 66, position 99, and position 107 is Ser; the amino acid at position 57, position 100, position 104, and position 106 is Asp; the amino acid at position 101 is Gly; the amino acid at position 103, position 52, position 55, position 59, and position 61 is Asn; the amino acid at position 28 is Ile; the amino acid at position 58 is Thr; the amino acid at position 32, position 33, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; the amino acid at position 30 is His; and the amino acid at position 105 is Met.

In some embodiments, the peptide comprises SEQ ID NO:6 wherein the amino acid at position 31, position 54, position 66, position 99, and position 107 is Ser; the amino acid at position 57, position 100, position 104, and position 106 is Asp; the amino acid at position 101 is Gly; the amino acid at position 103, position 52, position 55, position 59, and position 61 is Asn; the amino acid at position 28 is Ile; the amino acid at position 30 and position 58 is Thr; the amino acid at position 32, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; the amino acid at position 33 is Trp; and the amino acid at position 105 is Met.

In some embodiments, the peptide comprises SEQ ID NO:6 wherein the amino acid at position 31, position 66, position 99, and position 107 is Ser; the amino acid at position 57, position 100, position 104, and position 106 is Asp; the amino acid at position 101 is Gly; the amino acid at position 103, position 52, position 54, position 55, position 59, and position 61 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; and the amino acid at position 105 is Met.

In some embodiments, the peptide comprises SEQ ID NO:6 wherein the amino acid at position 31, position 54, position 66, position 99, and position 107 is Ser; the amino acid at position 57, position 100, position 104, and position 106 is Asp; the amino acid at position 101 is Gly; the amino acid at position 103, position 52, position 55, position 59, and position 61 is Asn; the amino acid at position 28 is Ile; the amino acid at position 30 and position 58 is Thr; the amino acid at position 32, and position 35 is Tyr; the amino acid at position 50 and position 62 is Glu; the amino acid at position 53 is Pro; the amino acid at position 33, position 60, and position 64 is Phe; the amino acid at position 63 and position 65 is Lys; the amino acid at position 102 is Arg; and the amino acid at position 105 is Met.

In some embodiments, the peptide comprises SEQ ID NO:6 wherein the amino acid at position 31, position 54, position 66, position 99, and position 107 is Ser; the amino acid at position 57, position 59, position 100, position 104, and position 106 is Asp; the amino acid at position 101 is Gly; the amino acid at position 103, position 52, position 55, and position 61 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; and the amino acid at position 105 is Met.

In some embodiments, the peptide comprises SEQ ID NO:6 wherein the amino acid at position 31, position 54, position 66, position 99, and position 107 is Ser; the amino acid at position 57, position 100, position 104, and position 106 is Asp; the amino acid at position 101 is Gly; the amino acid at position 103, position 52, position 55, and position 61 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; the amino acid at position 59 is Leu; and the amino acid at position 105 is Met.

The present invention also provides compositions comprising any of the peptide disclosed herein.

The present invention also provides nucleic acid molecules encoding any of the peptides disclosed herein.

The present invention also provides vectors comprising any of the nucleic acid molecules disclosed herein.

The present invention also provides compositions comprising any of the nucleic acid molecules or vectors disclosed herein.

The present invention also provides host cells comprising any of the nucleic acid molecules or vectors disclosed herein.

The present invention also provides antibodies, or fragments thereof, comprising any of the peptides disclosed herein, wherein the antibodies or fragments thereof can bind to human CD154.

In some embodiments, the antibody fragment is selected from the group consisting of a single chain antibody (scFv), a F(ab')$_2$ fragment, a Fab fragment, and an Fd fragment.

In some embodiments, the antibody, or fragment thereof, is labeled with a detectable marker, such as, a marker selected from the group consisting of radioactive isotope, enzyme, fluorochrome, colloidal gold, dye, and biotin.

In some embodiments, the antibody, or fragment thereof, is conjugated to a therapeutic agent, such as, one selected from the group consisting of a radioisotope, toxin, toxoid, and chemotherapeutic agent; or is conjugated to a bead.

In some embodiments, the antibody, or fragment thereof, comprises at least one high molecular-weight polymer, such as, one selected from the group consisting of polyethyleneimine and polylysine.

In some embodiments, the antibody, or fragment thereof, comprises at least one amino acid that is selected from the group consisting of PEGylated and glycosylated.

The present invention also provides compositions comprising any of the antibodies, or fragments thereof, disclosed herein.

The present invention also provides kits comprising any of the antibodies, or fragments thereof, disclosed herein.

The present invention also provides methods of treating or preventing a CD154-related human disease or disorder comprising administering to a human a therapeutically- or prophylactically-effective amount of an antibody, or fragment thereof, of any of claims 55 to 77, or a composition of claim 53, such that the CD154-related human disease or disorder is diminished or prevented.

In some embodiments, the human disease or disorder is inflammation, such as, one selected from the group consisting of inflammation associated with arthritis, contact dermatitis, hyper-IgE syndrome, inflammatory bowel disease, allergic asthma, and idiopathic inflammatory disease.

In some embodiments, the arthritis is selected from the group consisting of rheumatoid arthritis, non-rheumatoid inflammatory arthritis, arthritis associated with Lyme disease, and inflammatory osteoarthritis.

In some embodiments, the idiopathic inflammatory disease is selected from the group consisting of psoriasis and systemic lupus erythematosus.

In some embodiments, the disease or disorder is selected from the group consisting of Myasthenia gravis, Graves' disease, idiopathic thrombocytopenia purpura, hemolytic anemia, diabetes mellitus, Crohn's disease, multiple sclerosis, and drug-induced autoimmune diseases.

In some embodiments, the disorder is rejection by the subject of a transplanted organ, such as, one selected from the group consisting of a transplanted heart, kidney, liver, skin, pancreatic islet cells, and bone marrow.

In some embodiments, the disorder is selected from the group consisting of graft-vs-host disease, allergic responses, an autoimmune response, and fibrosis in a subject, such as, pulmonary fibrosis or fibrotic disease.

In some embodiments, the pulmonary fibrosis is selected from the group consisting of pulmonary fibrosis secondary to adult respiratory distress syndrome, drug-induced pulmonary fibrosis, idiopathic pulmonary fibrosis, and hypersensitivity pneumonitis; and wherein the fibrotic disease is selected from the group consisting of Hepatitis-C, Hepatitis-B, cirrhosis, cirrhosis of the liver secondary to a toxic insult, cirrhosis of the liver secondary to drugs, cirrhosis of the liver secondary to a viral infection, and cirrhosis of the liver secondary to an autoimmune disease.

In some embodiments, the autoimmune response is selected from the group consisting of one derived from Reiter' syndrome, spondyloarthritis, Lyme disease, HIV infection, syphilis, and tuberculosis.

In some embodiments, the disease or disorder is gastrointestinal disease, such as, one selected from the group consisting of esophageal dysmotility, inflammatory bowel disease, and scleroderma; or is a vascular disease, wherein the vascular disease is selected from the group consisting of atherosclerosis and reperfusion injury.

In some embodiments, the disease or disorder is a T cell tumor cancer, such as, one selected from the group consisting of a T cell leukemia and lymphoma.

The present invention also provides peptides, and fragments thereof, for use in treating a human disease or disorder associated with CD154 and in the manufacture of a medicament for the treatment of a human disease or disorder associated with CD154.

DESCRIPTION OF EMBODIMENTS

The present invention provides peptides, particularly light chain and heavy chain variable regions, and fragments thereof, and antibodies, and fragments thereof, comprising the same, wherein the peptides comprise at least one amino acid substitution compared to wild type 5c8 antibody.

The term "antibody", as used herein, includes monoclonal antibodies (including full length monoclonal antibodies), polyclonal antibodies, multispecific antibodies (for example, bispecific antibodies), chimeric antibodies, CDR-grafted antibodies, humanized antibodies, human antibodies, and the like, and fragments thereof.

The phrase "antibody fragment", or the like, as used herein, includes for example, an antibody light chain ($V_L$), an antibody heavy chain ($V_H$), a single chain antibody (scFv), a $F(ab')_2$ fragment, a Fab fragment, a Fab' fragment, an Fd fragment, an Fv fragment, and a single domain antibody fragment (DAb).

The term "CDR", as used herein, includes the complementarity determining regions as described by, for example Kabat, Chothia, or MacCallum et al., (see, for example, Kabat et al., In "Sequences of Proteins of Immunological Interest," U.S. Department of Health and Human Services, 1983; Chothia et al., J. Mol. Biol., 1987, 196, 901-917; and MacCallum et al., J. Mol. Biol., 1996, 262, 732-745).

The amino acid residue positions which typically encompass the CDRs as described by each of the above cited references are set forth below for comparison.

| CDR Definitions | | | | |
| --- | --- | --- | --- | --- |
| | Kabat | Chothia | MacCallum | 5c8 |
| VH CDR1 | 31-35 | 26-32 | 30-35 | 26-35 |
| VH CDR2 | 50-65 | 53-55 | 47-58 | 50-66 |
| VH CDR3 | 95-102 | 96-101 | 93-101 | 99-107 |
| VL CDR1 | 24-34 | 26-32 | 30-36 | 24-38 |
| VL CDR2 | 50-56 | 50-52 | 46-55 | 54-60 |
| VL CDR3 | 89-97 | 91-96 | 89-96 | 93-101 |

The phrase "framework region", as used herein, includes the antibody sequence that is between and separates the CDRs. Therefore, a variable region framework is between about 100 to 120 amino acids in length but is intended to reference only those amino acids outside of the CDRs. For the specific example of a heavy chain variable region and for the CDRs as defined by Kabat et al., framework region 1 corresponds to the domain of the variable region encompassing amino acids 1 to 30; region 2 corresponds to the domain of the variable region encompassing amino acids 36 to 49; region 3 corresponds to the domain of the variable region encompassing amino acids 66 to 94, and region 4 corresponds to the domain of the variable region from amino acids 103 to the end of the variable region. The framework regions for the light chain are similarly separated by each of the light claim variable region CDRs. Similarly, using the definition of CDRs by Chothia et al. or McCallum et al. the framework region boundaries are separated by the respective CDR termini as described above.

The phrase "variable region", as used herein, includes the amino terminal portion of an antibody which confers antigen binding onto the molecule and which is not the constant region. The term is intended to include functional fragments, for example, antigen-binding fragments, which maintain some or all of the binding function of the whole variable region.

The phrase "5c8 antibody" refers to an antibody that binds CD154 and is claimed and described in U.S. Pat. No. 5,474,771. The hu5c8 mAb hyridoma is available from the ATCC (HB 10916). The wild-type amino acid sequence for the light chain and heavy chain variable regions of the 5c8 antibody are set forth in SEQ ID NO:1 and SEQ ID NO:4, respectively.

In one aspect, the present invention provides 5c8 antibody derivatives comprising at least one amino acid substitution in a variable region of the light chain. The wild type 5c8 light chain variable region is set forth in SEQ ID NO:1 (amino acid sequence). The present invention provides peptides comprising the wild type 5c8 light chain variable region wherein at least one amino acid substitution is made (i.e, the peptides do not comprise SEQ ID NO:1). The light chain peptide can comprise the entire light chain, including both the constant region and the variable region, or may comprise only the variable region. The light chain peptide can also comprise the entire variable region and a portion of the constant region, which can range from the entire constant region less one amino acid to just one amino acid of the constant region, or any range therewithin. Alternately, the light chain peptide can comprise the variable region fused to any unrelated peptide sequence, thus forming a fusion protein.

In some embodiments, the light chain peptide comprises at least one amino acid substitution in any of the following positions of the wild type 5c8 antibody light chain variable region (see SEQ ID NO:1): positions selected from the group consisting of 24, 26, 27, 28, 30, 31, 32, 33, 34, 35, 36, 38, 54, 57, 58, 59, 60, 93, 95, 96, 97, 98, 100, and 101, or any subset thereof. Such a peptide comprising these positions which may contain an amino acid substitution is set forth in SEQ ID NO:3 (amino acid sequence). These light chain peptides can also comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, or at least 23 amino acid substitutions, or a substitution in each of the 24 positions.

In some embodiments, the light chain peptide comprises at least one amino acid substitution in any of positions 26, 27, 31, 32, 33, and 98, or any subset thereof. Such a peptide comprising these positions which may contain an amino acid substitution is set forth in SEQ ID NO:3 (amino acid sequence), wherein positions 24, 28, 30, 34, 35, 36, 38, 54, 57, 58, 59, 60, 93, 95, 96, 97, 100, and 101 are wild type amino acids. These peptides can also comprise at least 2, at least 3, at least 4, or at least 5 amino acid substitutions, or a substitution in each of the 6 positions.

The substituted amino acid in each of the foregoing positions (i.e., positions 24, 26, 27, 28, 30, 31, 32, 33, 34, 35, 36, 38, 54, 57, 58, 59, 60, 93, 95, 96, 97, 98, 100, and 101) can each be, independently, any naturally occurring amino acid or any non-naturally occurring amino acid. Thus, a particular light chain peptide may comprise one or more amino acid substitutions that are naturally occurring amino acids and/or one or more amino acid substitutions that are non-naturally occurring amino acids.

Individual amino acid substitutions are selected from any one of the following: 1) the set of amino acids with nonpolar sidechains, for example, Ala, Cys, Ile, Leu, Met, Phe, Pro, Val; 2) the set of amino acids with negatively charged side chains, for example, Asp, Glu; 3) the set of amino acids with positively charged sidechains, for example, Arg, His, Lys; and 4) the set of amino acids with uncharged polar sidechains, for example, Asn, Cys, Gln, Gly, His, Met, Phe, Ser, Thr, Trp, Tyr, to which are added Cys, Gly, Met and Phe.

Naturally occurring amino acids include, for example, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val).

Non-naturally occurring amino acids include, for example, norleucine, ornithine, norvaline, homoserine, and other amino acid residue analogues such as those described in Ellman et al., Meth. Enzym., 1991, 202, 301-336. To generate such non-naturally occurring amino acid residues, the procedures of Noren et al., Science, 1989, 244, 182 and Ellman et al., supra, can be used. Briefly, these procedures involve chemically activating a suppressor tRNA with a non-naturally occurring amino acid residue followed by in vitro transcription and translation of the RNA.

In some embodiments, the light chain peptide comprises an amino acid sequence that is at least 70%, at least 75%, at least 80%, at least 85%, at least 90%, or at least 95% identical to a corresponding region of SEQ ID NO:3. Thus, for example, a light chain peptide that comprises two amino acid substitutions at positions 26 and 27 can still have additional substitutions elsewhere in the peptide (i.e., at positions other than those denoted "Xaa" in SEQ ID NO:3) so long as the peptide is at least within the stated percentage of being identical. Thus, peptides having additional amino acid substitutions or amino acid insertions or deletions are contemplated herein. It is to be understood that when determining the percent identity of a peptide that comprises a portion of the constant region of the light chain, only the variable region is considered for percent identity purposes (i.e, the constant region portion is not included within the percent identity).

The fragment can comprise at least 8, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, or at least 105 amino acids, with a maximum of 110 amino acids. In some embodiments, the fragment comprises at least one of positions 24, 26, 27, 28, 30, 31, 32, 33, 34, 35, 36, 38, 54, 57, 58, 59, 60, 93, 95, 96, 97, 98, 100, and 101, or any subset thereof, referring to SEQ ID NO:3. In some embodiments, the fragment comprises one or more of any of the foregoing light chain amino acid substitutions.

The light chain peptides, and fragments thereof, described herein retain their ability to bind to CD154. That is, replacement of the corresponding wild type amino acids of 5c8 antibody with the peptides or fragments described herein will still allow the resultant antibody to bind human CD 154. For example, replacement of all or a portion of the wild type 5c8 light chain variable region amino acids with the corresponding amino acids of a peptide or fragment described herein will result in an antibody that retains the ability to bind human CD154.

In some embodiments, the light chain may be substituted with the following types of amino acids at the indicated positions: R24 (negative, positive, polar, nonpolar); S26 (negative, polar, nonpolar); Q27 (positive, negative, polar); R28 (negative, polar, nonpolar); S30 (positive, negative, polar); S31 (positive, polar, nonpolar); S32 (positive, polar, nonpolar); T33 (positive, negative, polar, nonpolar); Y34 (positive, negative, polar, nonpolar); S35 (polar); Y 36 (polar, nonpolar, negative); H38 (positive, negative, polar, nonpolar); Y54 (negative, polar, nonpolar); N57 (negative, polar); L58 (negative, polar); E59 (negative, polar); S60 (negative); Q93 (positive, negative, polar, nonpolar); S95 (negative, polar); W96 (negative, positive, polar); E97 (negative); I98 (negative, polar, nonpolar); P100 (negative, polar); and T101 (negative, polar, nonpolar).

In some embodiments, the amino acid at position 24 (referring to SEQ ID NO:3) of a light chain peptide, or fragment thereof, is selected from the group consisting of Arg, Asn, Cys, Gln, Gly, His, Met, Phe, Ser, Thr, Trp, Tyr, Ala, Ile, Leu, Pro, Val, Asp, Glu, and Lys, or any subset thereof. The amino acid at position 24 can also be preferably Arg.

In some embodiments, the amino acid at position 26 (referring to SEQ ID NO:3) of a light chain peptide, or fragment thereof, is selected from the group consisting of Ser, Asn, Cys, Gln, Gly, His, Met, Phe, Thr, Trp, Tyr, Ala, Ile, Leu, Pro, Val, Asp, and Glu, or any subset thereof. Alternately, the amino acid at position 26 are preferably Ser or Asp. The amino acid at position 26 can also be preferably Ser, Asp or Glu; or preferably Ser or Asp.

In some embodiments, the amino acid at position 27 (referring to SEQ ID NO:3) of a light chain peptide, or fragment thereof, is selected from the group consisting of Gln, Asn, Cys, Gly, His, Met, Phe, Ser, Thr, Trp, Tyr, Asp, Glu, Arg, and Lys, or any subset thereof. Alternately, the amino acid at position 27 are preferably Gln or Glu. The amino acid at position 27 can also be preferably Gln, Asp, or Glu; or preferably Gln or Glu.

In some embodiments, the amino acid at position 28 (referring to SEQ ID NO:3) of a light chain peptide, or fragment thereof, is selected from the group consisting of Arg, Asn, Cys, Gln, Gly, His, Met, Phe, Ser, Thr, Trp, Tyr, Asp, Glu, Ala, Ile, Leu, Pro, and Val, or any subset thereof. Alternately, the amino acid at position 28 are preferably Arg or Glu. The amino acid at position 28 can also be preferably Arg.

In some embodiments, the amino acid at position 30 (referring to SEQ ID NO:3) of a light chain peptide, or fragment thereof, is selected from the group consisting of Ser, Asn, Cys, Gln, Gly, His, Met, Phe, Thr, Trp, Tyr, Asp, Glu, Arg, and Lys, or any subset thereof. The amino acid at position 30 can also be preferably Ser.

In some embodiments, the amino acid at position 31 (referring to SEQ ID NO:3) of a light chain peptide, or fragment thereof, is selected from the group consisting of Ser, Asn, Cys, Gln, Gly, His, Met, Phe, Thr, Trp, Tyr, Ala, Ile, Leu, Pro, Val, Arg, and Lys, or any subset thereof. Alternately, the amino acid at position 31 is selected from the group consisting of Ser, Ala, His, Asn, Thr, Val, and Trp. The amino acid at position 31 is also selected from the group consisting of Ser, Asn, Cys, Gln, Gly, Thr, and Tyr; or is preferably Ser or Asn.

In some embodiments, the amino acid at position 32 (referring to SEQ ID NO:3) of a light chain peptide, or fragment thereof, is selected from the group consisting of Ser, Asn, Cys, Gln, Gly, His, Met, Phe, Thr, Trp, Tyr, Arg, Ala, Ile, Leu, and Lys, or any subset thereof. Alternately, the amino acid at position 32 is selected from the group consisting of Ser, Ala, Phe, Ile, Leu, Met, and Trp. The amino acid at position 32 is also selected from the group consisting of Ser, Ala, Ile, Leu, Met, Phe, Pro, Val, and Trp; or is preferably Ser or Phe.

In some embodiments, the amino acid at position 33 (referring to SEQ ID NO:3) of a light chain peptide, or fragment thereof, is selected from the group consisting of Thr, Asn, Cys, Gln, Gly, His, Met, Phe, Ser, Trp, Tyr, Asp, Glu, Arg, Ala, Val, and Lys, or any subset thereof. Alternately, the amino acid at position 33 is selected from the group consisting of Thr, Ala, Phe, Met, Val, Trp, Asp, Arg, Tyr, and Gln. The amino acid at position 33 is also selected from the group consisting of Thr, Asn, Cys, Gln, Gly, Ser, and Tyr; or is preferably Thr, Gln, or Tyr.

In some embodiments, the amino acid at position 34 (referring to SEQ ID NO:3) of a light chain peptide, or fragment thereof, is selected from the group consisting of Tyr, Asn, Cys, Gln, Gly, His, Met, Phe, Ser, Thr, Trp Ala, Ile, Leu, Pro, Val, Asp, Glu, Arg, and Lys, or any subset thereof. Alternately, the amino acid at position 34 is selected from the group consisting of Tyr, Ala, Asp, Glu, Phe, Ile, Lys, Leu, Met, Arg, Val, and Trp. The amino acid at position 34 can also be preferably Tyr.

In some embodiments, the amino acid at position 35 (referring to SEQ ID NO:3) of a light chain peptide, or fragment thereof, is selected from the group consisting of Ser, Asn, Cys, Gln, Gly, His, Met, Phe, Thr, Trp, and Tyr, or any subset thereof. The amino acid at position 35 can also be preferably Ser.

In some embodiments, the amino acid at position 36 (referring to SEQ ID NO:3) of a light chain peptide, or fragment thereof, is selected from the group consisting of Tyr, Asn, Cys, Gln, Gly, His, Met, Phe, Ser, Thr, Trp Asp, Ala, Leu, and Glu, or any subset thereof. Alternately, the amino acid at position 36 is selected from the group consisting of Tyr, Ala, Phe, Leu, and Trp. The amino acid at position 36 can also be preferably Tyr.

In some embodiments, the amino acid at position 38 (referring to SEQ ID NO:3) of a light chain peptide, or fragment thereof, is selected from the group consisting of His, Asn, Cys, Gln, Gly, Met, Phe, Ser, Thr, Trp, Tyr, Ala, Ile, Leu, Pro, Val, Asp, Glu, Arg, and Lys, or any subset thereof. The amino acid at position 38 can also be preferably His.

In some embodiments, the amino acid at position 54 (referring to SEQ ID NO:3) of a light chain peptide, or fragment thereof, is selected from the group consisting of Tyr, Asn, Cys, Gln, Gly, His, Met, Phe, Ser, Thr, Trp Ala, Ile, Leu, Pro, Val, Asp, and Glu, or any subset thereof. Alternately, the amino acid at position 54 are preferably Tyr or Glu. The amino acid at position 54 can also be preferably Tyr.

In some embodiments, the amino acid at position 57 (referring to SEQ ID NO:3) of a light chain peptide, or fragment thereof, is selected from the group consisting of Asn, Cys, Gln, Gly, His, Met, Phe, Ser, Thr, Trp, Tyr, Asp, and Glu, or any subset thereof. The amino acid at position 57 can also be preferably Asn.

In some embodiments, the amino acid at position 58 (referring to SEQ ID NO:3) of a light chain peptide, or fragment thereof, is selected from the group consisting of Leu, Asn, Cys, Gln, Gly, His, Met, Phe, Ser, Thr, Trp Asp, and Glu, or any subset thereof. The amino acid at position 58 can also be preferably Leu.

In some embodiments, the amino acid at position 59 (referring to SEQ ID NO:3) of a light chain peptide, or fragment thereof, is selected from the group consisting of Glu, Asn, Cys, Gln, Gly, His, Met, Phe, Ser, Thr, Trp, Tyr, and Asp, or any subset thereof. The amino acid at position 59 can also be preferably Glu.

In some embodiments, the amino acid at position 60 (referring to SEQ ID NO:3) of a light chain peptide, or fragment thereof, is selected from the group consisting of Ser, Asp, and Glu, or any subset thereof. The amino acid at position 60 can also be preferably Ser.

In some embodiments, the amino acid at position 93 (referring to SEQ ID NO:3) of a light chain peptide, or fragment thereof, is selected from the group consisting of Gln, Asn, Cys, Gly, His, Met, Phe, Ser, Thr, Trp, Tyr, Ala, Ile, Leu, Pro, Val, Asp, Glu, Arg, and Lys, or any subset thereof. The amino acid at position 93 can also be preferably Gln.

In some embodiments, the amino acid at position 95 (referring to SEQ ID NO:3) of a light chain peptide, or fragment thereof, is selected from the group consisting of Ser, Asn, Cys, Gln, Gly, His, Met, Phe, Thr, Trp, Tyr, Asp, and Glu, or any subset thereof. The amino acid at position 95 can also be preferably Ser.

In some embodiments, the amino acid at position 96 (referring to SEQ ID NO:3) of a light chain peptide, or fragment thereof, is selected from the group consisting of Trp, Asn, Cys, Gln, Gly, His, Met, Phe, Ser, Thr, Tyr, Asp, Glu, Arg, and Lys, or any subset thereof. Alternately, the amino acid at position 96 is selected from the group consisting of Trp, Asp, Glu, His, Arg, Ser, and Thr. The amino acid at position 96 can also be preferably Trp.

In some embodiments, the amino acid at position 97 (referring to SEQ ID NO:3) of a light chain peptide, or fragment thereof, is Glu or Asp, or any subset thereof. The amino acid at position 97 can also be preferably Glu.

In some embodiments, the amino acid at position 98 (referring to SEQ ID NO:3) of a light chain peptide, or fragment thereof, is selected from the group consisting of Ile, Asn, Cys, Gln, Gly, His, Met, Phe, Ser, Thr, Trp, Tyr, Asp, Ala, Leu, Pro, Val, and Glu, or any subset thereof. Alternately, the amino acid at position 98 selected from the group consisting of Ile, Ala, Phe, His, Leu, Met, Asn, Pro, Gln, Ser, Thr, Val, Trp, and Tyr. The amino acid at position 98 is selected from the group consisting of Ile, Asn, Cys, Gln, Gly, Ser, Thr, and Tyr; or preferably Ile or Gln.

In some embodiments, the amino acid at position 100 (referring to SEQ ID NO:3) of a light chain peptide, or fragment thereof, is selected from the group consisting of Pro, Asn, Cys, Gln, Gly, His, Met, Phe, Ser, Thr, Trp, Tyr, Asp, and Glu, or any subset thereof. The amino acid at position 100 can also be preferably Pro.

In some embodiments, the amino acid at position 101 (referring to SEQ ID NO:3) of a light chain peptide, or fragment thereof, is selected from the group consisting of Thr, Asn, Cys, Gln, Gly, His, Met, Phe, Ser, Trp, Tyr, Ala, Ile, Leu, Pro, Val, Asp, and Glu, or any subset thereof. The amino acid at position 101 can also be preferably Thr.

In some embodiments, the amino acid at position is 26 Asp; the amino acid at position 27 is Glu; the amino acid at position 28 is Glu; the amino acid at position 31 is Val; the amino acid at position 33 is Asp or Arg; and the amino acid at position 54 is Glu.

In some embodiments, the amino acid at position 31 is His or Asn; the amino acid at position 32 is Trp or Phe; the amino acid at position 33 is Trp, Tyr, or Gln; the amino acid at position 36 is Leu or Trp; the amino acid at position 96 is His; and the amino acid at position 98 is Phe or Gln.

In some embodiments, the peptide comprises SEQ ID NO:3 wherein the amino acid at position 26 is Asp; the amino acid at position 27 is Gln; the amino acid at position 31 and position 32 is Ser; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr. This mutant is referred to as Mutant #6 herein.

In some embodiments, the peptide comprises SEQ ID NO:3 wherein the amino acid at position 26, position 31, and position 32 is Ser; the amino acid at position 27 is Glu; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr. This mutant is referred to as mutant #7 herein.

In some embodiments, the peptide comprises SEQ ID NO:3 wherein the amino acid at position 26 is Asp; the amino acid at position 27 is Glu; the amino acid at position 31 and position 32 is Ser; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr. This mutant is referred to as Mutant #14 herein.

In some embodiments, the peptide comprises SEQ ID NO:3 wherein the amino acid at position 27 and position 93 is Gln; the amino acid at position 26, position 31, position 32, position 30, position 35, position 60, and position 95 is Ser; the amino acid at position 33 and position 101 is Thr; the amino acid at position 98 is Ile; the amino acid at position 24 and position 28 is Arg; the amino acid at position 34 and position 54 is Tyr; the amino acid at position 38 is His; the amino acid at position 57 is Asn; the amino acid at position 58 is Leu; the amino acid at position 59 and position 97 is Glu; the amino acid at position 96 and position 36 is Trp; and the amino acid at position 100 is Pro. This mutant is referred to as Mutant #3 herein.

In some embodiments, the peptide comprises SEQ ID NO:3 wherein the amino acid at position 27 and position 93 is Gln; the amino acid at position 26, position 31, position 32, position 30, position 35, position 60, and position 95 is Ser; the amino acid at position 101 is Thr; the amino acid at position 98 is Ile; the amino acid at position 24 and position 28 is Arg; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 96 and position 33 is Trp; and the amino acid at position 100 is Pro. This mutant is referred to as Mutant #5 herein.

In some embodiments, the peptide comprises SEQ ID NO:3 wherein the amino acid at position 27 and position 93 is Gln; the amino acid at position 26, position 32, position 30, position 35, position 60, and position 95 is Ser; the amino acid at position 33 and position 101 is Thr; the amino acid at position 98 is Ile; the amino acid at position 24 and position 28 is Arg; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 96 is Trp; the amino acid at position 31 is Val; and the amino acid at position 100 is Pro. This mutant is referred to as Mutant #8 herein.

In some embodiments, the peptide comprises SEQ ID NO:3 wherein the amino acid at position 27 and position 93 is Gln; the amino acid at position 26, position 31, position 32, position 30, position 35, position 60, and position 95 is Ser; the amino acid at position 101 is Thr; the amino acid at position 98 is Ile; the amino acid at position 24 and position 28 is Arg; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 96 is Trp; the amino acid at position 33 is Asp; and the amino acid at position 100 is Pro. This mutant is referred to as Mutant #9 herein.

In some embodiments, the peptide comprises SEQ ID NO:3 wherein the amino acid at position 27 and position 93 is Gln; the amino acid at position 26, position 31, position 32, position 30, position 35, position 60, and position 95 is Ser; the amino acid at position 33 and position 101 is Thr; the amino acid at position 98 is Ile; the amino acid at position 24 and position 28 is Arg; the amino acid at position 34 and position 36 is Tyr; the amino acid at position 38 is His; the amino acid at position 57 is Asn; the amino acid at position 58 is Leu; the amino acid at position 54, position 59 and position 97 is Glu; the amino acid at position 96 is Trp; and the amino acid at position 100 is Pro. This mutant is referred to as Mutant #10 herein.

In some embodiments, the peptide comprises SEQ ID NO:3 wherein the amino acid at position 26 is Asp; the amino acid at position 27 is Glu; the amino acid at position 31 and position 32 is Ser; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 33 and position 96 is Trp; the amino acid at position 100 is Pro; and the amino acid at position 101 is Thr. This mutant is referred to as Mutant #15 herein.

In some embodiments, the peptide comprises SEQ ID NO:3 wherein the amino acid at position 26 is Asp; the amino acid at position 27 is Gln; the amino acid at position 31 and position 32 is Ser; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26, position 31, and position 32 is Ser; the amino acid at position 27 is Glu; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26 and position 32 is Ser; the amino acid at position 27 is Gln; the amino acid at position 31 is Asn; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26 and position 31 is Ser; the amino acid at position 27 is Gln; the amino acid at position 32 is Phe; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26, position 31, and position 32 is Ser; the amino acid at position 27 and position 33 is Gln; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26, position 31, and position 32 is Ser; the amino acid at position 27 is Gln; the amino acid at position 33 is Tyr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26, position 31, and position 32 is Ser; the amino acid at position 27 and position 98 is Gln; the amino acid at position 33 is Thr; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr.

In some embodiments, the peptide comprises SEQ ID NO:3 wherein the amino acid at position 26 is Asp; the amino acid at position 27 is Glu; the amino acid at position 31 is Asn; the amino acid at position 32 is Ser; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr. This peptide is also referred to herein as the "S26D/Q27E/S31N" peptide.

In some embodiments, the peptide comprises SEQ ID NO:3 wherein the amino acid at position 26 is Asp; the amino acid at position 27 is Glu; the amino acid at position 31 is Ser; the amino acid at position 32 is Phe; the amino acid at position 33 is Thr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr. This peptide is also referred to herein as the "S26D/Q27E/S32F" peptide.

In some embodiments, the peptide comprises SEQ ID NO:3 wherein the amino acid at position 26 is Asp; the amino acid at position 27 is Glu; the amino acid at position 31 and position 32 is Ser; the amino acid at position 33 is Gln; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr. This peptide is also referred to herein as the "S26D/Q27E/T33Q" peptide.

In some embodiments, the peptide comprises SEQ ID NO:3 wherein the amino acid at position 26 is Asp; the amino acid at position 27 is Glu; the amino acid at position 31 and position 32 is Ser; the amino acid at position 33 is Tyr; the amino acid at position 98 is Ile; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr. This peptide is also referred to herein as the "S26D/Q27E/T33Y" peptide.

In some embodiments, the peptide comprises SEQ ID NO:3 wherein the amino acid at position 26 is Asp; the amino acid at position 27 is Glu; the amino acid at position 31 and position 32 is Ser; the amino acid at position 33 is Thr; the amino acid at position 98 is Gln; the amino acid at position 24 and position 28 is Arg; the amino acid at position 30, position 35, position 60, and position 95 is Ser; the amino acid at position 34, position 36, and position 54 is Tyr; the amino acid at position 38 is His; the amino acid at position 57 is Asn; the amino acid at position 58 is Leu; the amino acid at position 59 and position 97 is Glu; the amino acid at position 93 is Gln; the amino acid at position 96 is Trp; the amino acid at position 100 is Pro; and the amino acid at position 101 is Thr. This peptide is also referred to herein as the "S26D/Q27E/I98Q" peptide.

In another aspect, the present invention provides 5c8 antibody derivatives comprising at least one amino acid substitution in a variable region of the heavy chain. The wild type 5c8 heavy chain variable region is set forth in SEQ ID NO:4 (amino acid sequence). The present invention provides peptides comprising the wild type 5c8 heavy chain variable region wherein at least one amino acid substitution is made (i.e, the peptides do not comprise SEQ ID NO:4). The heavy chain peptide can comprise the entire heavy chain, including both the constant region (CH1 and/or CH2 and/or CH3) and the variable region, or may comprise only the variable region. The heavy chain peptide can also comprise the entire variable region and a portion of the constant region, which can range from the entire constant region less one amino acid to just one amino acid of the constant region, or any range therewithin. Alternately, the heavy chain peptide can comprise the variable region fused to any unrelated peptide sequence, thus forming a fusion protein.

In some embodiments, the heavy chain peptide comprises at least one amino acid substitution in any of the following positions of the wild type 5c8 antibody heavy chain variable region (see SEQ ID NO:4): positions selected from the group consisting of 28, 30, 31, 32, 33, 35, 50, 52, 53, 54, 55, 57, 58, 59, 60, 61, 62, 63, 64, 65, 66, 99, 100, 101, 102, 103, 104, 105, 106, and 107, or any subset thereof. Such a peptide comprising these positions which may contain an amino acid substitution is set forth in SEQ ID NO:6 (amino acid sequence). These heavy chain peptides can also comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, or at least 29 amino acid substitutions, or an amino acid substitution in each of the 30 positions.

In some embodiments, the heavy chain peptide comprises at least one amino acid substitution in any of positions 31, 54, 57, 101, and 103, or any subset thereof. Such a peptide comprising these positions which may contain an amino acid substitution is set forth in SEQ ID NO:6 (amino acid sequence), wherein positions 28, 30, 32, 33, 35, 50, 52, 53, 55, 58, 59, 60, 61, 62, 63, 64, 65, 66, 99, 100, 102, 104, 105, 106, and 107 are wild type amino acids. These peptides can also comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, or at least 24 amino acid substitutions, or an amino acid substitution in each of the 25 positions.

The substituted amino acid in each of the foregoing positions (i.e., positions 28, 30, 31, 32, 33, 35, 50, 52, 53, 54, 55, 57, 58, 59, 60, 61, 62, 63, 64, 65, 66, 99, 100, 101, 102, 103, 104, 105, 106, and 107) can each be, independently, any naturally occurring amino acid or any non-naturally occurring amino acid. Thus, a particular heavy chain peptide may comprise one or more amino acid substitutions that are naturally occurring amino acids and/or one or more amino acid substitutions that are non-naturally occurring amino acids.

In some embodiments, the heavy chain peptide comprises an amino acid sequence that is at least 70%, at least 75%, at least 80%, at least 85%, at least 90%, or at least 95% identical to SEQ ID NO:6. Thus, for example, a heavy chain peptide that comprises an amino acid substitution at position 31 can still have additional substitutions elsewhere in the peptide (i.e., at positions other than those denoted "Xaa" in SEQ ID NO:6) so long as the peptide is at least within the stated percentage of being identical. Thus, peptides having additional amino acid substitutions or amino acid insertions or deletions are contemplated herein. It is to be understood that when determining the percent identity of a peptide that comprises a portion of the constant region of the heavy chain, only the variable region is considered for percent identity purposes (i.e, the constant region portion is not included within the percent identity).

In some embodiments, a fragment of a heavy chain peptide that comprises an amino acid sequence at least 70%, at least 75%, at least 80%, at least 85%, at least 90%, or at least 95% identical to a corresponding region of SEQ ID NO:6 is provided.

The fragment can comprise at least 8, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, or at least 115 amino acids, with a maximum of 117 amino acids. In some embodiments, the fragment comprises at least one of positions 28, 30, 31, 32, 33, 35, 50, 52, 53, 54, 55, 57, 58, 59, 60, 61, 62, 63, 64, 65, 66, 99, 100, 101, 102, 103, 104, 105, 106, and 107, or any subset thereof, referring to SEQ ID NO:6. In some embodiments, the fragment comprises one or more of any of the foregoing heavy chain amino acid substitutions.

The heavy chain peptides, and fragments thereof, described herein retain their ability to bind to CD154. That is, replacement of the corresponding wild type amino acids of 5c8 antibody with the peptides or fragments described herein will still allow the resultant antibody to bind human CD 154. For example, replacement of all or a portion of the wild type 5c8 heavy chain variable region amino acids with the corresponding amino acids of a peptide or fragment described herein will result in an antibody that retains the ability to bind human CD154. In some embodiments, the antibodies described herein may contact one or more less residues of CD154 than the wild type 5c8 antibody.

In some embodiments, the heavy chain may be substituted with the following types of amino acids at the indicated positions: I28 (positive, negative, polar); T30 (positive, negative, polar, nonpolar); S31 (positive, polar); Y32 (positive, negative, polar, nonpolar); Y33 (positive, negative, polar, nonpolar); Y35 (polar); E50 (negative); N52 (polar, nonpolar); P53 (negative, polar); S54 (positive, negative, polar); N55 (negative, polar, nonpolar); D57 (negative, nonpolar); T58 (polar, nonpolar); N59 (negative, polar, nonpolar); F60 (negative, positive, polar, nonpolar); N61 (negative); E62 (negative); K63 (negative, positive, polar, nonpolar); F64 (negative, polar, nonpolar); K65 (negative, positive, polar, nonpolar); S66 (negative); S99 (negative, nonpolar); D100 (negative); G101 (nonpolar); R102 (positive, polar); N103 (negative, positive, polar, nonpolar); D104 (negative); M105 (negative, polar, positive); D106 (negative); and S107 (negative, polar, nonpolar).

In some embodiments, the amino acid at position 28 (referring to SEQ ID NO:6) of a heavy chain peptide, or fragment thereof, is selected from the group consisting of Ile, Asp, Glu, Arg, Lys, Asn, Cys, Gln, Gly, His, Met, Phe, Ser, Thr, and Trp, or any subset thereof. Alternately, the amino acid at position 28 is selected from the group consisting of Ile, His, Asn, Gln, Ser, Thr, and Glu. The amino acid at position 28 can also be preferably Ile.

In some embodiments, the amino acid at position 30 (referring to SEQ ID NO:6) of a heavy chain peptide, or fragment thereof, is selected from the group consisting of Thr, Asp, Glu, Arg, Lys, Asn, Cys, Gln, Gly, His, Met, Phe, Ser, Trp, Tyr, Ala, Ile, Leu, Pro, and Val, or any subset thereof. Alternately, the amino acid at position 30 is selected from the group consisting of Thr, His, Asn, Gln, Ser, Tyr, and Arg. The amino acid at position 30 can also be preferably Thr.

In some embodiments, the amino acid at position 31 (referring to SEQ ID NO:6) of a heavy chain peptide, or fragment thereof, is selected from the group consisting of Ser, Arg, His, Lys, Gln, and Trp, or any subset thereof. Alternately, the amino acid at position 31 are preferably Ser, Gln, or Trp. The amino acid at position 31 selected from the group consisting of Ser, Ala, Ile, Leu, Met, Phe, Pro, Val, Trp, Asn, Cys, Gln, Gly, Ser, Thr, and Tyr; or preferably is Ser, Trp, or Gln.

In some embodiments, the amino acid at position 32 (referring to SEQ ID NO:6) of a heavy chain peptide, or fragment thereof, is selected from the group consisting of Tyr, Asp, Glu, Arg, Lys, Asn, Cys, Gln, Gly, His, Met, Phe, Ser, Trp, Ala, Ile, Leu, Pro, and Val, or any subset thereof. The amino acid at position 32 can also be preferably Tyr.

In some embodiments, the amino acid at position 33 (referring to SEQ ID NO:6) of a heavy chain peptide, or fragment thereof, is selected from the group consisting of Tyr, Asp, Glu, Asn, Cys, Gln, Gly, His, Met, Phe, Ser, Thr, Trp Ala, Ile, Leu, Pro, and Val, or any subset thereof. Alternately, the amino acid at position 33 is selected from the group consisting of Tyr, Ala, Pro, Ser, Thr, Val, and Trp. The amino acid at position 33 can also be preferably Tyr.

In some embodiments, the amino acid at position 35 (referring to SEQ ID NO:6) of a heavy chain peptide, or fragment thereof, is selected from the group consisting of Tyr, Asn, Cys, Gln, Gly, His, Met, Phe, Ser, Thr, Trp Asp, and Glu, or any subset thereof. The amino acid at position 35 can also be preferably Tyr.

In some embodiments, the amino acid at position 50 (referring to SEQ ID NO:6) of a heavy chain peptide, or fragment thereof, is Glu or Asp, or any subset thereof. The amino acid at position 50 can also be preferably Glu.

In some embodiments, the amino acid at position 52 (referring to SEQ ID NO:6) of a heavy chain peptide, or fragment thereof, is selected from the group consisting of Asn, Cys, Gln, Gly, His, Met, Phe, Ser, Thr, Trp, Tyr, Arg, Ala, Leu, Val, and Lys, or any subset thereof. Alternately, the amino acid at position 52 is selected from the group consisting of Asn, Ala, Phe, His, Leu, Met, Ser, Thr, Val, and Trp. The amino acid at position 52 can also be preferably Asn.

In some embodiments, the amino acid at position 53 (referring to SEQ ID NO:6) of a heavy chain peptide, or fragment thereof, is selected from the group consisting of Pro, Asn, Cys, Gln, Gly, His, Met, Phe, Ser, Thr, Trp, Tyr, Asp, and Glu, or any subset thereof. The amino acid at position 53 can also be preferably Pro.

In some embodiments, the amino acid at position 54 (referring to SEQ ID NO:6) of a heavy chain peptide, or fragment thereof, is selected from the group consisting of Ser, Asn, Cys, Gln, Gly, His, Met, Phe, Thr, Trp, Tyr, Arg, Lys, and Glu, or any subset thereof. Alternately, the amino acid at position 54 is selected from the group consisting of Ser, Glu, His, Lys, Asn, Gln, Arg, Thr, Trp, Tyr, and Phe. The amino acid at position 54 is also selected from the group consisting of Ser, Ala, Ile, Leu, Met, Phe, Pro, Val, Trp, Asn, Cys, Gln, Gly, Ser, Thr, and Tyr; or preferably Ser, Phe, or Gln.

In some embodiments, the amino acid at position 55 (referring to SEQ ID NO:6) of a heavy chain peptide, or fragment thereof, is selected from the group consisting of Asn, Glu, Lys, Gln, Ser, Thr, Met, and Val, or any subset thereof. Alternately, the amino acid at position 55 selected from the group consisting of Asn, Glu, Lys, Gln, Ser, Thr, Met, and Val. The amino acid at position 55 can also be preferably Asn.

In some embodiments, the amino acid at position 57 (referring to SEQ ID NO:6) of a heavy chain peptide, or fragment thereof, is selected from the group consisting of Asp, Glu, Phe, and Leu, or any subset thereof. Alternately, the amino acid at position 57 are preferably Asp, Phe, or Leu. The amino acid at position 57 selected from the group consisting of Asp, Ala, Ile, Leu, Met, Phe, Pro, Val, and Trp; or is preferably Asp, Leu, or Phe.

In some embodiments, the amino acid at position 58 (referring to SEQ ID NO:6) of a heavy chain peptide, or fragment thereof, is selected from the group consisting of Thr, Asn, Cys, Gln, Gly, His, Met, Phe, Ser, Trp, Tyr, Ala, Ile, Leu, Pro, and Val, or any subset thereof. The amino acid at position 58 can also be preferably Thr.

In some embodiments, the amino acid at position 59 (referring to SEQ ID NO:6) of a heavy chain peptide, or fragment thereof, is selected from the group consisting of Asn, Cys, Gln, Gly, His, Met, Phe, Ser, Thr, Trp, Tyr, Ala, Ile, Leu, Pro, Val, Asp, and Glu, or any subset thereof. Alternately, the amino acid at position 59 selected from the group consisting of Asn, Ala, Phe, Leu, Met, Pro, Val, Trp, Asp, and Tyr. The amino acid at position 59 can also be preferably Asn.

In some embodiments, the amino acid at position 60 (referring to SEQ ID NO:6) of a heavy chain peptide, or fragment thereof, is selected from the group consisting of Phe, Asp, Asn, Cys, Gln, Gly, His, Met, Ser, Thr, Trp, Tyr, Asp, Glu, Arg, Lys, Ala, Ile, Leu, Pro, and Val, or any subset thereof. The amino acid at position 60 can also be preferably Phe.

In some embodiments, the amino acid at position 61 (referring to SEQ ID NO:6) of a heavy chain peptide, or fragment thereof, is Asn, Asp, or Glu, or any subset thereof. The amino acid at position 61 can also be preferably Asn.

In some embodiments, the amino acid at position 62 (referring to SEQ ID NO:6) of a heavy chain peptide, or fragment thereof, is Glu or Asp, or any subset thereof. The amino acid at position 62 can also be preferably Glu.

In some embodiments, the amino acid at position 63 (referring to SEQ ID NO:6) of a heavy chain peptide, or fragment thereof, is selected from the group consisting of Lys, Asn, Cys, Gln, Gly, His, Met, Phe, Ser, Thr, Trp, Tyr, Arg, Glu, Asp, Ala, Ile, Leu, Pro, and Val, or any subset thereof. The amino acid at position 63 can also be preferably Lys.

In some embodiments, the amino acid at position 64 (referring to SEQ ID NO:6) of a heavy chain peptide, or fragment thereof, is selected from the group consisting of Phe, Asn, Cys, Gln, Gly, His, Met, Ser, Thr, Trp, Tyr, Asp, Glu, Ala, Ile, Leu, Pro, and Val, or any subset thereof. The amino acid at position 64 can also be preferably Phe.

In some embodiments, the amino acid at position 65 (referring to SEQ ID NO:6) of a heavy chain peptide, or fragment thereof, is selected from the group consisting of Lys, Asn, Cys, Gln, Gly, His, Met, Phe, Ser, Thr, Trp, Tyr, Arg, Asp, Glu, Ala, Ile, Leu, Pro, and Val, or any subset thereof. The amino acid at position 65 can also be preferably Lys.

In some embodiments, the amino acid at position 66 (referring to SEQ ID NO:6) of a heavy chain peptide, or fragment thereof, is Ser, Asp, or Glu, or any subset thereof. The amino acid at position 66 can also be preferably Ser.

In some embodiments, the amino acid at position 99 (referring to SEQ ID NO:6) of a heavy chain peptide, or fragment thereof, is Ser, Asp, Glu, or Ala, or any subset thereof. Alternately, the amino acid at position 99 are preferably Ser or Ala. The amino acid at position 99 can also be preferably Ser.

In some embodiments, the amino acid at position 100 (referring to SEQ ID NO:6) of a heavy chain peptide, or fragment thereof, is Asp or Glu, or any subset thereof. The amino acid at position 100 can also be preferably Asp.

In some embodiments, the amino acid at position 101 (referring to SEQ ID NO:6) of a heavy chain peptide, or fragment thereof, is Gly, Phe, or Leu, or any subset thereof. Alternately, the amino acid at position 101 are preferably Gly, Phe, or Leu. The amino acid at position 101 selected from the group consisting of Gly, Ala, Ile, Leu, Met, Phe, Pro, Val, and Trp; or is preferably Gly, Leu, or Phe.

In some embodiments, the amino acid at position 102 (referring to SEQ ID NO:6) of a heavy chain peptide, or fragment thereof, is selected from the group consisting of Arg, Asn, Cys, Gln, Gly, His, Met, Phe, Ser, Thr, Trp, Tyr, and Lys, or any subset thereof. The amino acid at position 102 can also be preferably Arg.

In some embodiments, the amino acid at position 103 (referring to SEQ ID NO:6) of a heavy chain peptide, or fragment thereof, is selected from the group consisting of Asn, Cys, Gln, Gly, His, Met, Phe, Ser, Thr, Trp, Tyr, Asp, Glu, Ala, Ile, Lys, Arg, and Val, or any subset thereof. Alternately, the amino acid at position 103 is selected from the group consisting of Asn, Ala, Asp, Glu, Phe, His, Ile, Lys, Met, Arg, Ser, Thr, Val, and Tyr. The amino acid at position 103 is also selected from the group consisting of Asn, Cys, Gln, Gly, Ser, Thr, and Tyr; or preferably Asn or Tyr.

In some embodiments, the amino acid at position 104 (referring to SEQ ID NO:6) of a heavy chain peptide, or fragment thereof, is Asp or Glu, or any subset thereof. The amino acid at position 104 can also be preferably Asp.

In some embodiments, the amino acid at position 105 (referring to SEQ ID NO:6) of a heavy chain peptide, or fragment thereof, is selected from the group consisting of Met, Asp, Glu, Arg, His, Lys, Asn, Cys, Gln, Gly, Phe, Ser, Thr, Trp, and Tyr, or any subset thereof. The amino acid at position 105 can also be preferably Met.

In some embodiments, the amino acid at position 106 (referring to SEQ ID NO:6) of a heavy chain peptide, or fragment thereof, is Asp or Glu, or any subset thereof. The amino acid at position 106 can also be preferably Asp.

In some embodiments, the amino acid at position 107 (referring to SEQ ID NO:6) of a heavy chain peptide, or fragment thereof, is selected from the group consisting of Ser, Asn, Cys, Gln, Gly, His, Met, Phe, Thr, Trp, Tyr, Asp, Glu, Ala, Ile, Leu, Pro, and Val, or any subset thereof. The amino acid at position 107 can also be preferably Ser.

In some embodiments, the amino acid at position 28 is Glu; the amino acid at position 33 is Phe; the amino acid at position 54 is Thr; and the amino acid at position 59 is Asp or Leu.

In some embodiments, the amino acid at position 30 is His or Arg; the amino acid at position 31 is Gln or Trp; the amino acid at position 33 is Trp, Val, or Pro; the amino acid at position 52 is Met or Trp; the amino acid at position 54 is Asn, Phe, or Gln; the amino acid at position 55 is Met, Lys, or Val; the amino acid at position 57 is Phe or Leu; the amino acid at position 59 is Phe or Tyr; the amino acid at position 101 is Phe or Leu; and the amino acid at position 103 is His or Tyr.

In some embodiments, the peptide comprises SEQ ID NO:6 wherein the amino acid at position 31, position 54, position 66, position 99, and position 107 is Ser; the amino acid at position 57, position 100, position 104, and position 106 is Asp; the amino acid at position 101 is Gly; the amino acid at position 103, position 52, position 55, position 59, and position 61 is Asn; the amino acid at position 28 is Ile; the amino acid at position 58 is Thr; the amino acid at position 32, position 33, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; the amino acid at position 30 is His; and the amino acid at position 105 is Met. This mutant is referred to as Mutant #1 herein.

In some embodiments, the peptide comprises SEQ ID NO:6 wherein the amino acid at position 31, position 54, position 66, position 99, and position 107 is Ser; the amino acid at position 57, position 100, position 104, and position 106 is Asp; the amino acid at position 101 is Gly; the amino acid at position 103, position 52, position 55, position 59, and position 61 is Asn; the amino acid at position 28 is Ile; the amino acid at position 30 and position 58 is Thr; the amino acid at position 32, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; the amino acid at position 33 is Trp; and the amino acid at position 105 is Met. This mutant is referred to as Mutant #2 herein.

In some embodiments, the peptide comprises SEQ ID NO:6 wherein the amino acid at position 31, position 66, position 99, and position 107 is Ser; the amino acid at position 57, position 100, position 104, and position 106 is Asp; the amino acid at position 101 is Gly; the amino acid at position 103, position 52, position 54, position 55, position 59, and position 61 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; and the amino acid at position 105 is Met. This mutant is referred to as Mutant #4 herein.

In some embodiments, the peptide comprises SEQ ID NO:6 wherein the amino acid at position 31, position 54, position 66, position 99, and position 107 is Ser; the amino acid at position 57, position 100, position 104, and position 106 is Asp; the amino acid at position 101 is Gly; the amino acid at position 103, position 52, position 55, position 59, and position 61 is Asn; the amino acid at position 28 is Ile; the amino acid at position 30 and position 58 is Thr; the amino acid at position 32, and position 35 is Tyr; the amino acid at position 50 and position 62 is Glu; the amino acid at position 53 is Pro; the amino acid at position 33, position 60, and position 64 is Phe; the amino acid at position 63 and position 65 is Lys; the amino acid at position 102 is Arg; and the amino acid at position 105 is Met. This mutant is referred to as Mutant #11 herein.

In some embodiments, the peptide comprises SEQ ID NO:6 wherein the amino acid at position 31, position 54, position 66, position 99, and position 107 is Ser; the amino acid at position 57, position 59, position 100, position 104, and position 106 is Asp; the amino acid at position 101 is Gly; the amino acid at position 103, position 52, position 55, and position 61 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; and the amino acid at position 105 is Met. This mutant is referred to as Mutant #12 herein.

In some embodiments, the peptide comprises SEQ ID NO:6 wherein the amino acid at position 31, position 54, position 66, position 99, and position 107 is Ser; the amino acid at position 57, position 100, position 104, and position 106 is Asp; the amino acid at position 101 is Gly; the amino acid at position 103, position 52, position 55, and position 61 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; the amino acid at position 59 is Leu; and the amino acid at position 105 is Met. This mutant is referred to as Mutant #13 herein.

In some embodiments, the peptide comprises SEQ ID NO:6 wherein the amino acid at position 31 is Trp; the amino acid at position 54 is Ser; the amino acid at position 57 is Asp; the amino acid at position 101 is Gly; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 is Gln; the amino acid at position 54 is Ser; the amino acid at position 57 is Asp; the amino acid at position 101 is Gly; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 is Ser; the amino acid at position 54 is Phe; the amino acid at position 57 is Asp; the amino acid at position 101 is Gly; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 is Ser; the amino acid at position 54 is Gln; the amino acid at position 57 is Asp; the amino acid at position 101 is Gly; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 and position 54 is Ser; the amino acid at position 57 is Phe; the amino acid at position 101 is Gly; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 and position 54 is Ser; the amino acid at position 57 is Leu; the amino acid at position 101 is Gly; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 and position 54 is Ser; the amino acid at position 57 is Asp; the amino acid at position 101 is Phe; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 and position 54 is Ser; the amino acid at position 57 is Asp; the amino acid at position 101 is Leu; the amino acid at position 103 is Asn; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

In some embodiments, the peptide comprises SEQ ID NO:6 wherein the amino acid at position 31 and position 54 is Ser; the amino acid at position 57 is Asp; the amino acid at position 101 is Gly; the amino acid at position 103 is Tyr; the amino acid at position 28 is Ile; the amino acid at position 30 and position 58 is Thr; the amino acid at position 32, position 33, and position 35 is Tyr; the amino acid at position 50 and position 62 is Glu; the amino acid at position 52, position 55, position 59, and position 61 is Asn; the amino acid at position 53 is Pro; the amino acid at position 60 and position 64 is Phe; the amino acid at position 63 and position 65 is Lys; the amino acid at position 66, position 99, and position 107 is Ser; the amino acid at position 100, position 104, and position 106 is Asp; the amino acid at position 102 is Arg; and the amino acid at position 105 is Met.

Identity or similarity with respect to this sequence is defined herein as the percentage of amino acid residues in the modified sequence that are identical (i.e., same residue) with the wild type 5c8 antibody residues, after aligning the sequences and introducing gaps, if necessary, to achieve the maximum percent sequence identity. Typically, N-terminal, C-terminal, or internal extensions, deletions, or insertions into the antibody sequence outside of the variable domain are not construed as affecting sequence identity or similarity. The antibody can comprise one or more amino acid alterations in or adjacent to one or more hypervariable regions thereof. Percent sequence identity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The present invention also provides nucleic acid molecules encoding any of the peptides, or fragments thereof, described herein. A nucleic acid molecule encoding the peptide of SEQ ID NO:3 is set forth in SEQ ID NO:2. A nucleic acid molecule encoding the peptide of SEQ ID NO:6 is set forth in SEQ ID NO:5. One skilled in the art having the amino acid sequences of the peptides disclosed herein can design and prepare nucleic acid molecules encoding the peptides.

The present invention also provides vectors comprising any nucleic acid molecule that encodes any of the peptides, or fragments thereof, described herein. One skilled in the art is readily familiar with numerous vectors, many of which are commercially available.

The present invention also provides host cells comprising any of the nucleic acid molecules or vectors disclosed herein. The host cells can be used, for example, to express the peptides and antibodies, or fragments of thereof. The peptides and antibodies, or fragments thereof, can also be expressed in cells in vivo. The host cell that is transformed (for example, transfected) to produce the peptides and antibodies, or fragments of thereof can be an immortalised mammalian cell line, such as those of lymphoid origin (for example, a myeloma, hybridoma, trioma or quadroma cell line). The host cell can also include normal lymphoid cells, such as B-cells, that have been immortalized by transformation with a virus (for example, the Epstein-Barr virus).

Some immortalized lymphoid cell lines, such as myeloma cell lines, in their normal state, secrete isolated Ig light or heavy chains. If such a cell line is transformed with a vector that expresses a mutant antibody, or fragment thereof, prepared during the process of the invention, it may not be necessary to carry out the remaining steps of the process, provided that the normally secreted chain is complementary to the variable domain of the Ig chain encoded by the vector prepared earlier. If the immortalised cell line, however, does not secrete or does not secrete a complementary chain, it will be necessary to introduce into the cells a vector that encodes the appropriate complementary chain or fragment thereof.

In the case where the immortalised cell line secretes a complementary light or heavy chain, the transformed cell line may be produced for example by transforming a suitable bacterial cell with the vector and then fusing the bacterial cell with the immortalised cell line (for example, by spheroplast fusion). Alternatively, the DNA may be directly introduced into the immortalised cell line by electroporation.

In some embodiments of this invention, the host cells include, but are not limited to: bacterial cells, such as *E. coli, Caulobacter crescentus, Streptomyces* species, and *Salmonella typhimurium*; yeast cells, such as *Saccharomyces cerevisiae, Schizosaccharomyces pombe, Pichia pastoris, Pichia methanolica*; insect cell lines, such as those from *Spodoptera frugiperda* (for example, Sf9 and Sf21 cell lines, and expresSF™ cells (Protein Sciences Corp., Meriden, Conn., USA)), *Drosophila* S2 cells, and *Trichoplusia* in High Five® Cells (Invitrogen, Carlsbad, Calif., USA); and mammalian cells, such as COS1 and COS7 cells, Chinese hamster ovary (CHO) cells, NS0 myeloma cells, NIH 3T3 cells, 293 cells, HEPG2 cells, HeLa cells, L cells, HeLa, MDCK, HEK293, WI38, murine ES cell lines (for example, from strains 129/SV, C57/BL6, DBA-1, 129/SVJ), K562, Jurkat cells, and BW5147. Other useful mammalian cell lines are well known and readily available from the American Type Culture Collection ("ATCC") (Manassas, Va., USA) and the National Institute of General Medical Sciences (NIGMS) Human Genetic Cell Repository at the Coriell Cell Repositories (Camden, N.J., USA). These cell types are only representative and are not meant to be an exhaustive list.

The peptides or antibodies, and fragments thereof, can be produced in prokaryotic and eukaryotic cells. The invention, thus, also provides cells that express the antibodies of the present invention, including hybridoma cells, B cells, plasma cells, as well as host cells recombinantly modified to express the antibodies of the present invention.

Among other considerations, some of which are described above, a host cell strain may be chosen for its ability to process the expressed peptide or antibody, or fragment thereof, in the desired fashion. Post-translational modifications of the polypeptide include, but are not limited to, glycosylation, acetylation, carboxylation, phosphorylation, lipidation, and acylation, and it is an aspect of the present invention to provide antibodies or fragments thereof with one or more of these post-translational modifications.

The present invention also provides antibodies, or fragments thereof, comprising any peptide described herein, wherein the antibody or fragment thereof can bind to human CD154. In some embodiments, the antibody, or fragment thereof, comprises any of the light chain peptides, or fragments thereof, described herein. In other embodiments, the antibody, or fragment thereof, comprises any of the heavy chain peptides, or fragments thereof, described herein. In yet other embodiments, the antibody, or fragment thereof, comprises any of the heavy chain peptides, or fragments thereof, described herein and any of the light chain peptides, or fragments thereof, described herein.

In some embodiments, the antibody, or fragment thereof, comprises a first peptide which is a peptide of Mutant #14, and a second peptide which is a peptide of mutant #1. Such a composite mutant is referred to as Mutant #16 herein.

In some embodiments, the antibody, or fragment thereof, comprises a first peptide which is a peptide of Mutant #15, and a second peptide which is a peptide of mutant #2. Such a composite mutant is referred to as Mutant #17 herein.

In some embodiments, the antibody, or fragment thereof, comprises a first peptide which is a peptide of Mutant #15, and a second peptide which is a peptide of mutant #1. Such a composite mutant is referred to as Mutant #18 herein.

In some embodiments, the antibody, or fragment thereof, comprises a first peptide which is a peptide of Mutant #14, and a second peptide which is a peptide of mutant #4. Such a composite mutant is referred to as Mutant #19 herein.

In some embodiments, the antibody, or fragment thereof, comprises a first peptide which is a peptide of Mutant #15, and a second peptide which is a peptide of mutant #4. Such a composite mutant is referred to as Mutant #20 herein.

In some embodiments, the antibody, or fragment thereof, comprises a first peptide which is a peptide of Mutant #14, and a second peptide which is a peptide of mutant #2. Such a composite mutant is referred to as Mutant #23 herein.

In some embodiments, the antibody, or fragment thereof, comprises a first peptide which is a peptide of Mutant #14, and a second peptide that comprises SEQ ID NO:6 wherein the amino acid at position 31, position 66, position 99, and position 107 is Ser; the amino acid at position 57, position 100, position 104, and position 106 is Asp; the amino acid at position 101 is Gly; the amino acid at position 103, position 52, position 54, position 55, position 59, and position 61 is Asn; the amino acid at position 28 is Ile; the amino acid at position 58 is Thr; the amino acid at position 32, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; the amino acid at position 30 is His; the amino acid at position 33 is Trp; and the amino acid at position 105 is Met. Such a composite mutant is referred to as Mutant #21 herein.

In some embodiments, the antibody, or fragment thereof, comprises a first peptide which is a peptide of Mutant #15, and a second peptide that comprises SEQ ID NO:6 wherein the amino acid at position 31, position 66, position 99, and position 107 is Ser; the amino acid at position 57, position 100, position 104, and position 106 is Asp; the amino acid at position 101 is Gly; the amino acid at position 103, position 52, position 54, position 55, position 59, and position 61 is Asn; the amino acid at position 28 is Ile; the amino acid at position 58 is Thr; the amino acid at position 32, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; the amino acid at position 30 is His; the amino acid at position 33 is Trp; and the amino acid at position 105 is Met. Such a composite mutant is referred to as Mutant #22 herein.

In some embodiments, the antibody, or fragment thereof, comprises a first peptide which is a peptide of Mutant #14, and a second peptide that comprises SEQ ID NO:6 wherein the amino acid at position 31, position 54, position 66, position 99, and position 107 is Ser; the amino acid at position 57, position 100, position 104, and position 106 is Asp; the amino acid at position 101 is Gly; the amino acid at position 103, position 52, position 55, position 59, and position 61 is Asn; the amino acid at position 28 is Ile; the amino acid at position 58 is Thr; the amino acid at position 32, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; the amino acid at position 30 is His; the amino acid at position 33 is Trp; and the amino acid at position 105 is Met. Such a composite mutant is referred to as Mutant #24 herein.

In some embodiments, the antibody, or fragment thereof, comprises a first peptide which is a peptide of Mutant #15, and a second peptide that comprises SEQ ID NO:6 wherein the amino acid at position 31, position 54, position 66, position 99, and position 107 is Ser; the amino acid at position 57, position 100, position 104, and position 106 is Asp; the amino acid at position 101 is Gly; the amino acid at position 103, position 52, position 55, position 59, and position 61 is Asn;

the amino acid at position 28 is Ile; the amino acid at position 58 is Thr; the amino acid at position 32, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; the amino acid at position 30 is His; the amino acid at position 33 is Trp; and the amino acid at position 105 is Met. Such a composite mutant is referred to as Mutant #25 herein.

In some embodiments, the antibody, or fragment thereof, comprises a first peptide which is a peptide of Mutant #15, and a second peptide that comprises SEQ ID NO:6 wherein the amino acid at position 31, position 66, position 99, and position 107 is Ser; the amino acid at position 57, position 100, position 104, and position 106 is Asp; the amino acid at position 101 is Gly; the amino acid at position 103, position 52, position 54, position 55, position 59, and position 61 is Asn; the amino acid at position 28 is Ile; the amino acid at position 58 is Thr; the amino acid at position 32, position 33, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; the amino acid at position 30 is His; and the amino acid at position 105 is Met. Such a composite mutant is referred to as Mutant #26 herein.

In some embodiments, the antibody, or fragment thereof, comprises a first peptide which is a peptide of Mutant #15, and a second peptide that comprises SEQ ID NO:6 wherein the amino acid at position 31, position 66, position 99, and position 107 is Ser; the amino acid at position 57, position 100, position 104, and position 106 is Asp; the amino acid at position 101 is Gly; the amino acid at position 103, position 52, position 54, position 55, position 59, and position 61 is Asn; the amino acid at position 28 is Ile; the amino acid at position 30 and position 58 is Thr; the amino acid at position 32, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; the position at amino acid 33 is Trp; and the amino acid at position 105 is Met. Such a composite mutant is referred to as Mutant #27 herein.

In some embodiments, the antibody, or fragment thereof, comprises a first peptide which is a peptide of Mutant #14, and a second peptide that comprises SEQ ID NO:6 wherein the amino acid at position 31, position 66, position 99, and position 107 is Ser; the amino acid at position 57, position 100, position 104, and position 106 is Asp; the amino acid at position 101 is Gly; the amino acid at position 103, position 52, position 54, position 55, position 59, and position 61 is Asn; the amino acid at position 28 is Ile; the amino acid at position 30 and position 58 is Thr; the amino acid at position 32, and position 35 is Tyr; the amino acid at position 50 and position 62 is Glu; the amino acid at position 53 is Pro; the amino acid at position 60 and position 64 is Phe; the amino acid at position 63 and position 65 is Lys; the amino acid at position 102 is Arg; the position at amino acid 33 is Trp; and the amino acid at position 105 is Met. Such a composite mutant is referred to as Mutant #28 herein.

An antibody is a glycoprotein of approximate MW 150 kD that is produced by the humoral arm of the immune system of vertebrates in the body in response to the presence of foreign molecules in the body. A functional antibody or antibody derivative is able to recognize and bind to its specific antigen in vitro or in vivo, and may initiate any subsequent actions associated with antibody-binding, including for example, direct cytotoxicity, complement-dependent cytotoxicity ("CDC"), antibody-dependent cytotoxicity ("ADCC"), and antibody production.

Upon binding to the antigen, antibodies activate one or more of the many effector systems of the immune system that contribute to the neutralization, destruction and elimination of the infecting microorganism or other antigen-containing entity, for example, a cancer cell.

The antibodies, and fragments thereof, disclosed herein have increased or decreased affinity, avidity, and/or specificity as compared to the wild type 5c8 antibody. In some embodiments, the antibodies, and fragments thereof, disclosed herein have increased affinity, avidity, and/or specificity as compared to the wild type 5c8 antibody. Affinity, avidity, and/or specificity can be measured in a variety of ways. Generally, and regardless of the precise manner in which affinity is defined or measured, the methods of the invention improve antibody affinity when they generate an antibody that is superior in any aspect of its clinical application to the antibody (or antibodies) from which it was made (for example, the methods of the invention are considered effective or successful when a modified antibody can be administered at a lower dose or less frequently or by a more convenient route of administration than an antibody (or antibodies) from which it was made).

Those of ordinary skill in the art will recognize that determining affinity is not always as simple as looking at a single, bottom-line figure. Since antibodies have two arms, their apparent affinity is usually much higher than the intrinsic affinity between the variable region and the antigen. Intrinsic affinity can be measured using scFv or Fab fragments.

In some embodiments, the antibody fragment is a single chain antibody (scFv), a F(ab')$_2$ fragment, a Fab fragment, a Fab' fragment, or an Fd fragment, or antigen-binding fragments thereof. A single chain antibody is made up of variable regions linked by protein spacers in a single protein chain. In other embodiments, the antibody fragments include heteromeric antibody complexes and antibody fusions, such as bispecific antibodies, hemidimeric antibodies, and multivalent antibodies (such as tetravalent antibodies). A hemidimeric antibody is made up of an Fc portion and one Fab portion.

In some embodiments, the antibodies, or fragments thereof, can also include proteins containing one or more immunoglobulin light chains and/or heavy chains, such as monomers and homo- or hetero-multimers (for example, dimers or trimers) of these chains, where these chains are optionally disulfide-bonded or otherwise cross-linked. These antibodies, or fragments thereof, can bind to one or more antigens.

The fragments of antibodies disclosed herein retain their ability to bind CD154. For example, for a fragment of 5c8 that is able to bind to CD154, the corresponding fragment which comprises any mutation disclosed herein is also able to bind CD154 Amino acids present on CD154 that are contacted by 5c8 include: V126, I127, S128, E129, A130, S131, S132, K133, T134, Q139, W140, A141, E142, K143, G144, Y145, Y146, T147, M148, S149, N150, N151, V153, T154, L155, E156, N157, G158, K159, T176, F177, C178, S179, N180, E182, A183, S184, R200, F201, E202, R203, I204, L205, A209, A215, K216, P217, C218, G219, Q220, Q221, D243, P244, S245, Q246, V247, S248, H249, G250, T251, G252, F253, and T254. In some embodiments, some or all of these residues on CD154 interact with the mutants described herein. In some embodiments, the mutants described herein may contact one or more less residues of CD154 than the wild type antibody.

In some embodiments, the antibody, or fragment thereof, is labeled with a detectable marker. Detectable markers include, but are not limited to, radioactive isotopes (such as $P^{32}$ and $S^{35}$), enzymes (such as horseradish peroxidase, chloramphenicol acetyltransferase (CAT), β-galactosidase (β-gal), and the like), fluorochromes, chromophores, colloidal gold, dyes, and biotin. The labeled antibodies, or fragments thereof, can be used to carry out diagnostic procedures (many diagnostic assays rely on detection of a protein antigen (such as PSA)) in a variety of cell or tissue types. For imaging procedures, in vitro or in vivo, the altered antibodies produced by the methods described herein can be labeled with additional agents, such as NMR contrasting agents, X-ray contrasting agents, or quantum dots. Methods for attaching a detectable agent to polypeptides, including antibodies or fragments thereof, are known in the art. The antibodies can also be attached to an insoluble support (such as a bead, a glass or plastic slide, or the like).

In some embodiments, the antibody, or fragment thereof, is conjugated to a therapeutic agent which includes, but are not limited to, radioisotopes (such as $^{111}$In or $^{90}$Y), toxins (such as tetanus toxoid or ricin), toxoids, and chemotherapeutic agents (see, U.S. Pat. No. 6,307,026).

In some embodiments, the antibodies, or fragments thereof, modified by being conjugated to an imaging agent. Imaging agents include, for example, a labeling moiety (such as biotin, fluorescent moieties, radioactive moieties, histidine tag or other peptide tags) for easy isolation or detection.

When administered, antibodies are often cleared rapidly from the circulation and may therefore elicit relatively short-lived pharmacological activity. Consequently, frequent injections of relatively large doses of antibodies may be required to sustain the therapeutic efficacy of the antibody treatment.

In some embodiments, the antibodies, or fragments thereof, can be modified (such as by attachment to other moieties) to increase the integrity and longevity of the antibody in vivo. For example, the antibodies, or fragments thereof, can be modified to include a moiety that can increase stabilization, thereby prolonging the serum half-life of the antibody.

In some embodiments, the antibody, or fragment thereof, comprises at least one high molecular-weight polymer which include, but are not limited to, polyethyleneimine and polylysine. In other embodiments, the antibodies, or fragments thereof, are modified by the covalent attachment of water-soluble polymers, such as polyethylene glycol, copolymers of polyethylene glycol and polypropylene glycol, carboxymethyl cellulose, dextran, polyvinyl alcohol, polyvinylpyrrolidone or polyproline, all of which are known to exhibit substantially longer half-lives in blood following intravenous injection than do the corresponding unmodified proteins (Abuchowski et al., In: "Enzymes as Drugs", 1981; Holcenberg et al., Ed., 1981, Wiley-Interscience, New York, N.Y., 367-383; Anderson, Human Gene Therapy. Science, 1992, 256, 808-813; Newmark et al., J. Appl. Biochem., 1982, 4, 185-189; and Katre et al., Proc. Natl. Acad. Sci. USA, 1987, 84, 1487-1491).

In some embodiments, the antibody, or fragment thereof, is PEGylated or glycosylated in at least one amino acid position or modified by other suitable water-soluble polymers including, but are not limited to, PEG, copolymers of ethylene glycol/propylene glycol, carboxymethylcellulose, dextran, polyvinyl alcohol, polyvinyl pyrrolidone, poly 1,3 dioxolane, poly 1,3,6 trioxane, ethylene/maleic anhydride copolymer, polyamino acids (either homopolymers or random copolymers), and dextran or poly(n vinyl pyrrolidone) PEG, propropylene glycol homopolymers, polypropylene oxide/ethylene oxide co polymers, polyoxyethylated polyols (e.g., glycerol), polyvinyl alcohol, and mixtures thereof.

The polymer may be of any suitable molecular weight, and may be branched or unbranched.

For PEG, suitable average molecular weight is between about 2 kDa and about 100 kDa. This provides for ease in handling and manufacturing. Those of skill in the art will appreciate that in preparations of PEG, some molecules will weigh more, some less, than the stated molecular weight. Thus, molecular weight is typically specified as "average molecular weight." Other molecular weights (sizes) may be used, depending on the desired therapeutic profile (e.g., the duration of sustained release desired; the effects, if any, on biological activity; the ease in handling; the degree or lack of antigenicity and other known effects of PEG on a therapeutic protein). In various embodiments, the molecular weight is about 2 kDa, about 5 kDa, about 10 kDa, about 15 kDa, about 20 kDa, about 25 kDa, about 30 kDa, about 40 kDa or about 100 kDa. In some embodiments, the average molecular weight of each PEG chain is about 20 kDa. In other embodiments, the average molecular weight is about 10 kDa.

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of PEGs). The proportion of polymer molecules to protein (or polypeptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono, di-, tri-, etc.), the molecular weight of the polymer selected, whether the polymer is branched or unbranched, and the reaction conditions.

The PEG molecules (or other chemical moieties) should be attached to the protein with consideration of effects on functional or antigenic domains of the protein. There are a number of attachment methods available to those skilled in the art. See, for example, EP 0 401384 (coupling PEG to G CSF); Malik et al., Exp. Hematol., 1992, 20, 1028-1035 (reporting PEGylation of GM CSF using tresyl chloride).

For example, PEG may be covalently bound (PEGylation) through amino acid residues via a reactive group, such as, a free amino or carboxyl group. The amino acid residues having a free amino group include lysine residues and the amino-terminal amino acid residue. Those having a free carboxyl group include aspartic acid residues, glutamic acid residues, and the C terminal amino acid residue. Sulfhydryl groups may also be used as a reactive group for attaching the PEG molecule(s). For therapeutic purposes, attachment can be at an amino group, for example, at the N terminus or lysine group. One may specifically desire an amino-terminal chemically modified protein.

Using PEG as an illustration of the present compositions, one may select from a variety of PEG molecules (by molecular weight, branching, etc.), the proportion of PEG molecules to protein (or peptide) molecules in the reaction mix, the type of PEGylation reaction to be performed, and the method of obtaining the selected amino-terminally PEGylated protein. The method of obtaining the amino-terminal PEGylated preparation (i.e., separating this moiety from other monoPEGylated moieties if necessary) may be by purification of the amino-terminal PEGylated material from a population of PEGylated protein molecules. Selective amino-terminal chemical modification may be accomplished by reductive alkylation that exploits differential reactivity of different types of primary amino groups (lysine versus the amino-terminal) available for derivatization in a particular protein. Under the appropriate reaction conditions, substantially selective derivatization of the protein at the amino-terminus with a carbonyl group containing polymer is achieved. For example, one may selectively PEGylate the amino-terminus of the protein by performing the reaction at a pH which allows one to take advantage of the pKa differences between the epsilon (∈) amino group of the lysine residues and that of the alpha (α) amino group of the amino-terminal residue of the protein. By such selective derivatization, attachment of a water soluble polymer to a protein is controlled: the conjugation with the polymer takes place predominantly at the amino terminus of the protein and no significant modification of other reactive groups, such as the lysine side chain amino groups, occurs.

Using reductive alkylation, the water-soluble polymer may be of the type described above, and should have a single reactive aldehyde for coupling to the protein. PEG propionaldehyde, containing a single reactive aldehyde, may be used.

Antibody modifications can also increase the protein's solubility in aqueous solution, eliminate aggregation, enhance the physical and chemical stability of the protein, and greatly reduce the immunogenicity and antigenicity of the protein. As a result, the desired in vivo biological activity can be achieved by the administration of such polymer-protein adducts less frequently or in lower doses than with the unmodified protein.

The term "chimeric antibody" is used to describe a protein comprising at least an antigen-binding portion of an immunoglobulin molecule that is attached by, for example, a peptide bond or peptide linker, to a heterologous protein or a peptide thereof. The "heterologous" protein can be a non-immunoglobulin or a portion of an immunoglobulin of a different species, class or subclass.

There are numerous processes by which such antibodies can be made. For example, one can prepare an expression vector including a promoter that is operably linked to a DNA sequence that encodes at least $V_H$ or $V_L$ and a sequence that encodes the heterologous protein (or a peptide thereof (the peptide being of a sufficient length that it can be recognized as a non-immunoglobulin molecule (for example, a peptide having no substantial sequence identity to an immunoglobulin))). If necessary, or desired, one can prepare a second expression vector including a promoter that is operably linked to a DNA sequence that encodes the complementary variable domain (for example, where the parent expression vector encodes $V_H$, the second expression vector encodes $V_L$ and vice versa). A cell line (for example, an immortalized mammalian cell line) can then be transformed with one or both of the expression vectors and cultured under conditions that permit expression of the chimeric variable domain or chimeric antibody (see, for example, International Patent Application No. PCT/GB85/00392). This method can be used to express the modified antibodies of the present invention, antibodies containing full-length heavy and light chains, or fragments thereof (for example, the Fab, F(ab')$_2$, or scFv fragments described herein). The methods are not limited to expression of chimeric antibodies.

Though naturally occurring antibodies are derived from a single species, engineered antibodies and antibody fragments may be derived from more than one species of animal,—for example, chimeric antibodies. To date, mouse (murine)/human chimeric and murine/non-human primate antibodies have been generated, though other species' combinations are possible.

In some embodiments, the antibodies, or fragments thereof, are chimeric antibodies. Typically, chimeric antibodies include the heavy and/or light chain variable regions, including both complementary determining region ("CDR") and framework residues, of one species, (typically mouse) fused to constant regions of another species (typically human). These chimeric mouse/human antibodies contain approximately 75% human and 25% mouse amino acid sequences, respectively. The human sequences represent the constant regions of the antibody, while the mouse sequences represent the variable regions (and thus contain the antigen-binding sites) of the antibody.

The rationale for using such chimeras is to retain the antigen specificity of the mouse antibody but reduce the immunogenicity of the mouse antibody (a mouse antibody would cause an immune response against it in species other than the mouse) and thus be able to employ the chimera in human therapies.

In another embodiment, the antibodies, or fragments thereof, include chimeric antibodies comprising framework regions from one antibody and CDR regions from another antibody. In other embodiments, the antibodies, or fragments thereof, include chimeric antibodies comprising CDR regions from different human antibodies. In other embodiments, the antibodies, or fragments thereof, include chimeric antibodies comprising CDR regions from at least two different human antibodies.

Methods of making all of the chimeric antibodies described above are well known to one of skill in the art (U.S. Pat. No. 5,807,715; Morrison et al., Proc. Natl. Acad. Sci. USA, 1984, 81, 6851-5; Sharon et al., Nature, 1984, 309, 364-7; and Takeda et al., Nature, 1985 314, 452-4).

In another embodiment, the antibodies, or fragments thereof, also include primatized, humanized and fully human antibodies. Primatized and humanized antibodies typically include heavy and/or light chain CDRs from a murine antibody grafted into a non-human primate or human antibody V region framework, usually further comprising a human constant region (Riechmann et al., Nature, 1988, 332, 323-7; Co et al., Nature, 1991, 351, 501-2; and U.S. Pat. Nos. 6,054,297, 5,821,337, 5,770,196, 5,766,886, 5,821,123, 5,869,619, 6,180,377, 6,013,256, 5,693,761, and 6,180,370).

A humanized antibody is an antibody produced by recombinant DNA technology, in which some or all of the amino acids of a human immunoglobulin light or heavy chain that are not required for antigen binding (for example, the constant regions and the framework regions of the variable domains) are used to substitute for the corresponding amino acids from the light or heavy chain of the cognate, nonhuman antibody. By way of example, a humanized version of a murine antibody to a given antigen has on both of its heavy and light chains 1) constant regions of a human antibody; 2) framework regions from the variable domains of a human antibody; and 3) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Humanized antibodies generally are less likely to elicit an immune response in humans as compared to chimeric human antibodies because the former contain considerably fewer non-human components. Methods for making humanized antibodies are well know to those of skill in the art of antibodies (European Patent No. 239400; Jones et al., Nature, 1986, 321, 522-525; Riechmann et al., Nature, 1988, 332, 323-327; Verhoeyen et al., Science, 1988, 239, 1534-1536; Queen et al., Proc. Nat. Acad.

Sci. USA, 1989, 86, 10029; Orlandi et al., Proc. Natl. Acad. Sci. USA, 1989, 86, 3833; and U.S. Pat. No. 6,180,370).

In some embodiments, humanized antibodies are generated by the transplantation of murine (or other non-human) CDRs onto a human antibody. More specifically, this can be achieved as follows: 1) the cDNAs encoding heavy and light chain variable domains are isolated from a hybridoma; 2) the DNA sequences of the variable domains, including the CDRs, are determined by sequencing; 3) the DNAs encoding the CDRs are transferred to the corresponding regions of a human antibody heavy or light chain variable domain coding sequence by site directed mutagenesis; and 4) the human constant region gene segments of a desired isotype (for example, 1 for CH and k for CL) are added. Finally, the humanized heavy and light chain genes are co-expressed in mammalian host cells (for example, CHO or NS0 cells) to produce soluble humanized antibody.

At times, direct transfer of CDRs to a human framework leads to a loss of antigen-binding affinity of the resultant antibody. This is because in some cognate antibodies, certain amino acids within the framework regions interact with the CDRs and thus influence the overall antigen binding affinity of the antibody. In such cases, it would be critical to introduce "back mutations" in the framework regions of the acceptor antibody in order to retain the antigen-binding activity of the cognate antibody. The general approaches of making back mutations is well known to those of skill in the art (Queen et al., Proc. Nat. Acad. Sci. USA, 1989, 86, 10029; and Co et al., Proc. Nat. Acad. Sci. USA, 1991, 88, 2869-2873; PCT patent application WO 90/07861; and Tempest, Biotechnology, 1991, 9, 266-271).

In some embodiments, the antibodies, or fragments thereof, are fully human anti-CD154 antibodies. The fully human antibodies can be prepared using in vitro-primed human splenocytes, (Boerner et al., J. Immunol., 1991, 147, 86-95) or phage-displayed antibody libraries (U.S. Pat. No. 6,300,064). Alternately, the fully human antibodies can be prepared by repertoire cloning (Persson et al., Proc. Nat. Acad. Sci. USA, 1991, 88, 2432-2436; and Huang et al., J. Immunol. Methods, 1991, 141, 227-236). In addition, U.S. Pat. No. 5,798,230 describes preparation of human monoclonal antibodies from human B cells, wherein human antibody-producing B cells are immortalized by infection with an Epstein-Barr virus, or a derivative thereof, that expresses Epstein-Barr virus nuclear antigen 2 ("EBNA2"), a protein required for immortalization. The EBNA2 function is subsequently shut off, resulting in an increase in antibody production.

Other methods for producing fully human antibodies involve the use of non-human animals that have inactivated endogenous Ig loci and are transgenic for un-rearranged human antibody heavy chain and light chain genes. Such transgenic animals can be immunized with activated T cells or the D1.1 protein (U.S. Pat. Nos. 5,474,771; 6,331,433; and 6,455,044) and hybridomas can be generated from B cells derived there from. The details of these methods are described in the art. See, e.g. the various GenPharm/Medarex (Palo Alto, Calif.) publications/patents concerning transgenic mice containing human Ig miniloci, including U.S. Pat. No. 5,789, 650; the various Abgenix (Fremont, Calif.) publications/patents with respect to XENOMOUSE® mice, including U.S. Pat. Nos. 6,075,181, 6,150,584 and 6,162,963; Green et al., Nature Genetics, 1994, 7, 13-21; Mendez et al., Nature Genetics, 1997, 15, 146-56; and the various Kirin (Japan) publications/patents concerning "transomic" mice, including European Patent 843961 and Tomizuka et al., Nature Genetics, 1997 June; 16(2):133-43.

Once the sequence of an antibody (for example, a CDR-grafted or otherwise modified or "humanized" antibody) has been decided upon, that antibody can be made by techniques well known in the art of molecular biology. More specifically, recombinant DNA techniques can be used to produce a wide range of polypeptides by transforming a host cell with a nucleic acid sequence (for example, a DNA sequence that encodes the desired protein products (for example, a modified heavy or light chain; the variable domains thereof, or other antigen-binding fragments thereof)).

More specifically, the methods of production can be carried out as described above for chimeric antibodies. The DNA sequence encoding, for example, an altered variable domain can be prepared by oligonucleotide synthesis. The variable domain can be one that includes the FRs of a human acceptor molecule and the CDRs of a donor, for example, murine, either before or after one or more of the residues (for example, a residue within a CDR) has been modified to facilitate antigen binding. This is facilitated by determining the framework region sequence of the acceptor antibody and at least the CDR sequences of the donor antibody. Alternatively, the DNA sequence encoding the altered variable domain may be prepared by primer directed oligonucleotide site-directed mutagenesis. This technique involves hybridizing an oligonucleotide coding for a desired mutation with a single strand of DNA containing the mutation point and using the single strand as a template for extension of the oligonucleotide to produce a strand containing the mutation. This technique, in various forms, is described by, for example, Zoller and Smith (Nuc. Acids Res., 1982, 10, 6487-6500), Norris et al. (Nuc. Acids Res., 1983, 11, 5103-5112), Zoller and Smith (DNA, 1984, 3, 479-488), and Kramer et al. (Nuc. Acids Res., 1982, 10, 6475-6485).

Other methods of introducing mutations into a sequence are known as well and can be used to generate the altered antibodies described herein (see, for example, Carter et al., Nuc. Acids Res., 1985, 13, 4431-4443). The oligonucleotides used for site-directed mutagenesis can be prepared by oligonucleotide synthesis or isolated from DNA coding for the variable domain of the donor antibody by use of suitable restriction enzymes.

In another embodiment, the antibodies, or fragments thereof, can be prepared by cell free translation. Alternately, the antibodies, or fragments thereof, can be produced in bioreactors containing the antibody-expressing cells, in order to facilitate large scale production.

In some embodiments, the antibodies, or fragments thereof, can be produced in transgenic mammals, such as goats, cows, or sheep, that express the antibody in milk, in order to facilitate large scale production of antibodies (U.S. Pat. No. 5,827,690; and Pollock et al., J. Immunol. Meth., 1999, 231, 147-57).

The present invention also provides compositions comprising any one or more of the peptides, or fragments thereof, any one or more of the nucleic acid molecules or vectors, or any one or more of the antibodies, or fragments thereof, described herein. Compositions include, for example, pharmaceutical compositions.

In prophylactic applications, pharmaceutical compositions or medicaments are administered to a subject suffering from a disorder in an amount sufficient to eliminate or reduce the risk, lessen the severity, or delay the outset of the disorder, including biochemical, histologic and/or behavioral symptoms of the disorder, its complications and intermediate pathological phenotypes presenting during development of the disorder. In therapeutic applications, compositions or medicaments are administered to a subject suspected of, or already suffering from such a disorder in an amount sufficient to cure, or at least partially arrest, the symptoms of the disorder (biochemical, histologic and/or behavioral), including its complications and intermediate pathological phenotypes in development of the disorder.

The pharmaceutical compositions of the invention can include at least one antibody, or fragment thereof, disclosed herein in a pharmaceutically acceptable carrier. A "pharmaceutically acceptable carrier" refers to at least one component of a pharmaceutical preparation that is normally used for administration of active ingredients. As such, a carrier can contain any pharmaceutical excipient used in the art and any form of vehicle for administration. Carriers include, but are not limited to, phosphate buffered saline, physiological saline, water, citrate/sucrose/Tween formulations and emulsions such as, for example, oil/water emulsions.

The compositions can include an active therapeutic agent and a variety of other pharmaceutically acceptable components. See Remington's Pharmaceutical Science (15th ed., Mack Publishing Company, Easton, Pa. (1980)). The desired form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents include, but are not limited to, distilled water, physiological phosphate-buffered saline, Ringer's solutions, dextrose solution, and Hank's solution. In addition, the pharmaceutical composition or formulation may also include other carriers, adjuvants, or non-toxic, nontherapeutic, nonimmunogenic stabilizers and the like. Solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate, and alginic acid. Tablet binders that can be used include acacia, methylcellulose, sodium carboxymethylcellulose, polyvinylpyrrolidone (Povidone™), hydroxypropyl methylcellulose, sucrose, starch, and ethylcellulose. Lubricants that can be used include magnesium stearates, stearic acid, silicone fluid, talc, waxes, oils, and colloidal silica. Additional excipients include, for example, colorants, taste-masking agents, solubility aids, suspension agents, compressing agents, enteric coatings, sustained release aids, and the like.

Antibodies can be administered in the form of a depot injection or implant preparation, which can be formulated in such a manner as to permit a sustained release of the active ingredient. An exemplary composition comprises antibody, or fragment thereof, at 5 mg/ml, formulated in aqueous buffer consisting of 50 mM L-histidine and 150 mM NaCl, adjusted to pH 6.0 with HCl. Another example of a suitable formulation buffer for monoclonal antibodies contains 20 mM sodium citrate, pH 6.0, 10% sucrose, and 0.1% Tween 80.

In some embodiments, liquid formulations of a pharmaceutical composition for oral administration prepared in water or other aqueous vehicles can contain various suspending agents such as methylcellulose, alginates, tragacanth, pectin, kelgin, carrageenan, acacia, polyvinylpyrrolidone, and polyvinyl alcohol. Liquid formulations of pharmaceutical compositions of this invention can also include solutions, emulsions, syrups and elixirs containing, together with the active compound(s), wetting agents, sweeteners, and coloring and flavoring agents. Various liquid and powder formulations of the pharmaceutical compositions can be prepared by conventional methods for inhalation into the lungs of the mammal to be treated.

In some embodiments, liquid formulations of a pharmaceutical composition for injection can comprise various carriers such as vegetable oils, dimethylacetamide, dimethylformamide, ethyl lactate, ethyl carbonate, isopropyl myristate, ethanol, polyols such as, for example, glycerol, propylene glycol, liquid polyethylene glycol, and the like. In some embodiments, the composition includes a citrate/sucrose/tween carrier. For intravenous injections, water soluble versions of the compositions can be administered by the drip method, whereby a pharmaceutical formulation containing the antifungal agent and a physiologically acceptable excipient is infused. Physiologically acceptable excipients can include, for example, 5% dextrose, 0.9% saline, Ringer's solution or other suitable excipients. A suitable insoluble form of the composition can be prepared and administered as a suspension in an aqueous base or a pharmaceutically acceptable oil base, such as an ester of a long chain fatty acid such as, for example, ethyl oleate.

The compositions can be, for example, injectable solutions, aqueous suspensions or solutions, non-aqueous suspensions or solutions, solid and liquid oral formulations, salves, gels, ointments, intradermal patches, creams, lotions, tablets, capsules, sustained release formulations, and the like. In some embodiments, for topical applications, the pharmaceutical compositions can be formulated in a suitable ointment. In some embodiments, a topical semi-solid ointment formulation typically comprises a concentration of the active ingredient from about 1 to 20%, or from 5 to 10%, in a carrier, such as a pharmaceutical cream base. Some examples of formulations of a composition for topical use include, but are not limited to, drops, tinctures, lotions, creams, solutions, and ointments containing the active ingredient and various supports and vehicles.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or microparticles such as polylactide, polyglycolide, or copolymer for enhanced adjuvant effect (see Langer, Science, 1990, 249, 1527 and Hanes, Advanced Drug Delivery Reviews, 1997, 28, 97). A sterile injectable preparation such as, for example, a sterile injectable aqueous or oleaginous suspension can also be prepared. This suspension may be formulated according to techniques known in the art using suitable dispersing, wetting, and suspending agents. In some embodiments, the pharmaceutical composition can be delivered in a microencapsulation device so as to reduce or prevent a host immune response against the protein.

Effective doses of the compositions of the present invention, for the treatment of a condition vary depending upon many different factors, including means of administration, target site, physiological state of the subject, whether the subject is human or an animal, other medications administered, and whether treatment is prophylactic or therapeutic. Usually, the subject is a human but non-human mammals including transgenic mammals can also be treated.

For passive immunization with an antibody, the dosage ranges from about 0.0001 to 100 mg/kg, from about 0.01 and 200 mg/kg, or from about 0.01 to 20 mg/kg of the host body weight. For example, dosages can be 1 mg/kg body weight or 10 mg/kg body weight or within the range of 1 to 10 mg/kg, or at least 1 mg/kg. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1 to 10 mg/kg or 15 mg/kg on consecutive days, 30 mg/kg on alternate days or 60 mg/kg weekly. In some embodiments, two or more antibodies, or fragments thereof, with different binding specificities are administered simultaneously, in which case the dosage of each antibody administered falls within the ranges indicated.

Antibody is usually administered on multiple occasions. Intervals between single dosages can be weekly, monthly or yearly. In some embodiments, dosage is adjusted to achieve a plasma antibody concentration of 1 to 1000 mg/ml and in some methods 25 to 300 μg/ml. Alternately, antibody can be administered as a sustained release formulation, in which case less frequent administration is required. Dosage and frequency vary depending on the half-life of the antibody in the subject. In general, human antibodies show the longest half-life, followed by humanized antibodies, chimeric antibodies, and nonhuman antibodies, in descending order.

The dosage and frequency of administration can vary depending on whether the treatment is prophylactic or therapeutic. In prophylactic applications, compositions containing the present antibodies or a cocktail thereof are administered to a subject not already in the disease state to enhance the subject's resistance. Such an amount is defined to be a "prophylactic effective dose." In this use, the precise amounts again depend upon the subject's state of health and general immunity, but generally range from 0.1 to 25 mg per dose, especially 0.5 to 2.5 mg per dose. A relatively low dosage is administered at relatively infrequent intervals over a long period of time. Some subjects continue to receive treatment for the rest of their lives.

In therapeutic applications, a relatively high dosage (for example, from about 1 to 200 mg of antibody per dose, with dosages of from 5 to 25 mg being more commonly used) at relatively short intervals is sometimes required until progression of the disease is reduced or terminated, and possibly until the subject shows partial or complete amelioration of symptoms of disease. Thereafter, the patent can be administered a prophylactic regime.

In some embodiments, the antibodies, or fragments thereof, or compositions comprising the same, can be administered to a subject by injection intravenously, subcutaneously, intraperitoneally, intramuscularly, intramedullarily, intraventricularly, intraepidurally, intraarterially, intravascularly, intraarticularly, intrasynovially, intrasternally, intrathecally, intrahepatically, intraspinally, intratumorly, intracranially, enteral, intrapulmonary, transmucosal, intrauterine, sublingual, or locally at sites of inflammation or tumor growth by using standard methods. Alternately, the antibodies, or fragments thereof, or compositions comprising the same, can be administered to a subject by routes including oral, nasal, ophthalmic, rectal, or topical. The most typical route of administration of a protein drug is intravascular, subcutaneous, or intramuscular, although other routes can be effective. In some embodiments, antibodies are administered as a sustained release composition or device, such as a Medipad™ device. The protein drug can also be administered via the respiratory tract, for example, using a dry powder inhalation device, nebulizer, or a metered dose inhaler.

In some embodiments, the antibodies, or fragments thereof, can be administered to a subject by sustained release administration, by such means as depot injections of erodible implants directly applied during surgery or by implantation of an infusion pump or a biocompatible sustained release implant into the subject. Alternately, the antibodies, or fragments thereof, can be administered to a subject by injectable depot routes of administration, such as by using 1-, 3-, or 6-month depot injectable or biodegradable materials and methods, or by applying to the skin of the subject a transdermal patch containing the antibody, antibody derivative or pharmaceutical composition, and leaving the patch in contact with the subject's skin, generally for 1 to 5 hours per patch.

The compositions can optionally be administered in combination with other agents that are at least partly effective in treatment of immune disorders. In some embodiments, the pharmaceutical composition further comprises an immunosuppressive or immunomodulatory compound. For example, such an immunosuppressive or immunomodulatory compound may be one of the following: an agent that interrupts T cell costimulatory signaling via CD28; an agent that interrupts calcineurin signaling, a corticosteroid, an anti-proliferative agent, and an antibody that specifically binds to a protein expressed on the surface of immune cells including, but not limited to, CD45, CD2, IL2R, CD4, CD8 and RANK FcR, B7, CTLA4, TNF, LTβ, and VLA-4. In addition, in some embodiments, the immunosuppressive or immunomodulatory compound is tacrolimus, sirolimus, mycophenolate mofetil, mizorubine, deoxyspergualin, brequinar sodium, leflunomide, rapamycin or azaspirane.

The present invention also provides kits comprising any of the antibodies, or fragments thereof, described herein. The kit can include, for example, container, package or dispenser along with labels and instructions for administration or use.

The present invention also provides methods of treating or preventing a CD154-related human disease or disorder. In some embodiments, the method comprises administering to a human a therapeutically- or prophylactically-effective amount of any of the antibodies, or fragments thereof, described herein, or a composition comprising the same, such that the CD154-related human disease or disorder is diminished or prevented. For the purposes of this invention, "administration" means any of the standard methods of administering an antibody, antibody fragment, or composition known to those skilled in the art, and should not be limited to the examples provided herein.

In some embodiments, the subject being treated will have been previously diagnosed as having a disease or condition suitable for treatments disclosed herein. Such subjects will, thus, have been diagnosed as baing in need of treatment. Alternately, the treatment may be intended to treat a particular disease or condition but simultaneously be treating another undiagnosed condition as well.

Treatment of a subject suffering from a disease or disorder can be monitored using standard methods. Some methods entail determining a baseline value, for example, of an antibody level or profile in a subject, before administering a dosage of agent, and comparing this with a value for the profile or level after treatment. A significant increase such as, for example, greater than the typical margin of experimental error in repeat measurements of the same sample, expressed as one standard deviation from the mean of such measurements in value of the level or profile signals a positive treatment outcome (i.e., that administration of the agent has achieved a desired response). If the value for immune response does not change significantly, or decreases, a negative treatment outcome is indicated.

In other embodiments, a control value such as a mean and standard deviation, of level or profile is determined for a control population. Typically the individuals in the control population have not received prior treatment. Measured values of the level or profile in a subject after administering a therapeutic agent are then compared with the control value. A significant increase relative to the control value, such as greater than one standard deviation from the mean, signals a positive or sufficient treatment outcome. A lack of significant increase or a decrease signals a negative or insufficient treatment outcome. Administration of the therapeutic is generally continued while the level is increasing relative to the control value. As before, attainment of a plateau relative to control values is an indicator that the administration of treatment can be discontinued or reduced in dosage and/or frequency.

In other embodiments, a control value of the level or profile, such as a mean and standard deviation, is determined from a control population of individuals who have undergone treatment with a therapeutic agent and whose levels or profiles have plateaued in response to treatment. Measured values of levels or profiles in a subject are compared with the control value. If the measured level in a subject is not significantly different, such as by more than one standard deviation, from the control value, treatment can be discontinued. If the level in a subject is significantly below the control value, continued administration of agent is warranted. If the level in the subject persists below the control value, then a change in treatment may be indicated.

In other embodiments, a subject who is not presently receiving treatment but has undergone a previous course of treatment is monitored for antibody levels or profiles to determine whether a resumption of treatment is required. The measured level or profile in the subject can be compared with a value previously achieved in the subject after a previous course of treatment. A significant decrease relative to the previous measurement, such as greater than a typical margin of error in repeat measurements of the same sample, is an indication that treatment can be resumed. Alternately, the value measured in a subject can be compared with a control value (mean plus standard deviation) determined in a population of subjects after undergoing a course of treatment. Alternately, the measured value in a subject can be compared with a control value in populations of prophylactically treated subjects who remain free of symptoms of disease, or populations of therapeutically treated subjects who show amelioration of disease characteristics. In all of these cases, a significant decrease relative to the control level, such as more than a standard deviation, is an indicator that treatment should be resumed in a subject.

The antibody profile following administration typically shows an immediate peak in antibody concentration followed by an exponential decay. Without a further dosage, the decay approaches pretreatment levels within a period of days to months depending on the half-life of the antibody administered. For example the half-life of some human antibodies is of the order of 20 days.

In some methods, a baseline measurement of antibody to a given antigen in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline, such as 50%, 25% or 10%, administration of a further dosage of antibody is administered. In some embodiments, peak or subsequent measured levels less background are compared with reference levels previously determined to constitute a beneficial prophylactic or therapeutic treatment regime in other subjects. If the measured antibody level is significantly less than a reference level, such as less than the mean minus one standard deviation of the reference value in population of subjects benefiting from treatment, administration of an additional dosage of antibody is indicated.

Additional embodiments include monitoring, over the course of treatment, any art-recognized physiologic symptom, such as physical or mental symptom, routinely relied on by researchers or physicians to diagnose or monitor disorders.

In some embodiments, the antibodies, or fragments thereof, disclosed herein, or a pharmaceutical composition comprising the same, are capable of inhibiting an immune response in a subject. The antibody, antibody derivative or pharmaceutical composition is administered to the subject in an effective inhibiting amount. An "effective inhibiting amount" of an antibody, antibody derivative, such as a CD154-binding fragment, or pharmaceutical composition is any amount which is effective to inhibit the CD154-CD40 interaction in the subject to whom it is administered. Methods of determining an "inhibiting amount" are well known to those skilled in the art and depend upon factors including, but not limited to, the type of subject involved, the size of the subject and the therapeutic agent delivered.

In a particular embodiment, the anti-CD154 antibody, antibody derivative or pharmaceutical composition comprising the antibody or antibody derivative is capable of binding to the CD 154 molecule. In another embodiment, the anti-CD 154 antibody, antibody derivative or pharmaceutical composition comprising the antibody or antibody derivative is capable of inhibiting the immune response by inhibiting the CD154-CD40 interaction.

In some embodiments, the anti-CD154 antibody, antibody derivative or pharmaceutical composition comprising the antibody or antibody derivative is capable of inhibiting inflammation. For the purposes of this invention, inflammatory responses are characterized by redness, swelling, heat and pain, as consequences of capillary dilation with edema and migration of phagocytic leukocytes. Some examples of inflammatory responses include, but are not limited to, arthritis, contact dermatitis, hyper-IgE syndrome, inflammatory bowel disease, allergic asthma, and idiopathic inflammatory disease. Some examples of arthritis include, but are not limited to, rheumatoid arthritis, non-rheumatoid inflammatory arthritis, arthritis associated with Lyme disease and inflammatory osteoarthritis. Some examples of idiopathic inflammatory disease include, but are not limited to, psoriasis and systemic lupus erythematosus. Additional diseases, disorders, and conditions that can be treated using the compounds and/or compositions disclosed herein include, but are not limited to, atherosclerosis, Myasthenia gravis, Graves' disease, idiopathic thrombocytopenia purpura, hemolytic anemia, diabetes mellitus, Crohn's disease, multiple sclerosis, and drug-induced autoimmune diseases, such as drug-induced lupus.

In some embodiments, the compounds and compositions can be used to inhibit rejection by the subject of a transplanted organ such as, for example, a transplanted heart, kidney, liver, skin, pancreatic islet cells or bone marrow. In other embodiments, the compounds and compositions can be used to inhibit graft-vs-host disease, allergic responses such as hay fever or an allergy to penicillin or other drugs, an autoimmune response in a subject suffering from an autoimmune response which is derived from an infectious disease, or inhibiting fibrosis in a subject. Examples of fibrosis include, but are not limited to, pulmonary fibrosis or fibrotic disease. Examples of pulmonary fibrosis include, but are not limited to, pulmonary fibrosis secondary to adult respiratory distress syndrome, drug-induced pulmonary fibrosis, idiopathic pulmonary fibrosis, and hypersensitivity pneumonitis. Examples of fibrotic diseases include, but are not limited to, Hepatitis-C, Hepatitis-B, cirrhosis, cirrhosis of the liver secondary to a toxic insult, cirrhosis of the liver secondary to drugs, cirrhosis of the liver secondary to a viral infection, and cirrhosis of the liver secondary to an autoimmune disease.

In some embodiments, the compounds and compositions can inhibit an autoimmune response in a subject suffering from an autoimmune response which is derived from, for example, Reiter' syndrome, spondyloarthritis, Lyme disease, HIV infection, syphilis, or tuberculosis.

In some embodiments, the compounds and compositions can inhibit gastrointestinal disease such as, for example, esophageal dysmotility, inflammatory bowel disease, and scleroderma. Alternately, the compounds and compositions can inhibit vascular disease such as, for example, atherosclerosis and reperfusion injury.

In some embodiments, the compounds and compositions can inhibit the proliferation of T cell tumor cells in a subject suffering from a T cell cancer such as, for example, a T cell leukemia or lymphoma. Alternately, the compounds and compositions can inhibit viral infection of T cells of a subject by the HTLV I virus.

In some embodiments, the compounds and compositions can be used for imaging tumor cells or neoplastic cells in a subject that express a protein that is specifically recognized by hu5c8. One method for imaging tumor cells or neoplastic cells in a subject comprises: administering to the subject an effective amount of the antibody, or fragment thereof, or composition comprising the same, under conditions permitting the formation of a complex between the antibody or antibody fragment and a protein on the surface of tumor cells or neoplastic cells, and imaging any antibody/protein complex or antibody fragment/complex formed, thereby imaging any tumor cells or neoplastic cells in the subject.

In some embodiments, the compounds and compositions can be used to detect the presence of tumor cells or neoplastic cells in a subject that express a protein that is specifically recognized by hu5c8. One method for detecting the presence of tumor cells or neoplastic cells in a subject comprises: administering to the subject an effective amount of the antibody, or antibody fragment, or a composition comprising the same, under conditions permitting the formation of a complex between the antibody or antibody fragment and a protein, clearing any unbound imaging agent from the subject, and detecting the presence of any antibody/protein complex or antibody fragment/complex formed, the presence of such complex indicating the presence of tumor cells or neoplastic cells in the subject.

The antibodies, or fragments thereof, and compositions comprising the same, can be administered as a single dosage for certain indications, such as preventing immune response to an antigen to which a subject is exposed for a brief time, such as an exogenous antigen administered on a single day of treatment. Examples of such a therapy would include coadministration of the antibody or antibody derivative of the invention along with a therapeutic agent, for example an antigenic pharmaceutical, an allergen or a blood product, or a gene therapy vector. In indications where antigen is chronically present, such as in controlling immune reaction to transplanted tissue or to chronically administered antigenic pharmaceuticals, the antibodies, antibody derivatives or pharmaceutical compositions of the invention are administered at intervals for as long a time as medically indicated, ranging from days or weeks to the life of the subject.

In some embodiments, the subject(s) that can be treated by the above-described methods is an animal, such as a mammal, including, but are not limited to, humans, non-human primates, rodents (including rats, mice, hamsters and guinea pigs) cow, horse, sheep, goat, pig, dog and cat. In most instances, the mammal is a human.

The present invention also provides use of any of the peptides, or fragments thereof, or antibodies, or fragments thereof, described herein for treating a human disease or disorder associated with CD154.

The present invention also provides use of any of the peptides, or fragments thereof, or antibodies, or fragments thereof, described herein in the manufacture of a medicament for the treatment of a human disease or disorder associated with CD154.

The embodiments disclosed herein may be better understood based on the Examples that follow. However, one skilled in the art will readily appreciate that the specific methods and results discussed are merely illustrative of the invention as described more fully in the embodiments of the invention that follow thereafter.

Throughout this application, various publications and references are referred to within parenthesis. Disclosures of these publications and references, in their entireties, are hereby incorporated by reference into this application to more fully describe the state of the art to which this invention pertains. The materials, methods, and examples are illustrative only and not intended to be limiting.

Standard reference works setting forth the general principles of recombinant DNA technology known to those of skill in the art include Ausubel et al., Current Protocols In Molecular Biology, John Wiley & Sons, New York (1998 and Supplements to 2001); Sambrook et al., Molecular Cloning: A Laboratory Manual, 2d Ed., Cold Spring Harbor Laboratory Press, Plainview, N.Y. (1989); Kaufman et al., Eds., Handbook Of Molecular And Cellular Methods In Biology And Medicine, CRC Press, Boca Raton (1995); McPherson, Ed., Directed Mutagenesis: A Practical Approach, IRL Press, Oxford (1991).

Standard reference works setting forth the general principles of immunology known to those of skill in the art include: Harlow and Lane, Antibodies: A Laboratory Manual, 2d Ed., Cold Spring Harbor Laboratory Press, Cold Spring Harbor, N.Y. (1999); and Roitt et al., Immunology, 3d Ed., Mosby-Year Book Europe Limited, London (1993). Standard reference works setting forth the general principles of medical physiology and pharmacology known to those of skill in the art include: Fauci et al., Eds., Harrison's Principles Of Internal Medicine, 14th Ed., McGraw-Hill Companies, Inc. (1998).

EXEMPLIFICATION

Throughout the examples, the following materials and methods were used unless otherwise stated. The following examples illustrate the methods and products of the present invention. Suitable modifications and adaptations of the described conditions and parameters normally encountered in the art of molecular biology that are apparent to those skilled in the art are within the spirit and scope of the present invention.

In general, the practice of the present invention employs, unless otherwise indicated, conventional techniques of chemistry, molecular biology, recombinant DNA technology, immunology (especially, for example, antibody technology), and standard techniques in electrophoresis. See, for example, Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds. Ausubel et al., John Wiley & Sons (1992).

Example 1

Antibody Design

The methods described herein were used to obtain an optimized antibody (or an antigen-binding fragment thereof), although other methods known to those skilled in the art can also be used without limitation. Based on a computational analysis, positions can be identified within any given antibody where there is a difference (the larger the difference, the more significant it can be) between the charge distribution in an optimized antibody-antigen complex and that in an original antibody-antigen complex. Such differences in charge distribution are also associated with changes in binding free energy of the antibody when bound to the antigen in a solvent. The amino acid residue at such a position can then be changed so that the electrostatic forces in the original antibody more nearly approach (or in alternative embodiments, are more divergent from) those in the optimized antibody, thereby modulating binding free energy of the antibody when bound to an antigen in a solvent. Changes to the antibody are introduced according to a set of discrete criteria or rules as described herein and as described in International Publication Serial No. PCT/US04/24200, which is incorporated herein by reference in its entirety.

1. Rules for Modifying Antibodies for Improved Function

The rules for modifying antibodies were applied as follows. To modulate the antigen-binding affinity of an antibody, for example, to improve or restore such binding, basic sequence and/or structural data is first acquired. Electrostatic charge optimization techniques were then applied to suggest improved-affinity mutants. Typically, an electrostatic charge optimization was first used to determine the position(s) of the CDR residue(s) that are sub-optimal for binding (Lee et al., J. Chem. Phys., 1997, 106, 8681-8690; Kangas et al., J. Chem. Phys., 1998, 109, 7522-7545). Then, one or more CDR mutations (i.e., modifications) are subjected to further computational analysis. Based on these calculations, the binding affinity was then determined for a subset of modified antibodies having one or more modifications according to the rules of the invention.

Using a continuum electrostatics model, an electrostatic charge optimization was performed on each side chain of the amino acids in the CDRs of the antibody. A charge optimization gives charges at atom centers but does not always yield actual mutation(s). Accordingly, a round of charge optimizations was performed with various constraints imposed to represent natural side chain characteristics at the positions of interest. For example, an optimization was performed for a net side chain charge of −1, 0, and +1 with the additional constraint that no atom's charge exceeded a particular value, for example, 0.85 electron charge units. Candidate amino acid side chain positions, and residue modifications at these positions, were then determined based on the potential gain in electrostatic binding free energy observed in the optimizations.

Binding free energy difference (in kcal/mol) in going from the native residue to a completely uncharged sidechain isostere, such as, a residue with the same shape but no charges or partial charges on the atoms were calculated. Negative numbers indicate a predicted increase of binding affinity. Optimal charge distribution wherein the net side chain charge is +1, 0, or −1 was used to calculate the binding free energy difference.

In those instances in which binding free energy difference is favorable ($\Delta G<-0.25$ kcal/mol) and associated with a transition from the native residue to a completely uncharged side chain isostere, such as, a residue with the same shape but no charges or partial charges on the atoms, modifications from the set of amino acids with nonpolar sidechains, for example, Ala, Cys, Ile, Leu, Met, Phe, Pro, Val were selected.

Where the binding free energy difference that can be obtained with an optimal charge distribution in the side chain and a net side chain charge of −1 is favorable ($\Delta G<-0.25$ kcal/mol), modifications from the set of amino acids with negatively charged side chains, for example, Asp, Glu were selected.

Similarly, where the binding free energy difference that can be obtained with an optimal charge distribution in the side chain and a net side chain charge of +1 is favorable ($\Delta G<-0.25$ kcal/mol), modifications from the set of amino acids with positively charged sidechains, for example, Arg, His, Lys were selected.

Finally, in those cases where the binding free energy difference that can be obtained with an optimal charge distribution in the side chain and a net side chain charge of 0 is favorable ($\Delta G<-0.25$ kcal/mol), modifications from the set of amino acids with uncharged polar sidechains, for example, Asn, Cys, Gln, Gly, His, Met, Phe, Ser, Thr, Trp, Tyr, to which are added Cys, Gly, Met and Phe were selected.

As described herein, the designed modified antibodies were built in silico and the binding energy recalculated. Modified side chains were built by performing a rotamer dihedral scan in CHARMM, using dihedral angle increments of 60 degrees, to determine the most desirable position for each side chain. Binding energies were then calculated for the wild type (parent) and mutant (modified) complexes using the Poisson-Boltzmann electrostatic energy and additional terms for the van der Waals energy and buried surface area.

Results from these computational modification calculations were then reevaluated as needed, for example, after subsequent reiterations of the method either in silico or informed by additional experimental structural/functional data.

The rules allow for several predictions to be made which can be categorized as follows:

1) modifications at the interaction interface involving residues on the antibody that become partially buried upon binding (interactions are improved by making hydrogen bonds with the antigen);

2) modifications of polar residues on the antibody that become buried upon binding and thus pay a desolvation penalty but do not make any direct electrostatic interactions with the antigen (improvements are usually made by modifying to a hydrophobic residue with similar shape to the wild-type residue or by adding a residue that can make favorable electrostatic interactions); and 3) modifications of surface residues on the antibody that are in regions of uncomplimentary potentials. These modifications are believed to improve long-range electrostatic interactions between the antibody and antigen without perturbing packing interactions at the binding interface.

The first type of modification is determined by inspection of basic physical/chemical considerations, as these residues essentially make hydrogen bonds with unsatisfied hydrogen partners of the antigen. Unlike other methods, the rules of the invention allowed for surprising residue modifications in which the cost of desolvation is allowed to outweigh the beneficial interaction energy.

The second type of modification represents still another set of modifications, as the energy gained is primarily a result of eliminating an unfavorable desolvation while maintaining non-polar interactions.

The third type of modification concerns long-range interactions that show potential for significant gain in affinity. These types of modifications are particularly interesting because they do not make direct contacts with the antigen and, therefore, pose less of a perturbation in the delicate interactions at the antibody-antigen interface.

Accordingly, when the desired side chain chemistries were determined for the candidate amino acid position(s) according to the rules, the residue position(s) was then modified or altered, for example, by substitution, insertion, or deletion, as further described herein.

In addition to the above rules for antibody modification, it is noted that certain determinations, for example, solvent effects can be factored into initial (and subsequent) calculations of optimal charge distributions.

2. Obtaining an Antibody or Antigen-Binding Fragment Thereof

The methods of the invention that are aimed at generating a non-naturally occurring antibody (or an antigen-binding fragment thereof) can, but do not necessarily, begin by obtaining an antibody. That antibody may be referred to herein as a "parent" antibody or sometimes as a "first" antibody, and it can be used to obtain information that will allow one to modify or alter one or more amino acid residues either within that antibody (such as, within the parent antibody) or within a modified or altered antibody having a sequence that is similar to, or that contains portions of, the sequence of the parent antibody. As described herein, for example, one or more of the CDRs (or portions thereof) of a parent antibody, were replaced with the corresponding CDR(s) of the modified antibody by standard genetic engineering techniques to accomplish the so-called CDR graft or transplant. Accordingly, the method began with a mammalian monoclonal or polyclonal antibody (for example, murine or primate), chimeric, CDR-grafted, humanized, or human antibody.

The parent antibodies were obtained from art-recognized sources or produced according to art-recognized technologies. For example, the parent antibody was a CDR-grafted or humanized antibody having CDR regions derived from another source or species, for example, murine.

The parent antibody or any of the modified antibodies of the invention can also be in the format of a monoclonal antibody. Methods for producing monoclonal antibodies are known in the art (see, for example, Kohler and Milstein, Nature, 1975, 256, 495-497), as well as techniques for stably introducing immunoglobulin-encoding DNA into myeloma cells (see, for example, Oi et al., Proc. Natl. Acad. Sci. USA, 1983, 80, 825-829; Neuberger, EMBO J., 1983, 2, 1373-1378; and Ochi et al., Proc. Natl. Acad. Sci. USA, 1983, 80, 6351-6355). These techniques, which include in vitro mutagenesis and DNA transfection, allow for the construction of recombinant immunoglobulins; these techniques can be used to produce the parent and modified antibodies used in the methods of the invention or to produce the modified antibodies that result from those methods. Alternatively, the parent antibodies can be obtained from a commercial supplier. Antibody fragments (scFvs and Fabs) can also be produced in E. coli (production methods and cellular hosts are described further below).

The parent antibody or any of the modified antibodies of the invention can be an antibody of the IgA, IgD, IgE, IgG, or IgM class.

As noted above, the methods of the invention can be applied to more than just tetrameric antibodies (for example, antibodies having the structure of an immunoglobulin of the G class (an IgG)). For example, the methods of modifying an antibody can be carried out with antigen-binding fragments of any antibody as well. The fragments can be recombinantly produced and engineered, synthesized, or produced by digesting an antibody with a proteolytic enzyme. For example, the fragment can be an Fab fragment; digestion with papain breaks the antibody at the region, before the inter-chain (such as, $V_H$-$V_H$) disulphide bond, that joins the two heavy chains. This results in the formation of two identical fragments that contain the light chain and the $V_H$ and $C_H1$ domains of the heavy chain. Alternately, the fragment can be an F(ab')$_2$ fragment. These fragments can be created by digesting an antibody with pepsin, which cleaves the heavy chain after the inter-chain disulphide bond, and results in a fragment that contains both antigen-binding sites. Yet another alternative is to use a "single chain" antibody. Single-chain Fv (scFv) fragments can be constructed in a variety of ways. For example, the C-terminus of $V_H$ can be linked to the N-terminus of $V_L$. Typically, a linker (for example, (GGGGS)$_4$ (SEQ ID NO: 58)) is placed between $V_H$ and $V_L$. However, the order in which the chains can be linked can be reversed, and tags that facilitate detection or purification (for example, Myc-, His-, or FLAG-tags) can be included (tags such as these can be appended to any antibody or antibody fragment of the invention; their use is not restricted to scFv). Accordingly, and as noted below, tagged antibodies are within the scope of the present invention. In alternative embodiments, the antibodies used in the methods described herein, or generated by those methods, can be heavy chain dimers or light chain dimers. Still further, an antibody light or heavy chain, or portions thereof, for example, a single domain antibody (DAb), can be used.

As the methods of the invention can be iterative, the parent antibody may not be a naturally occurring antibody. As the process of modifying an antibody can be repeated as many times as necessary, the starting antibody (or antigen-binding fragment thereof) can be wholly non-human or an antibody containing human FRs and non-human (for example, murine) CDRs. That is, the "parent" antibody can be a CDR-grafted antibody that is subjected to the methods of the invention in order to improve the affinity of the antibody, such as, affinity mature the antibody. As noted above, the affinity may only be improved to the extent that it is about the same as (or not significantly worse than) the affinity of the naturally occurring human antibody (the FR-donor) for its antigen. Thus, the "parent" antibody may, instead, be an antibody created by one or more earlier rounds of modification, including an antibody that contains sequences of more than one species (for example, human FRs and non-human CDRs). The methods of the invention encompass the use of a "parent" antibody that includes one or more CDRs from a non-human (for example, murine) antibody and the FRs of a human antibody. Alternatively, the parent antibody can be completely human.

Where the structure is available, of course, one may begin the computational analysis with that structure (rather than creating it again).

3. The Method of the Invention Informed by Antibody-Antigen Structural Data

Proteins are known to fold into three-dimensional structures that are dictated by the sequences of their amino acids and by the solvent in which a given protein (or protein-containing complex) is provided. The three-dimensional structure of a protein influences its biological activity and stability, and that structure can be determined or predicted in a number of ways. Generally, empirical methods use physical biochemical analysis. Alternately, tertiary structure can be predicted using model building of three-dimensional structures of one or more homologous proteins (or protein complexes) that have a known three-dimensional structure. X-ray crystallography is perhaps the best-known way of determining protein structure (accordingly, the term "crystal structure" may be used in place of the term "structure"), but estimates can also be made using circular dichroism, light scattering, or by measuring the absorption and emission of radiant energy. Other useful techniques include neutron diffraction and nuclear magnetic resonance (NMR). All of these methods are known to those of ordinary skill in the art, and they have been well described in standard textbooks (see, for example, *Physical Chemistry*, 4th Ed., W. J. Moore, Prentiss-Hall, N.J., 1972, or *Physical Biochemistry*, K. E. Van Holde, Prentiss-Hall, N.J., 1971)) and numerous publications. Any of these techniques can be carried out to determine the structure of an antibody, or antibody-antigen-containing complex, which can then be analyzed according to the methods of the present invention and, for example, used to inform one or more steps of the method of the invention.

Similarly, these and like methods can be used to obtain the structure of an antigen bound to an antibody fragment, including a fragment consisting of, for example, a single-chain antibody, Fab fragment, and the like. Methods for forming crystals of an antibody, an antibody fragment, or scFv-antigen complex have been reported by, for example, van den Elsen et al. (Proc. Natl. Acad. Sci. USA, 1999, 96, 13679-13684, which is expressly incorporated by reference herein).

4. Computational Analysis

The basic computational formulae used in carrying out the methods of the invention are provided in, for example, U.S. Pat. No. 6,230,102, the contents of which are hereby incorporated by reference in the present application in their entirety.

As noted above, antibodies are altered (or "modified") according to the results of a computational analysis of electrostatic forces between the antibody and an antigen to which it binds, preferably, in accordance to the discrete criteria or rules of the invention described herein. The computational analysis allows one to predict the optimal charge distribution within the antibody, and one way to represent the charge distribution in a computer system is as a set of multipoles. Alternately, the charge distribution can be represented by a set of point charges located at the positions of the atoms of the antibody. Once a charge distribution is determined (preferably, an optimal charge distribution), one can modify the antibody to match, or better match, that charge distribution.

The computational analysis can be mediated by a computer-implemented process that carries out the calculations described in U.S. Pat. No. 6,230,102. The computer program is adapted herein to consider the real world context of antigen-antibody binding (and unlike other methods, this methods of the invention take into account, for example, solvent, long-range electrostatics, and dielectric effects in the binding between an antibody and its antigen in a solvent). The process is used to identify modifications to the antibody structure that will achieve a charge distribution on the "matured" antibody that minimizes the electrostatic contribution to binding free energy between the matured antibody and its antigen (compared to that of the unmodified ("starting" or "parent") antibody. As is typical, the computer system (or device(s)) that performs the operations described here (and in more detail in U.S. Pat. No. 6,230,102) will include an output device that displays information to a user (for example, a CRT display, an LCD, a printer, a communication device such as a modem, audio output, and the like). In addition, instructions for carrying out the method, in part or in whole, can be conferred to a medium suitable for use in an electronic device for carrying out the instructions. Thus, the methods of the invention are amendable to a high throughput approach comprising software (for example, computer-readable instructions) and hardware (for example, computers, robotics, and chips). The computer-implemented process is not limited to a particular computer platform, particular processor, or particular high-level programming language.

A useful process is set forth in, for example, U.S. Pat. No. 6,230,102, and a more detailed exposition is provided in, for example, Lee and Tidor (J. Chem. Phys., 1997, 106, 8681-8690), each of which is expressly incorporated herein by reference.

5. Structure-Based Computational Design Methods

An exemplary approach to improving the affinity of an antibody to its antigen is by using structure-based computational design methods. One such method is known as sidechain repacking using the dead-end elimination algorithm (see for example, Lasters et al., Protein Eng., 8, 815-22; Looger et al., J. Mol. Biol., 307, 429-45; Dahiyat et al., Protein Sci., 5, 895-903). In such a calculation, antibody residues are simultaneously mutated computationally to any of the 20 naturally occurring amino acids and the resulting mutants are evaluated for affinity computationally. The list of computationally generated mutants can be sorted by calculated stability of the mutant in order to generate a list of variants that will be expressed experimentally. In the calculations the protein backbone is allowed very little or no flexibility, which ensures that the designed mutants are predicted to be stable with the given CDR conformations. Thus, the computational analysis allows one to predict antibody mutations that will enhance the affinity to its antigen.

6. Generation of Antibodies and Antigen-Binding Fragments Thereof

The selection, cloning, and manufacture of antibodies, for example, chimeric, humanized, monoclonal, and single-chain antibodies is well described in the art. In addition, the humanization of hu5c8 mAb has been described previously (see, Lederman S et al., J Exp Med. 1992 Apr. 1; 175(4):1091-101 and Karpusas M et al, Structure (Camb). 2001 Apr. 4; 9(4):321-9, respectively. This antibody is available from the ATCC (PTA-4931). The 5c8 antibody was stably expressed in NS0 myeloma cells and purified by Protein A and gel filtration chromatography. SDS-PAGE and analytical gel filtration chromatography demonstrated that the protein formed the expected disulfide linked tetramer. The single-chain antibodies of the invention were typically expressed in *E. coli* and immunopurified using standard techniques.

7. 5c8 Fab Production

5c8 Fab was expressed by the bicistronic plasmid pBEF064. The first cistron contains 354 nucleotides of the 5c8 heavy chain encoding the 118 amino acid heavy chain variable region followed in frame by 306 nucleotides encoding the first 102 amino acids of the human IgG1 constant domain and 18 nucleotides encoding a 6 histidine tag (SEQ ID NO: 59). A second ribosome entry site is located 7 nucleotides after the end of the heavy chain cistron. The second cistron contains 333 nucleotides encoding the 111 amino acid 5c8 light chain variable region followed in frame by 321 nucleotides encoding the 107 amino acid light chain constant domain. Expression was carried out in *E. coli* and was driven by the ara-BAD promoter and the heavy and light chains are directed to the periplasmic space by the OmpA (heavy chain) and PhoA (light chain) periplasmic localization signals. The periplasmic localization signals were cleaved from the protein during periplasmic export.

8. Binding Assays

Binding assays were typically performed using the KinExA™ kit. The assay was carried out by passing a dilute solution of the antibody (or antigen-binding fragment) through the column provided in the kit, and some of the antibody (or the antigen-binding fragment thereof) interacts with the antigen on the bead. The antibody (or the fragment) was then detected with a secondary anti-human IgG heavy and light chain antibody conjugated with the fluorescent dye Cy5 (Jackson ImmunoResearch Laboratories, Inc., West Grove, Pa.). The concentration of the antibody (or the fragment) was set so that the signal from the fluorescent dye is proportional to the concentration of protein. To obtain the solution phase affinity of the interaction, the antibody (or the fragment) was mixed with a dilution series of soluble antigen. These proteins (antibody and antigen) were allowed to reach equilibrium during a three-hour incubation at room temperature or an overnight incubation at 4° C. The mixture was flowed over the antigen-containing column, and the signal was proportional to the amount of unbound antibody (or antibody fragment) that remains in solution. The resulting data was plotted on a linear-log scale graph and fit to a quadratic curve by non-linear regression, which gives a value for the $K_D$.

9. Binding Assay 5c8-CD154

An ELISA-based competitive binding assay was carried out. Anti c-myc mAb was coated onto NUNC Maxisorb plates at 10 μg/mL in PBS for 2 hrs at RT. Serial dilutions of unlabeled 5c8 Fab (mutants or wildtype) were made and mixed with equal volumes of fixed concentration (30 ng/ml) of biotin-labeled 5c8 Fab competitor, and added to the plate. After 2 hours incubation at room temperature, the plate was washed and bound biotin-labeled 5c8 Fab competitor was detected with streptavidin-HRP. Binding affinities were obtained from four parameter curve fits.

Example 2

Antibodies

1. Generation of Antibodies

The selection, cloning, and humanization of hu5c8 mAb have been described previously. See Lederman S et al., J Exp Med. 1992 Apr. 1; 175(4):1091-101 and Karpusas M et al, Structure (Camb). 2001 Apr. 4; 9(4):321-9, respectively. The hu5c8 mAb hyridoma is available from the ATCC (HB10916).

2. CD154 Binding Assay

A FACS-based competitive binding assay was carried out on huCD154+ D1.1 cells available from the ATCC(CRL-10915). The binding of 0.1 mg/ml of biotinylated hu5c8 mAb to cell surface CD154 was competed with titrations of hu5c8 mAb or other antibody. Cell-bound biotinylated hu5c8 mAb was detected with streptavidin-phycoerytherin (PE) (BD-PharMingen San Diego, Calif., USA). Relative binding affinities were inferred from the IC50 values of four parameter curve fits.

3. CD154-FcγR Bridging Assays

FcγR binding affinities were measured using assays based on the ability of the antibody to form a "bridge" between antigen and a FcγR bearing cell (see below). The FcγRI (CD64) bridging assay was performed by coating 96-well Maxisorb ELISA plates (Nalge-Nunc Rochester, N.Y., USA) overnight at 4° C. with 1 mg/ml recombinant soluble human CD154 (Biogen, Karpusas M et al. Structure. 1995 Dec. 15; 3(12):1426) in PBS and then blocking with 1% BSA in PBS. Titrations of antibody were then be bound to CD154 for 30 minutes at 37° C., the plates were washed, and the binding of fluorescently labeled U937 (CD64+) cells was measured. The U937 cells were grown in RPMI medium with 10% FBS, 10 mM HEPES, L-glutamine, and penicillin/streptomycin, split 1:2, and activated for one day prior to the assay with 1000 units/ml of IFNγ to increase FcγRI expression.

The FcγRIII (CD16) bridging assays were performed using a monolayer of CD154-expressing Chinese Hamster Ovary (CHO) cells (Biogen) grown in 96-well tissue culture plates (Corning Life Sciences Acton, Mass., USA), with measurement of the mAb-dependent binding of fluorescently labeled Jurkat cells transfected with CD16 (gift of Dana Farber Institute, Boston, Mass., USA). The CHO-CD154+ cells were seeded into 96-well plates at 1×10⁵ cells/ml and grown to confluency in α MEM with 10% dialyzed FBS, 100 nM methotrexate, L-glutamine, and penicillin/streptomycin (all reagents from Gibco-BRL Rockville, Md., USA). CD16+ Jurkat cells, growing in RPMI with 10% FBS, 400 mg/ml Geneticin, 10 mM HEPES, sodium pyruvate, L-glutamine, and penicillin/streptomycin (all reagents from Gibco-BRL), were split 1:2 one day prior to performing the assay.

In the assays for both the FcγRI and FcγRIII receptors, the Fc receptor-bearing cells were labeled with 2',7'-bis-(2-carboxyethyl)-5-(and-6)-carboxyfluorescein acetoxymethyl ester (BCECF-AM) (Molecular Probes Eugene, Oreg., USA) for 20 minutes at 37° C. After washing to remove excess BCECF-AM, 1×10⁵ of the labeled cells were incubated in the assay for 30 minutes at 37° C. Unbound FcγR+ cells were removed by washing several times and plates read on a Cytofluor 2350 Fluorescent Microplate Reader (Millipore Corporation Bedford, Mass., USA) with an excitation wavelength of 485 nm and an emission wavelength of 530 nm.

Example 3

Improving the Antigen-Binding Affinity of an Anti-CD154 Antibody

In this example, methods for improving the binding affinity of an antibody against a therapeutically relevant antigen target, are described.

An antibody against human CD154 (see, for example, Yamada et al., Transplantation, 2002, 73, S36-9; Schonbeck et al., Cell. Mol. Life. Sci., 2001, 58, 4-43; Kirk et al., Philos. Trans. R. Soc. Lond. B. Sci., 2001, 356, 691-702; Fiumara et al., Br. J. Haematol., 2001, 113, 265-74; and Biancone et al., Int. J. Mol. Med., 1999, 3, 343-53) which is a member of TNF family of proteins involved in mediating immunological responses, was raised by affinity maturation in mice. The 5c8 monoclonal antibody was developed from such studies and determined to inhibit the pathological processes mediated by CD154.

In an effort to increase the affinity 5c8/CD154 interaction, electrostatic charge optimization techniques were applied to a crystal structure of the antibody-antigen complex in a two-level procedure to suggest improved-affinity mutants. First, electrostatic charge optimization was used to determine the position(s) of the CDR residue(s) that are sub-optimal for binding (Lee and Tidor, J. Chem. Phys., 1997, 106, 8681-8690; Kangas and Tidor, J. Chem. Phys., 1998, 109, 7522-7545). Second, a set of CDR mutations were determined for further computational analysis. Based on these calculations, the binding affinity was computationally determined for 23 modified antibodies having a single mutation (i.e., 23 "single mutants"). It was predicted that 8 of the single mutants would be more favorable than wild-type antibody both in terms of electrostatic energy, and in terms of full energy function including a van der Waals energy term and a solvent accessible surface area term. These terms are unrelated to electrostatic forces, but they were calculated to ensure that the designed mutations did not contact other residues and would not reduce the amount of buried surface area significantly; increased buried surface area in complex formation is usually beneficial (see the "Full Energy" column of the table below).

Based on results from a charge optimization, mutations were determined for computational analysis (the optimal charge distributions and design mutations that were closer to optimal than the current residue were examined; this process was done by inspection). A charge optimization gave charges at atom centers but did not yield actual mutation. A round of charge optimizations was performed with various constraints imposed to represent natural side chain characteristics. For example, an optimization was performed for a net side chain charge of −1, 0, and +1 with the additional constraint that no atom's charge exceeded an absolute value of 0.85 electron charge units.

The crystal structure of the CD154/5c8 complex (PDB code: 1I9R) was prepared using standard procedures for adding hydrogens with the program CHARMM (Accelrys, Inc., San Diego, Calif.). N-acetamide and N-methylamide patches were applied to the N termini and C-termini, respectively. Using a continuum electrostatics model, an electrostatic charge optimization was performed on each side chain of the amino acids in the CDRs of the ACQ2 antibody. Appropriate side chain mutations were then determined based on the potential gain in electrostatic binding energy observed in the optimizations. Side chains were built by performing a rotamer dihedral scan in CHARMM, using dihedral angle increments of 60 degrees, to determine the most desirable position for each side chain. Binding energies were then calculated for the wild type and mutant complexes using the Poisson-Boltzmann electrostatic energy and additional terms for the van der Waals energy and buried surface area.

The crystal structure of the CD40 ligand complexed with the Fab fragment of a humanized neutralizing antibody (5c8) was solved to 3.1 Å at a pH of 6.50. Since CD154 is naturally a trimer, there are three 5c8 Fab molecules and 5 CD154 molecules in the complex. They form three independent CD154/5c8 interfaces in the complex. A zinc (ZN) atom was bound to each of the 5c8 Fab and it was included into the calculation. Calculations were carried out independently for three interfaces and the amino acid substitutions that were found to be favorable over wild type for all three sites were exploited.

The following table shows the optimization results obtained for CDR variable loop 1 in the light chain of 5c8 for all three 5c8 molecules. The Mut (Mutation energy) column corresponds to the binding free energy difference (in kcal/mol) in going from the native residue to a completely uncharged sidechain isostere, i.e., a residue with the same shape but no charges or partial charges on the atoms. Negative numbers indicate a predicted increase of binding affinity. The Opt−1 column corresponds to the binding free energy difference that can be obtained with an optimal charge distribution in the side chain and a net side chain charge of −1. The columns Opt0 and Opt1 correspond to the binding free energy differences with optimal charges, the net charge being 0 and +1, respectively. Based on these results and the visual inspection of the structure, mutations are designed that could take advantage of these binding free energy improvements. For instance, the mutation from SER 31 to VAL, which is an uncharged isostere, makes use of the predicted −1.23 to −0.98 kcal/mol in the mutation energy. The mutation GLN 27 to GLU uses the −1.21 to −0.88 kcal/mol predicted maximal free energy gain for a mutation to a side chain with a net charge of −1.

TABLE 1

Optimization results obtained for 5c8 CDR light chain variable loop 1

| Chain Residue | Mut | Opt-1 | Opt0 | Opt1 |
|---|---|---|---|---|
| 1L 24 ARG | −0.11 | 0.17 | −0.11 | −0.37 |
| 1L 26 SER | −0.06 | −0.59 | −0.06 | 0.57 |
| 1L 27 GLN | 0.21 | −1.21 | −0.95 | −0.26 |
| 1L 28 ARG | 0.11 | −0.96 | −0.71 | −0.40 |
| 1L 30 SER | −0.01 | −0.14 | −0.42 | −0.47 |
| 1L 31 SER | −1.23 | 3.88 | −2.16 | −0.42 |
| 1L 32 SER | 1.45 | 0.91 | −0.65 | −0.67 |
| 1L 33 THR | −0.02 | −0.66 | −0.41 | 0.07 |
| 1L 34 TYR | −0.25 | −1.00 | −1.10 | −0.80 |
| 1L 35 SER | −0.02 | 0.00 | −0.11 | 0.04 |
| 1L 36 TYR | 0.01 | −0.95 | −1.31 | 1.74 |
| 1L 38 HSD | −0.15 | −0.48 | −0.70 | −0.62 |
| 2L 24 ARG | −0.46 | −1.04 | −0.46 | 0.13 |
| 2L 26 SER | −0.29 | −1.60 | −0.79 | 0.19 |
| 2L 27 GLN | 0.26 | −0.88 | −0.41 | 0.35 |
| 2L 28 ARG | −0.59 | −0.94 | −0.46 | 0.08 |
| 2L 30 SER | 0.08 | −0.38 | −0.55 | −0.42 |
| 2L 31 SER | −0.98 | 4.04 | −1.89 | −0.54 |
| 2L 32 SER | 0.74 | 2.31 | −0.86 | −0.87 |
| 2L 33 THR | 0.00 | −0.65 | −0.38 | 0.09 |
| 2L 34 TYR | −0.09 | −0.62 | −0.48 | −0.12 |
| 2L 35 SER | 0.09 | 0.02 | 0.09 | 0.18 |
| 2L 36 TYR | 0.10 | −1.70 | −1.24 | 2.37 |
| 2L 38 HSD | −0.23 | −1.20 | −1.17 | −0.79 |
| 3L 24 ARG | −0.35 | −0.34 | −0.35 | −0.35 |
| 3L 26 SER | −0.27 | −1.23 | −0.53 | 0.27 |
| 3L 27 GLN | 0.11 | −1.07 | −0.71 | −0.08 |
| 3L 28 ARG | −0.30 | −0.85 | −0.30 | 0.15 |
| 3L 30 SER | 0.03 | 0.02 | −0.29 | −0.36 |
| 3L 31 SER | −1.06 | 4.02 | −2.03 | −0.90 |
| 3L 32 SER | 0.82 | 1.18 | −0.85 | −1.05 |
| 3L 33 THR | 0.20 | −0.32 | −0.15 | 0.29 |
| 3L 34 TYR | 0.09 | −0.80 | −0.74 | −0.38 |
| 3L 35 SER | 0.06 | −0.05 | −0.10 | −0.02 |
| 3L 36 TYR | 0.04 | −0.99 | −1.30 | 1.66 |
| 3L 38 HSD | −0.20 | −0.46 | −0.76 | −0.72 |

As described above, the designed mutants were built in silico and the binding energy was recalculated. Results from these computational mutation calculations are shown below. Numbers represent change in binding affinity from wild-type to the mutant (negative meaning mutant is more favorable). Energies for all three chains of 5c8 are given.

TABLE 2

Computational mutation calculations for 5c8 CDRs

| Chain Mutant | Full Energy | Electrostatics |
|---|---|---|
| 1H TYR33PHE | 0.197 | −2.741 |
| 1H ASN59ASP | −0.995 | −2.548 |
| 1H ASN59LEU | −1.294 | −2.517 |
| 1L SER26ASP | −0.703 | −0.712 |
| 1L GLN27GLU | −0.514 | −0.357 |
| 1L SER31VAL | 8.154 | −1.739 |
| 1L THR33ASP | −0.219 | −0.916 |
| 1L TYR54GLU | −0.999 | −0.729 |
| 2H TYR33PHE | 0.623 | −2.726 |
| 2H ASN59ASP | −0.218 | −2.885 |
| 2H ASN59LEU | −1.116 | −3.067 |
| 2L SER26ASP | −1.333 | −1.627 |
| 2L GLN27GLU | −0.658 | −0.395 |
| 2L SER31VAL | 9.293 | −0.832 |
| 2L THR33ASP | −0.430 | −1.359 |
| 2L TYR54GLU | −1.012 | −1.030 |
| 3H TYR33PHE | 0.145 | −1.979 |
| 3H ASN59ASP | −0.837 | −2.267 |
| 3H ASN59LEU | −1.179 | −2.271 |
| 3L SER26ASP | −0.540 | −0.565 |
| 3L GLN27GLU | −0.497 | −0.342 |
| 3L SER31VAL | 8.129 | −1.284 |
| 3L THR33ASP | −0.337 | −0.676 |
| 3L TYR54GLU | −1.123 | −0.825 |

As the results show, the computational process described above was successfully implemented to predict affinity enhancing side chain mutations.

The first type of mutation was resolved by inspection, as these residues essentially make hydrogen bonds with unsatisfied hydrogen partners of the antigen. Surprisingly, the cost of desolvation seemed to outweigh the beneficial interaction energy in most cases. The second type of mutation represents a less intuitive type or set of mutations, as the energy gained is primarily a result of eliminating an unfavorable desolvation while maintaining non-polar interactions. The third mutation type concerns long-range interactions that show potential for significant gain in affinity. These types of mutations are particularly interesting because they do not make direct contacts with the antigen and, therefore, pose less of a perturbation in the delicate interactions at the antibody-antigen interface.

In accordance with the computational data obtained as described above, mutants of 5c8 (Fab fragments) were generated, and their affinity towards CD154 was compared to the affinity of the wild type 5c8 Fab in ELISA-based competitive binding assay and KinExA™ assay described above. Selected results of some of the mutants are shown in the table that follows. Where an affinity assay has been conducted, the results are shown as affinity fold changes over original 5c8 Fab (wild type). Numbers greater than 1.0 indicate increased affinity, numbers smaller than 1.0 indicate decreased affinity.

TABLE 3

Observed affinity changes for 5c8 altered Fab antibody fragments

| HCVD[1] Sequence SEQ ID NO: | Heavy Chain Mutation | LCVD[2] Sequence SEQ ID NO: | Light Chain Mutation | ELISA fold-improvement over wildtype | KinExa $K_d$ (pM) | Mutant # |
|---|---|---|---|---|---|---|
| 4 | (wildtype) | 1 | (wildtype) | 1.0 | 264 | |
| 48 | T30H | 1 | — | 2.3 | 307 | 1 |
| 49 | Y33W | 1 | — | 7.0 | 169 | 2 |
| 4 | — | | Y36W | | 420 | 3 |
| 50 | S54N | 1 | — | 2.0 | 298 | 4 |
| 4 | — | 27 | T33W | 5.0 | 158 | 5 |
| 4 | — | 13 | S26D | 2.6 | 142 | 6 |
| 4 | — | 14 | Q27E | 6.3 | 81 | 7 |
| 4 | — | | S31V | 0.02 | | 8 |
| 4 | — | | T33D | 0.22 | | 9 |
| 4 | — | | Y54E | 0.06 | | 10 |
| | Y33F | 1 | — | 0.05 | | 11 |
| | N59D | 1 | — | 0.13 | | 12 |
| | N59L | 1 | — | 0.01 | | 13 |
| 4 | — | 20 | S26D/Q27E | 5.6 | 41 | 14 |
| 4 | — | 32 | S26D/Q27E/T33W | 3.8 | 44 | 15 |
| 48 | T30H | 20 | S26D/Q27E | 5.8 | 70 | 16 |
| 49 | Y33W | 32 | S26D/Q27E/T33W | 5.9 | 23 | 17 |
| 48 | T30H | 32 | S26D/Q27E/T33W | 5.4 | 54 | 18 |
| 50 | S54N | 20 | S26D/Q27E | | 65 | 19 |
| 50 | S54N | 32 | S26D/Q27E/T33W | | 44 | 20 |
| 55 | T30H/Y33W/S54N | 20 | S26D/Q27E | | 101 | 21 |
| 55 | T30H/Y33W/S54N | 32 | S26D/Q27E/T33W | | 55 | 22 |
| 49 | Y33W | 20 | S26D/Q27E | 5.2 | 53 | 23 |
| 54 | T30H/Y33W | 20 | S26D/Q27E | 8.0 | 52 | 24 |
| 54 | T30H/Y33W | 32 | S26D/Q27E/T33W | 5.6 | 12 | 25 |
| 56 | T30H/S54N | 32 | S26D/Q27E/T33W | | 63 | 26 |
| 57 | Y33W/S54N | 32 | S26D/Q27E/T33W | | 52 | 27 |
| 57 | Y33W/S54N | 20 | S26D/Q27E | | 77 | 28 |

[1]HCVD stands for Heavy Chain Variable Domain

[2]LCVD stands for Light Chain Variable Domain

Analysis of the deviations from the ideal charge distributions on the 50 amino acids in the CDRs of the 5c8 antibody resulted in prediction of five mutants that would have higher affinity towards CD154 compared to wild-type: Asn59Asp, Asn59Leu, Ser26Asp, Gln27Glu, and Tyr54Glu. These mutants were constructed and characterized by competitive ELISA. The improved affinity mutants S26D and Q27E were also combined into a double mutant that had a 9-fold higher affinity compared to the wildtype 5c8 Fab.

The side chain repacking algorithm was applied to the CDRs of 5c8. For 30 CDR residues, $10^{40}$ sequences were computationally analyzed and 14 single and double mutants were selected for experimental follow-up. Several mutants showed higher affinity compared to wildtype 5c8 Fab. The side chain repacking mutants were further combined with higher affinity electrostatic mutants. The combination 5 point mutation had 25-fold higher affinity compared to the wild type. Furthermore, in cells it showed superior inhibition of ICAM upregulation (biological consequence of CD40-CD154 interaction) which was comparable by blocking exhibited by a full length 5c8 antibody. An overall hit rate of 40% in mutant prediction was achieved for both methods.

A T cell-dependent B cell activation assay was performed Inhibition of T cell-dependent B cell activation was measured in D1.1: Ramos co-cultures. Engagement of CD40 on B cells by CD154 results in B cell activation and upregulation of ICAM-1 (CD54). Anti-CD154 mAbs and Fabs inhibit the B cell activation by disrupting the CD40-CD154 interaction. Briefly, titrations of anti-CD154 Fab were added to a 1:4 ratio of D1.1:Ramos cells and incubated overnight. Two-color FACS staining (CD20FITC/CD54APC), which allows for quantitation of ICAM-1 upregulation on the Ramos cells, was performed. Results are shown in Table 4.

TABLE 4

Observed potencies in T cell-dependent B cell activation assay

| Heavy Chain Mutation | Light Chain Mutation | IC50 (ug/ml) |
|---|---|---|
| (wildtype) | (wildtype) | 1.215 |
| — | S26D/Q27E | 0.287 |
| Y33W | S26D/Q27E/T33W | 0.131 |
| T30H/Y33W | S26D/Q27E/T33W | 0.165 |

EQUIVALENTS

For one skilled in the art, using no more than routine experimentation, there are many equivalents to the specific embodiments of the invention described herein. Such equivalents are intended to be encompassed by the following claims.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

The invention claimed is:

1. An antibody or antigen binding fragment thereof that binds CD154 and that comprises a light chain variable region, which comprises light chain CDRs VL CDR1, VL CDR2, and VL CDR3, and a heavy chain variable region, which comprises heavy chain CDRs VH CDR1, VH CDR2, and VH CDR3, wherein
   (i) VL CDR1, VL CDR2, and VL CDR3 respectively have the sequences of
      (a) amino acids 24-38, 54-60, and 93-101 of SEQ ID NO:1 or
      (b) amino acids 24-38, 54-60, and 93-101 of SEQ ID NO:1 except that one or a combination of substitutions is present, wherein the substitutions are selected from the group consisting of
      Ser at position 26 substituted with Asp,
      Gln at position 27 substituted with Glu, and
      Thr at position 33 substituted with Trp;
   and
   (ii) VH CDR1, VH CDR2, and VH CDR3 respectively have the sequences of
      (a) amino acids 26-35, 50-66, and 99-107 of SEQ ID NO:4 or
      (b) amino acids 26-35, 50-66, and 99-107 of SEQ ID NO:4 except that one or a combination of substitutions is present, wherein the substitutions are selected from the group consisting of
      Thr at position 30 substituted with His,
      Tyr at position 33 substituted with Trp, and
      Ser at position 54 substituted with Asn;
   wherein when the light chain CDR sequences have the wild type 5c8 CDR sequences according to (i)(a) above, the heavy chain CDR sequences are not the wild type 5c8 CDR sequences according to (ii)(a) above.

2. The antibody or antigen binding fragment of claim 1, wherein VL CDR1, VL CDR2, and VL CDR3 respectively have the sequences of amino acids 24-38, 54-60, and 93-101 of SEQ ID NO:1.

3. The antibody or antigen binding fragment of claim 1, wherein VH CDR1, VH CDR2, and VH CDR3 respectively have the sequences of amino acids 26-35, 50-66, and 99-107 of SEQ ID NO:4.

4. The antibody or antigen binding fragment of claim 1, wherein VL CDR1, VL CDR2, and VL CDR3 respectively have the sequences of amino acids 24-38, 54-60, and 93-101 of a sequence selected from SEQ ID NO:27, SEQ ID NO:13, SEQ ID NO:14, SEQ ID NO:20, or SEQ ID NO:32.

5. An antibody or antigen binding fragment of claim 1, wherein VH CDR1, VH CDR2, and VH CDR3 respectively have the sequences of amino acids 26-35, 50-66, and 99-107 of a sequence selected from SEQ ID NO:48, SEQ ID NO:49, SEQ ID NO:50, SEQ ID NO:55, SEQ ID NO:54, SEQ ID NO:56, or SEQ ID NO:57.

6. The antibody or antigen binding fragment of claim 1, wherein the antibody or antigen-binding fragment binds to CD154 with greater affinity than does an antibody or antigen binding fragment that is otherwise identical but has wild type 5c8 CDR sequences VL CDR1, VL CDR2, and VL CDR3 that respectively have the sequences of amino acids 24-38, 54-60, and 93-101 of SEQ ID NO:1 and VH CDR1, VH CDR2, and VH CDR3 that respectively have the sequences of amino acids 26-35, 50-66, and 99-107 of SEQ ID NO:4.

7. The antibody or antigen binding fragment of claim 6, wherein the affinity is assessed using ELISA or a KinExA™ assay.

8. The antibody or antigen binding fragment of claim 1, wherein the antibody or antigen-binding fragment shows improved potency in inhibiting T cell-dependent B cell activation compared with an antibody, or antigen binding fragment, that that is otherwise identical but has wild type 5c8 CDR sequences VL CDR1, VL CDR2, and VL CDR3 that respectively have the sequences of amino acids 24-38, 54-60, and 93-101 of SEQ ID NO:1 and VH CDR1, VH CDR2, and VH CDR3 that respectively have the sequences of amino acids 26-35, 50-66, and 99-107 of SEQ ID NO:4.

9. The antigen-binding fragment of claim 1, which is selected from the group consisting of a single chain antibody (scFv), a F(ab')$_2$ fragment, a Fab fragment, and an Fd fragment.

10. The antibody or antigen-binding fragment of claim 1, labeled with a detectable marker.

11. The antibody or antigen-binding fragment of claim 1, conjugated to a therapeutic agent or a bead.

12. The antibody or antigen-binding fragment of claim 1, comprising at least one high molecular-weight polymer.

13. The antibody or antigen-binding fragment of claim 1, wherein at least one amino acid of the antibody or antigen-binding fragment is PEGylated or glycosylated.

14. A composition comprising the antibody or antigen-binding fragment of claim 1.

15. A kit comprising the antibody or antigen-binding fragment of claim 1.

16. A method of treating a human disease or disorder comprising administering a therapeutically effective amount of the antibody or antigen-binding fragment of claim 1 to a human having the disease or disorder, such that the disease or disorder is diminished, wherein the disease or disorder is inflammation, Myasthenia gravis, Graves' disease, idiopathic thrombocytopenia purpura, hemolytic anemia, diabetes mellitus, Crohn's disease, multiple sclerosis, a drug-induced autoimmune disease, rejection of a transplanted organ, graft-vs-host disease, an allergic response, an autoimmune response, fibrosis, gastrointestinal disease, vascular disease, a T cell cancer, or viral infection of T cells by the HTLV I virus.

17. An antibody or antigen binding fragment thereof that binds CD154 and that comprises a light chain variable domain comprising light chain CDRs VL CDR1, VL CDR2, and VL CDR3, and a heavy chain variable domain comprising heavy chain CDRs VH CDR1, VH CDR2, and VH CDR3, wherein
   (i) VL CDR1, VL CDR2, and VL CDR3 respectively have the sequences of amino acids 24-38, 54-60, and 93-101 of SEQ ID NO:1 and VH CDR1, VH CDR2, and VH CDR3 respectively have the sequences of amino acids 26-35, 50-66, and 99-107 of SEQ ID NO:48;

(ii) VL CDR1, VL CDR2, and VL CDR3 respectively have the sequences of amino acids 24-38, 54-60, and 93-101 of SEQ ID NO:1 and VH CDR1, VH CDR2, and VH CDR3 respectively have the sequences of amino acids 26-35, 50-66, and 99-107 of SEQ ID NO:49;
(iii) VL CDR1, VL CDR2, and VL CDR3 respectively have the sequences of amino acids 24-38, 54-60, and 93-101 of SEQ ID NO:1 and VH CDR1, VH CDR2, and VH CDR3 respectively have the sequences of amino acids 26-35, 50-66, and 99-107 of SEQ ID NO:50;
(iv) VL CDR1, VL CDR2, and VL CDR3 respectively have the sequences of amino acids 24-38, 54-60, and 93-101 of SEQ ID NO:27 and VH CDR1, VH CDR2, and VH CDR3 respectively have the sequences of amino acids 26-35, 50-66, and 99-107 of SEQ ID NO:4;
(v) VL CDR1, VL CDR2, and VL CDR3 respectively have the sequences of amino acids 24-38, 54-60, and 93-101 of SEQ ID NO:13 and VH CDR1, VH CDR2, and VH CDR3 respectively have the sequences of amino acids 26-35, 50-66, and 99-107 of SEQ ID NO:4;
(vi) VL CDR1, VL CDR2, and VL CDR3 respectively have the sequences of amino acids 24-38, 54-60, and 93-101 of SEQ ID NO:14 and VH CDR1, VH CDR2, and VH CDR3 respectively have the sequences of amino acids 26-35, 50-66, and 99-107 of SEQ ID NO:4;
(vii) VL CDR1, VL CDR2, and VL CDR3 respectively have the sequences of amino acids 24-38, 54-60, and 93-101 of SEQ ID NO:20 and VH CDR1, VH CDR2, and VH CDR3 respectively have the sequences of amino acids 26-35, 50-66, and 99-107 of SEQ ID NO:4;
(viii) VL CDR1, VL CDR2, and VL CDR3 respectively have the sequences of amino acids 24-38, 54-60, and 93-101 of SEQ ID NO:32 and VH CDR1, VH CDR2, and VH CDR3 respectively have the sequences of amino acids 26-35, 50-66, and 99-107 of SEQ ID NO:4;
(ix) VL CDR1, VL CDR2, and VL CDR3 respectively have the sequences of amino acids 24-38, 54-60, and 93-101 of SEQ ID NO:20 and VH CDR1, VH CDR2, and VH CDR3 respectively have the sequences of amino acids 26-35, 50-66, and 99-107 of SEQ ID NO:48;
(x) VL CDR1, VL CDR2, and VL CDR3 respectively have the sequences of amino acids 24-38, 54-60, and 93-101 of SEQ ID NO:32 and VH CDR1, VH CDR2, and VH CDR3 respectively have the sequences of amino acids 26-35, 50-66, and 99-107 of SEQ ID NO:49;
(xi) VL CDR1, VL CDR2, and VL CDR3 respectively have the sequences of amino acids 24-38, 54-60, and 93-101 of SEQ ID NO:32 and VH CDR1, VH CDR2, and VH CDR3 respectively have the sequences of amino acids 26-35, 50-66, and 99-107 of SEQ ID NO:48;
(xii) VL CDR1, VL CDR2, and VL CDR3 respectively have the sequences of amino acids 24-38, 54-60, and 93-101 of SEQ ID NO:20 and VH CDR1, VH CDR2, and VH CDR3 respectively have the sequences of amino acids 26-35, 50-66, and 99-107 of SEQ ID NO:50;
(xiii) VL CDR1, VL CDR2, and VL CDR3 respectively have the sequences of amino acids 24-38, 54-60, and 93-101 of SEQ ID NO:32 and VH CDR1, VH CDR2, and VH CDR3 respectively have the sequences of amino acids 26-35, 50-66, and 99-107 of SEQ ID NO:50;
(xiv) VL CDR1, VL CDR2, and VL CDR3 respectively have the sequences of amino acids 24-38, 54-60, and 93-101 of SEQ ID NO:20 and VH CDR1, VH CDR2, and VH CDR3 respectively have the sequences of amino acids 26-35, 50-66, and 99-107 of SEQ ID NO:55;
(xv) VL CDR1, VL CDR2, and VL CDR3 respectively have the sequences of amino acids 24-38, 54-60, and 93-101 of SEQ ID NO:32 and VH CDR1, VH CDR2, and VH CDR3 respectively have the sequences of amino acids 26-35, 50-66, and 99-107 of SEQ ID NO:55;
(xvi) VL CDR1, VL CDR2, and VL CDR3 respectively have the sequences of amino acids 24-38, 54-60, and 93-101 of SEQ ID NO:20 and VH CDR1, VH CDR2, and VH CDR3 respectively have the sequences of amino acids 26-35, 50-66, and 99-107 of SEQ ID NO:49;
(xvii) VL CDR1, VL CDR2, and VL CDR3 respectively have the sequences of amino acids 24-38, 54-60, and 93-101 of SEQ ID NO:20 and VH CDR1, VH CDR2, and VH CDR3 respectively have the sequences of amino acids 26-35, 50-66, and 99-107 of SEQ ID NO:54;
(xviii) VL CDR1, VL CDR2, and VL CDR3 respectively have the sequences of amino acids 24-38, 54-60, and 93-101 of SEQ ID NO:32 and VH CDR1, VH CDR2, and VH CDR3 respectively have the sequences of amino acids 26-35, 50-66, and 99-107 of SEQ ID NO:54;
(ixx) VL CDR1, VL CDR2, and VL CDR3 respectively have the sequences of amino acids 24-38, 54-60, and 93-101 of SEQ ID NO:32 and VH CDR1, VH CDR2, and VH CDR3 respectively have the sequences of amino acids 26-35, 50-66, and 99-107 of SEQ ID NO:56;
(xx) VL CDR1, VL CDR2, and VL CDR3 respectively have the sequences of amino acids 24-38, 54-60, and 93-101 of SEQ ID NO:32 and VH CDR1, VH CDR2, and VH CDR3 respectively have the sequences of amino acids 26-35, 50-66, and 99-107 of SEQ ID NO:57;
(xxi) VL CDR1, VL CDR2, and VL CDR3 respectively have the sequences of amino acids 24-38, 54-60, and 93-101 of SEQ ID NO:20 and VH CDR1, VH CDR2, and VH CDR3 respectively have the sequences of amino acids 26-35, 50-66, and 99-107 of SEQ ID NO:57.

18. The antibody or antigen binding fragment of claim 17, wherein the antibody or antigen-binding fragment binds to CD154 with greater affinity than does an antibody or antigen binding fragment that is otherwise identical but has wild type 5c8 CDR sequences VL CDR1, VL CDR2, and VL CDR3 that respectively have the sequences of amino acids 24-38, 54-60, and 93-101 of SEQ ID NO:1 and VH CDR1, VH CDR2, and VH CDR3 that respectively have the sequences of amino acids 26-35, 50-66, and 99-107 of SEQ ID NO:4.

19. The antibody or antigen binding fragment of claim 18, wherein the affinity is assessed using ELISA or a KinExA™ assay.

20. The antibody or antigen binding fragment of claim 17, wherein the antibody or antigen-binding fragment shows improved potency in inhibiting T cell-dependent B cell activation compared with an antibody, or antigen binding fragment, that that is otherwise identical but has wild type 5c8 CDR sequences VL CDR1, VL CDR2, and VL CDR3 that respectively have the sequences of amino acids 24-38, 54-60, and 93-101 of SEQ ID NO:1 and VH CDR1, VH CDR2, and VH CDR3 that respectively have the sequences of amino acids 26-35, 50-66, and 99-107 of SEQ ID NO:4.

21. The antigen-binding fragment of claim 17, which is selected from the group consisting of a single chain antibody (scFv), a F(ab')$_2$ fragment, a Fab fragment, and an Fd fragment.

22. The antibody or antigen-binding fragment of claim 17, labeled with a detectable marker.

23. The antibody or antigen-binding fragment of claim 17, conjugated to a therapeutic agent or a bead.

24. The antibody or antigen-binding fragment of claim 17, comprising at least one high molecular-weight polymer.

25. The antibody or antigen-binding fragment of claim 17, wherein at least one amino acid of the antibody or antigen-binding fragment is PEGylated or glycosylated.

26. A composition comprising the antibody or antigen-binding fragment of claim 17.

27. A kit comprising the antibody or antigen-binding fragment of claim 17.

28. A method of treating a human disease or disorder comprising administering a therapeutically effective amount of the antibody or antigen-binding fragment of claim 18 to a human having the disease or disorder, such that the disease or disorder is diminished, wherein the disease or disorder is inflammation, Myasthenia gravis, Graves' disease, idiopathic thrombocytopenia purpura, hemolytic anemia, diabetes mellitus, Crohn's disease, multiple sclerosis, a drug-induced autoimmune disease, rejection of a transplanted organ, graft-vs-host disease, an allergic response, an autoimmune response, fibrosis, gastrointestinal disease, vascular disease, a T cell cancer, or viral infection of T cells by the HTLV I virus.

29. A method of antagonizing CD154 activity in a subject having a disease or disorder associated with CD154, the method comprising administering to the subject an effective amount of the antibody or antigen-binding fragment of claim 1, such that the disease or disorder is diminished, wherein the disease or disorder is inflammation, Myasthenia gravis, Graves' disease, idiopathic thrombocytopenia purpura, hemolytic anemia, diabetes mellitus, Crohn's disease, multiple sclerosis, a drug-induced autoimmune disease, rejection of a transplanted organ, graft-vs-host disease, an allergic response, an autoimmune response, fibrosis, gastrointestinal disease, vascular disease, a T cell cancer, or viral infection of T cells by the HTLV I virus.

30. A method of antagonizing CD154 activity in a subject having a disease or disorder associated with CD154, the method comprising administering to the subject an effective amount of the antibody or antigen-binding fragment of claim 28, such that the disease or disorder is diminished, wherein the disease or disorder is inflammation, Myasthenia gravis, Graves' disease, idiopathic thrombocytopenia purpura, hemolytic anemia, diabetes mellitus, Crohn's disease, multiple sclerosis, a drug-induced autoimmune disease, rejection of a transplanted organ, graft-vs-host disease, an allergic response, an autoimmune response, fibrosis, gastrointestinal disease, vascular disease, a T cell cancer, or viral infection of T cells by the HTLV I virus.

31. A method of inhibiting inflammation in a subject, the method comprising administering to the subject an effective amount of an antibody or antigen binding fragment thereof that binds CD154 and that comprises a light chain variable region, which comprises light chain CDRs VL CDR1, VL CDR2, and VL CDR3, and a heavy chain variable region, which comprises heavy chain CDRs VH CDR1, VH CDR2, and VH CDR3, wherein
  (i) VL CDR1, VL CDR2, and VL CDR3 respectively have the sequences of
    (a) amino acids 24-38, 54-60, and 93-101 of SEQ ID NO:1 or
    (b) amino acids 24-38, 54-60, and 93-101 of SEQ ID NO:1 except that one or a combination of substitutions is present, wherein the substitutions are selected from the group consisting of
    Ser at position 26 substituted with Asp,
    Gln at position 27 substituted with Glu, and
    Thr at position 33 substituted with Trp;
  and
  (ii) VH CDR1, VH CDR2, and VH CDR3 respectively have the sequences of
    (a) amino acids 26-35, 50-66, and 99-107 of SEQ ID NO:4 or
    (b) amino acids 26-35, 50-66, and 99-107 of SEQ ID NO:4 except that one or a combination of substitutions is present, wherein the substitutions are selected from the group consisting of
    Thr at position 30 substituted with His,
    Tyr at position 33 substituted with Trp, and
    Ser at position 54 substituted with Asn;
  wherein when the light chain CDR sequences have the wild type 5c8 CDR sequences according to (i)(a) above, the heavy chain CDR sequences are not the wild type 5c8 CDR sequences according to (ii)(a) above,
  thereby inhibiting inflammation in the subject.

32. A method of treating lupus in a subject, the method comprising administering to the subject an effective amount of an antibody or antigen binding fragment thereof that binds CD154 and that comprises a light chain variable region, which comprises light chain CDRs VL CDR1, VL CDR2, and VL CDR3, and a heavy chain variable region, which comprises heavy chain CDRs VH CDR1, VH CDR2, and VH CDR3, wherein
  (i) VL CDR1, VL CDR2, and VL CDR3 respectively have the sequences of
    (a) amino acids 24-38, 54-60, and 93-101 of SEQ ID NO:1 or
    (b) amino acids 24-38, 54-60, and 93-101 of SEQ ID NO:1 except that one or a combination of substitutions is present, wherein the substitutions are selected from the group consisting of
    Ser at position 26 substituted with Asp,
    Gln at position 27 substituted with Glu, and
    Thr at position 33 substituted with Trp;
  and
  (ii) VH CDR1, VH CDR2, and VH CDR3 respectively have the sequences of
    (a) amino acids 26-35, 50-66, and 99-107 of SEQ ID NO:4 or
    (b) amino acids 26-35, 50-66, and 99-107 of SEQ ID NO:4 except that one or a combination of substitutions is present, wherein the substitutions are selected from the group consisting of
    Thr at position 30 substituted with His,
    Tyr at position 33 substituted with Trp, and
    Ser at position 54 substituted with Asn;
  wherein when the light chain CDR sequences have the wild type 5c8 CDR sequences according to (i)(a) above, the heavy chain CDR sequences are not the wild type 5c8 CDR sequences according to (ii)(a) above,
  thereby treating lupus in the subject.

33. The method of claim 32, wherein the lupus is systemic lupus erythematosus.

34. The method of claim 32, wherein the lupus is drug-induced lupus.

35. A method of treating an autoimmune response in a subject, the method comprising administering to the subject an effective amount of an antibody or antigen binding fragment thereof that binds CD154 and that comprises a light chain variable region, which comprises light chain CDRs VL CDR1, VL CDR2, and VL CDR3, and a heavy chain variable region, which comprises heavy chain CDRs VH CDR1, VH CDR2, and VH CDR3, wherein
  (i) VL CDR1, VL CDR2, and VL CDR3 respectively have the sequences of
    (a) amino acids 24-38, 54-60, and 93-101 of SEQ ID NO:1 or (b) amino acids 24-38, 54-60, and 93-101 of SEQ ID NO:1 except that one or a combination of substitutions is present, wherein the substitutions are selected from the group consisting of
Ser at position 26 substituted with Asp,
Gln at position 27 substituted with Glu, and
Thr at position 33 substituted with Trp;
and
(ii) VH CDR1, VH CDR2, and VH CDR3 respectively have the sequences of
  (a) amino acids 26-35, 50-66, and 99-107 of SEQ ID NO:4 or
  (b) amino acids 26-35, 50-66, and 99-107 of SEQ ID NO:4 except that one or a combination of substitutions is present, wherein the substitutions are selected from the group consisting of
Thr at position 30 substituted with His,
Tyr at position 33 substituted with Trp, and
Ser at position 54 substituted with Asn;
wherein when the light chain CDR sequences have the wild type 5c8 CDR sequences according to (i)(a) above, the heavy chain CDR sequences are not the wild type 5c8 CDR sequences according to (ii)(a) above
thereby treating the autoimmune response in the subject.

* * * * *